(12) United States Patent
Traverse et al.

(10) Patent No.: US 11,566,004 B2
(45) Date of Patent: Jan. 31, 2023

(54) PROCESS FOR THE PREPARATION OF BROMODOMAIN INHIBITOR

(71) Applicant: Celgene Quanticel Research, Inc., San Diego, CA (US)

(72) Inventors: John Fitzgerald Traverse, Summit, NJ (US); Kelvin Hin-Yeong Yong, Summit, NJ (US); Antonio Christian Ferretti, Summit, NJ (US); Hekla Alite, Carteret, NJ (US); Jonathan Moseley, Bristol (GB); Antonio Maria Ruda, South Glamorgan (GB); David Primer, Summit, NJ (US); Steven Philp, Abingdon (GB)

(73) Assignee: CELGENE QUANTICEL RESEARCH, INC., San Diego, CA (US)

( * ) Notice: Subject to any disclaimer, the term of this patent is extended or adjusted under 35 U.S.C. 154(b) by 0 days.

(21) Appl. No.: 17/262,642

(22) PCT Filed: Jul. 23, 2019

(86) PCT No.: PCT/US2019/042914
§ 371 (c)(1),
(2) Date: Jan. 22, 2021

(87) PCT Pub. No.: WO2020/023438
PCT Pub. Date: Jan. 30, 2020

(65) Prior Publication Data
US 2022/0064121 A1 Mar. 3, 2022

Related U.S. Application Data

(60) Provisional application No. 62/702,085, filed on Jul. 23, 2018.

(51) Int. Cl.
*C07D 217/24* (2006.01)
(52) U.S. Cl.
CPC ................. *C07D 217/24* (2013.01)
(58) Field of Classification Search
CPC .......................... C07D 217/24; A61K 31/472
USPC ......................................... 546/141; 514/309
See application file for complete search history.

(56) References Cited

U.S. PATENT DOCUMENTS

| 4,287,085 A | 9/1981 | Takei et al. |
| 9,034,900 B2 | 5/2015 | Bennett et al. |
| 2004/0092754 A1 | 5/2004 | Schafer et al. |
| 2014/0296239 A1 | 10/2014 | Ruf et al. |
| 2015/0111885 A1 | 4/2015 | Bennett et al. |

FOREIGN PATENT DOCUMENTS

| EP | 1 652 842 A1 | 5/2006 |
| WO | WO 2010/102154 A2 | 9/2010 |
| WO | WO 2016/172618 A1 | 10/2016 |

OTHER PUBLICATIONS

Lennox, et al., "Selection of Boron Reagents for Suzuki-Miyaura Coupling," *Chem. Soc. Rev.*, vol. 43, p. 412-443 (2014).
Oberhauser, et al., A New Bromination Method for Phenols and Anisoles: NBS/HBF(4), *The Journ. of Organic Chemistry*, p. 4504 (Jun. 1997).
Database REaxys [Online] Elsevier; Jan. 1, 1986, Allain Le Canu: "Comptes Rendus Hebdomadaires des Seances de 1' Academie des Sciences, 103, 385", XP002798484, Database Accession No. RX-ID 271109.
Pei, et al., "Discovery, Structure-Activity Relationship, and Pharmacological Evaluation of (5-Substituted-Pyrrolidinyl-2-Carbonyl)-2-Cyanopyrrolidines as Potent Dipeptidyl Peptidase IV Inhibitors," *Journ. of Medicinal Chemistryi, American Chemical Society*, vol. 49, No. 12, pp. 3520-3535 (Jan. 2006).
Chow, et al., "A Decade Advancement of Transition Metal-Catalyzed Borylation of Aryl Halides and Sulfonates," RSC Adv., vol. 3, 12518-12539 (2013).
Maluenda, et al., Recent Developments in the Suzuki-Miyaura Reaction: 2010-2014, *Molecules*, vol. 20, pp. 7528-7557 (2015).
Kaila, et al., "Discovery of isoquinolinone indole acetic acids as antagonists of chemoattractant receptor homologous molecule expressed on Th2 cells (CRTH2) for the treatment of allergic inflammatory diseases," *J. Med. Chem.*, 57: pp. 1299-1322 (2014).
Miyaura, et al., "Palladium-Catalyzed Cross-Coupling Reactions of Organoboron Compounds," *Chem. Rev.*, 95(7), pp. 2457-2483 (1995).
Gilis, et al., "Multistep Synthesis of Complex Boronic Acids from Simple MIDA Boronates," *J. Am. Chem. Soc.*, 730(43): pp. 14084-14085 (2008).
Bonin et al., "Aryl Diazonium versus Iodonium Salts: Preparation, Applications and Mechanisms for the Suzuki-Miyaura Cross-Coupling Reaction," *Tetrahedron Lett.*, 52, pp. 1132-1135 (2011).
Lennox, et al., "Selection of Boron Reagents for Suzuki-Miyaura Coupling," *Chem. Soc. Rev.*, vol. 43, pp. 412-443 (2014).
International Preliminary Report on Patentability issued in International Patent Application No. PCT/US2019/042914, dated Feb. 4, 2021.

*Primary Examiner* — Jeffrey H Murray
(74) *Attorney, Agent, or Firm* — Foley & Lardner LLP

(57) ABSTRACT

The present invention provides processes of synthesis and purification of a bromodomain inhibitor, Compound 1, which compound includes crystalline forms, amorphous forms, solvates, and hydrates thereof. Embodiments of the disclosure relate to chemical synthesis routes of Compound 1 that provide a scalable method that results in highly pure final product. A further embodiment relates to methods to isolate the most stable polymorph of Compound 1 by crystallization from formic acid and water.

17 Claims, 25 Drawing Sheets

Figure 10B

| | K3PO4 | K2CO3 | KOH | KOAc |
|---|---|---|---|---|
| EtOH | ● | ● | ● | ● |
| Pr-OH | ● | ● | ● | ● |
| iPrOH | ● | ● | ● | ● |
| n-BuOH | ● | ● | ● | ● |
| 2-BuOH | ● | ● | ● | ● |
| t-amylOH | ● | ● | ● | ● |

Figure 10A

| | DMF | THF | n-BuOH | toluene |
|---|---|---|---|---|
| SPhos | ● | ● | ● | ● |
| XPhos | ● | ● | ● | ● |
| CataCXium A | ● | ● | ● | ● |
| Aphos | ● | ● | ● | ● |
| PCy3 | ● | ● | ● | ● |
| pEPPSI | · | ∘ | ● | ∘ |

Compound 4 to Compound 5 Reaction Profile: Portion-wise Addition of NBS, Seeding

PROCESS FOR THE PREPARATION OF BROMODOMAIN INHIBITOR

CROSS-REFERENCE TO RELATED APPLICATION

This application is the U.S. National Stage of International Patent Application No. PCT/US2019/042914, filed Jul. 23, 2019, which claims priority to U.S. Provisional Patent Application No. 62/702,085, filed Jul. 23, 2018, the entire contents of these applications is incorporated herein by reference in their entirety.

TECHNICAL FIELD

The present invention relates to methods for preparing pharmaceutical compositions and in particular to processes of synthesis and purification of a bromodomain inhibitor useful for the treatment of cancer.

BACKGROUND

The bromodomain (BRD) proteins are an important class of histone reader proteins that recognize acetylated lysine residues (KAc) on histone tails and direct transcription complexes to turn on genes. Among the eight BRD families, the BRD and BET (bromodomain and extra-terminal) proteins have been found to be tractable for drug discovery. Chemical inhibition of BET proteins exerts a broad spectrum of desirable biological effects such as anticancer, anti-inflammatory, and male contraceptive properties.

U.S. Pat. No. 9,034,900 discloses a series of bromodomain inhibitors with nanomolar affinity for BET proteins. The discovery of these potent, selective, and permeable inhibitors for BET bromodomain proteins has stimulated research activity in diverse therapeutic areas, particularly in oncology. Several cancer clinical trials for small molecule inhibitors of BET bromodomain proteins have been initiated. In particular, the bromodomain inhibitor 4-[2 (cyclopropylmethoxy)-S-methylsulfonylphenyl]-2-methylisoquinolin-1-one disclosed in U.S. Pat. No. 9,034,900 is in a clinical trial for the treatment of advanced solid tumors and relapsed/refractory Non-Hodgkin's lymphomas (NCT03220347).

4-[2-(cyclopropylmethoxy)-S-methylsulfonylphenyl]-2-methylisoquinolin-1-one, referred to herein as Compound 1, has the following structure:

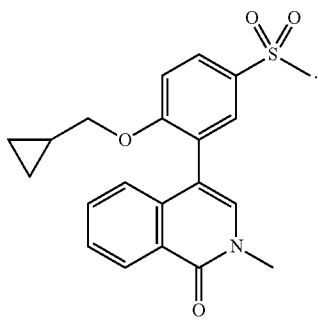

The synthesis route and purification process of bromodomain inhibitors disclosed in U.S. Pat. No. 9,034,900 require multiple silica gel column chromatography or preparative HPLC purifications of intermediates and final compound, and thus have overall modest yield and impure final product. To realize the medical benefits of the bromodomain inhibitor for cancer treatment, the industry needs a scalable and robust purification process for the preparation of bromodomain inhibitors. This disclosures satisfies this need.

SUMMARY

Described herein is an improved process for the industrial scale production of bromodomain inhibitors. Another object of the invention is to provide a suitable purification method for preparation of the final product.

The present embodiments provide processes of synthesis and purification of a bromodomain inhibitor, the compound 4-[2 (cyclopropylmethoxy)-S-methylsulfonylphenyl]-2-methylisoquinolin-1-one ("Compound 1"), which compound includes crystalline forms, amorphous forms, solvates, and hydrates thereof; as well as pharmaceutical compositions that include this compound.

Certain embodiments of the disclosure relate to chemical synthesis routes of Compound 1 that do not require column chromatography and are amenable to large scale synthesis. The overall synthetic sequence and intermediates are not changed as disclosed in U.S. Pat. No. 9,034,900 but many reagents, procedures and isolation techniques are modified and improved for the good manufacturing practices (GMP) manufacture of kilograms of Compound 1.

In one embodiment, provided is a process for the preparation of a compound of formula I, a hydrate, solvate, prodrug, or pharmaceutically acceptable salt thereof:

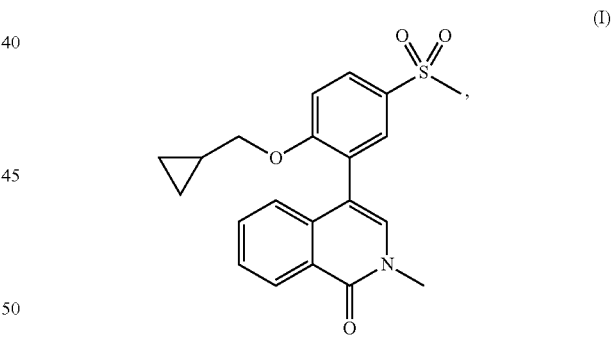

wherein the process comprises coupling a compound of formula II with a compound of formula III, to provide the compound of formula I;

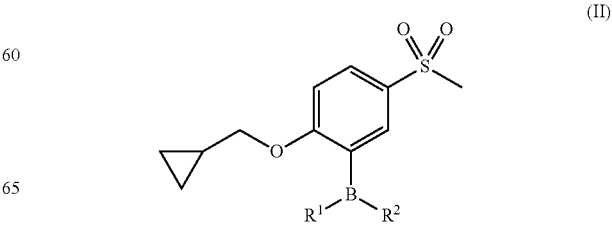

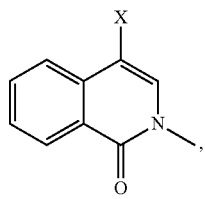

(III)

wherein:
X is Cl, Br, or I; and
R¹ and R² are each independently selected from H, OH, optionally substituted $C_1$-$C_8$ alkyl, optionally substituted $C_1$-$C_8$ alkoxy, optionally substituted $C_1$-$C_5$ alkenyl, optionally substituted $C_1$-$C_5$ alkynyl, optionally substituted 4-10 membered heterocyclyl, optionally substituted 5-10 membered heteroaryl, optionally substituted 6-10 membered aryl, or an optionally substituted 4-7 membered cycloalkyl; or R¹, R² and the boron to which they are attached together form an optionally substituted 5-10 membered ring comprising carbon and from 0 to 5 heteroatoms.

In other aspects of this method, (i) X is Br; and/or (ii) R¹, R² and the boron to which they are attached together form an optionally substituted 5-10 membered ring comprising carbon and from 0 to 5 heteroatoms selected from O and N. Further, in yet another aspect of the methods of the disclosure, R¹, R² and the boron to which they are attached together form an optionally substituted 5-10 membered ring wherein the two atoms of the ring directly attached to boron are oxygens. In another aspect of the methods, the optionally substituted 5-10 membered ring comprising boron comprises from 1 to 3 nitrogen atoms. Further, the optionally substituted ring comprising boron can be an 8 membered ring.

In another embodiment of the disclosure, the compound of formula II has the formula II-a:

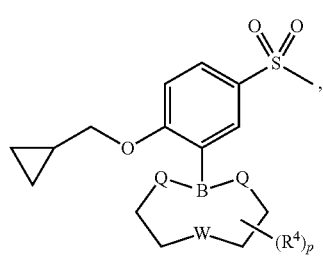

(II-a)

wherein:
each Q is independently selected from —O—, —NH—, —N(R⁵)—, or optionally substituted methylene;
W is —O—, —NH— or —N(R⁵)—;
each R⁴ is independently selected from H, OH, CN, optionally substituted amino, —C(O)R⁵, —COOR⁵, —C(O)N(R⁵)₂, —SO2R⁵, an optionally substituted $C_1$-$C_5$ alkyl, an optionally substituted $C_1$-$C_5$ alkenyl, an optionally substituted $C_1$-$C_5$ alkynyl, an optionally substituted 4-10 membered heterocyclyl, an optionally substituted 5-10 membered heteroaryl, an optionally substituted 6-10 membered aryl, or an optionally substituted 4-7 membered cycloalkyl;
each R⁵ is independently selected from H, an optionally substituted $C_1$-$C_5$ alkyl, an optionally substituted $C_1$-$C_5$ alkenyl, an optionally substituted $C_1$-$C_5$ alkynyl, an optionally substituted 4-10 membered heterocyclyl, an optionally substituted 5-10 membered heteroaryl, an optionally substituted 6-10 membered aryl, or an optionally substituted 4-7 membered cycloalkyl; and
p is 0 to 4.

Alternatively, the compound of formula II has the following formula II-b:

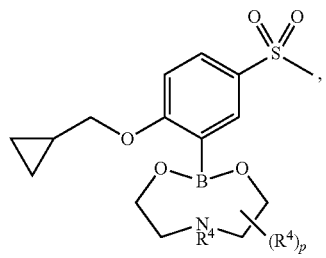

(II-b)

wherein:
each R⁴ is independently selected from H, OH, CN, optionally substituted amino, —C(O)R⁵, —COOR⁵, —C(O)N(R⁵)₂, —SO₂R⁵, an optionally substituted $C_1$-$C_5$ alkyl, an optionally substituted $C_1$-$C_5$ alkenyl, an optionally substituted $C_1$-$C_5$ alkynyl, an optionally substituted 4-10 membered heterocyclyl, an optionally substituted 5-10 membered heteroaryl, an optionally substituted 6-10 membered aryl, or an optionally substituted 4-7 membered cycloalkyl;
each R⁵ is independently selected from H, an optionally substituted $C_1$-$C_5$ alkyl, an optionally substituted $C_1$-$C_5$ alkenyl, an optionally substituted $C_1$-$C_5$ alkynyl, an optionally substituted 4-10 membered heterocyclyl, an optionally substituted 5-10 membered heteroaryl, an optionally substituted 6-10 membered aryl, or an optionally substituted 4-7 membered cycloalkyl; and
p is 0 to 4.

In one embodiment of the disclosure, the compound of formula II is:

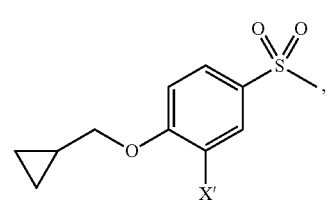

The compound of formula II can be formed by contacting a compound of formula IV with bis(pinacolato)diboron ($B_2pin_2$), a palladium catalyst, and diethanolamine (DEA) (DEA is added after the first reaction is complete), wherein the compound of formula IV has the following structure:

(IV)

wherein X' is Cl, Br, or I.

Further, the compound of formula IV can be produced by monobromination of a compound of formula V:

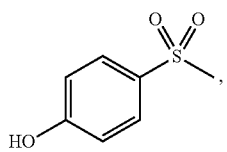
(V)

to produce a compound of formula VI:

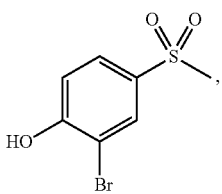
(VI)

and O-alkylating the compound of formula VI to produce the compound of formula IV, wherein X' is Br. The monobromination can proceed over dibromination of the compound of formula V at a ratio of about 95:5 or greater. In another aspect, monobromination can proceed over dibromination of the compound of formula V at a ratio of about 99:1 or greater.

In another aspect of the disclosure, the methods described herein further comprise crystallizing the compound of formula I from a mixture of formic acid and water. The crystallized compound of formula I can comprise the X-ray powder diffraction (XRPD) pattern having the following specifications:

TABLE 1

| No. | Pos. [°2θ] | d-spacing [Å] | Rel. Int. [%] |
|---|---|---|---|
| 1 | 7.807098 | 11.32447 | 13.16 |
| 2 | 8.691139 | 10.17446 | 15.67 |
| 3 | 8.944468 | 9.88685 | 40.82 |
| 4 | 11.47771 | 7.70979 | 20.22 |
| 5 | 13.75333 | 6.43883 | 19.45 |
| 6 | 15.27651 | 5.80009 | 8.04 |
| 7 | 15.69109 | 5.64776 | 64.51 |
| 8 | 15.99297 | 5.54183 | 66.46 |
| 9 | 16.27756 | 5.44557 | 7.77 |
| 10 | 16.89633 | 5.24752 | 43.12 |
| 11 | 17.50072 | 5.06763 | 36.25 |
| 12 | 17.96524 | 4.93763 | 88.03 |
| 13 | 19.20236 | 4.62223 | 11.22 |
| 14 | 19.70334 | 4.50582 | 15.85 |
| 15 | 20.50266 | 4.33193 | 20.82 |
| 16 | 21.13626 | 4.20348 | 38.66 |
| 17 | 21.89583 | 4.05935 | 81.05 |
| 18 | 22.10196 | 4.02195 | 61.36 |
| 19 | 22.57031 | 3.93954 | 13.52 |
| 20 | 22.97552 | 3.87097 | 16.48 |
| 21 | 23.32722 | 3.8134 | 25.65 |
| 22 | 23.5865 | 3.77206 | 13.16 |
| 23 | 24.44054 | 3.64216 | 100 |
| 24 | 25.17524 | 3.53751 | 6.64 |
| 25 | 25.60385 | 3.47925 | 14.72 |
| 26 | 26.41086 | 3.37474 | 9.88 |
| 27 | 27.71849 | 3.21844 | 12.35 |
| 28 | 28.72787 | 3.10761 | 4.64 |

TABLE 1-continued

| No. | Pos. [°2θ] | d-spacing [Å] | Rel. Int. [%] |
|---|---|---|---|
| 29 | 29.60304 | 3.0177 | 3.73 |
| 30 | 31.95225 | 2.801 | 2.61 |
| 31 | 32.84832 | 2.72661 | 5.47 |
| 32 | 33.83981 | 2.64895 | 2.15 |
| 33 | 34.39729 | 2.60729 | 2.3 |
| 34 | 35.02682 | 2.56186 | 3.75 |
| 35 | 35.70021 | 2.51506 | 2.55 |
| 36 | 37.16499 | 2.41923 | 2.11 |
| 37 | 38.06795 | 2.3639 | 8.22 |
| 38 | 38.94192 | 2.31284 | 1.09. |

In one embodiment, the methods or processes described herein result in a compound of formula I having a purity of at least about 90%, about 95%, or about 99%.

Described in the disclosure are compounds of formula I, a hydrate, solvate, prodrug, or pharmaceutically acceptable salt thereof, produced by any of the processes described herein.

In one aspect of the disclosure, described is a process of monobrominating a compound of formula VII, the process comprising monobrominating the compound of formula VII to produce a compound of formula VIII.

Two processes are described herein to make a compound of formula VIII. Process 1 (methylene chloride process) relies on the differentially in solubilities of this particular compound. Process 2 (TFA process) relies on the solution chemistry; the latter process may provide better control over a wider range of substrates, although both processes provide suitable compounds.

Thus, the methylene chloride procedure may not work for any meta-directing group besides $SO_2Me$ (halogens are electron withdrawing groups (EWGs), as this process relies on specific physical attributes for bromination control (the mono-bromide is crystallized). However, the MeCN/TFA procedure should be more general to any meta directing EWG The compounds of formula VII and formula VIII have the following structures:

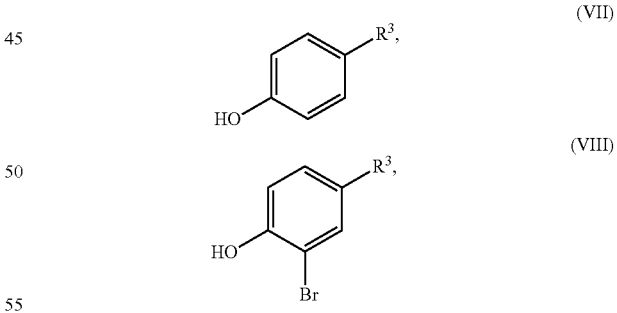

wherein:

$R^3$ is selected from the group consisting of $SO_2R^4$, $NO_2$, CN, $SO_3H$, CHO, $C(O)R^4$, $COOR^4$, $CO_2H$, $C(O)N(R^4)_2$, and $C(O)NH_2$;

$R^4$ is H optionally substituted $C_1$-$C_8$ alkyl, optionally substituted $C_1$-$C_8$ cycloalkyl, optionally substituted 4-10 membered heterocyclyl, optionally substituted 6-10 membered aryl, and optionally substituted 5-10 membered heteroaryl; and wherein the compound of formula VIII has a purity of greater than about 99% by weight.

In one aspect of this method or process, the compound of formula VIII is washed with water at a temperature between about 18° C. and 23° C. In another aspect, the method or process further comprises subjecting the washed compound of formula VIII to drying at a temperature from about 23° C. to about 85° C. In addition, the compound of formula VIII can be washed with acetonitrile (MeCN) prior to washing with water.

Both the foregoing summary and the following brief description of the drawings and detailed description are exemplary and explanatory. They are intended to provide further details, but are not to be construed as limiting. Other objects, advantages, and novel features will be readily apparent to those skilled in the art from the following detailed description.

BRIEF DESCRIPTION OF THE DRAWINGS

FIGS. 10A and B show a heatmap summarizing catalyst performance (FIG. 10A), where high performance liquid chromatography (HPLC) yields for this screening span from <5% up to ~85%. Larger circles indicate higher yield. Lighter circles indicate higher cleanliness. FIG. 10B shows a heatmap with HPLC yields ranging from ~50-95%. Larger, darker circles indicate higher yield.

DETAILED DESCRIPTION

I. Overview

Figure 1:
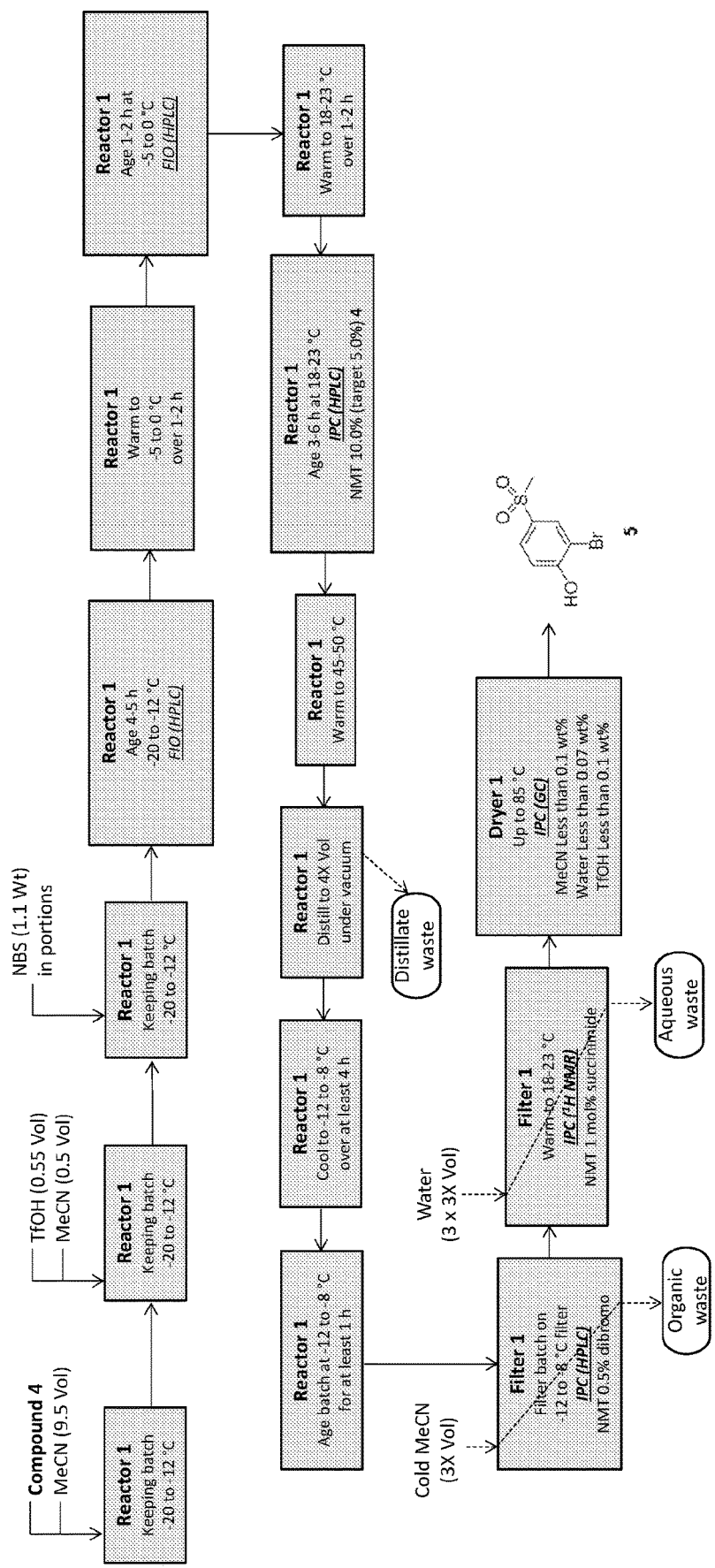
FIG. 1 illustrates a process for the process scale synthesis of intermediate 5 from a commercially available compound.

The present application relates to the development of a preferred process or method synthesis of Compound 1. In particular, in a preferred embodiment the method can provide for large or multi-kilogram scale synthesis of Compound 1. In another preferred embodiment, the synthesis method does not require preparative chromatography or complex purification procedures. In one aspect, the final synthetic step for synthesizing Compound 1 includes a cross-coupling reaction between boronate ester Compound 2' and bromide Compound 3 as shown below.

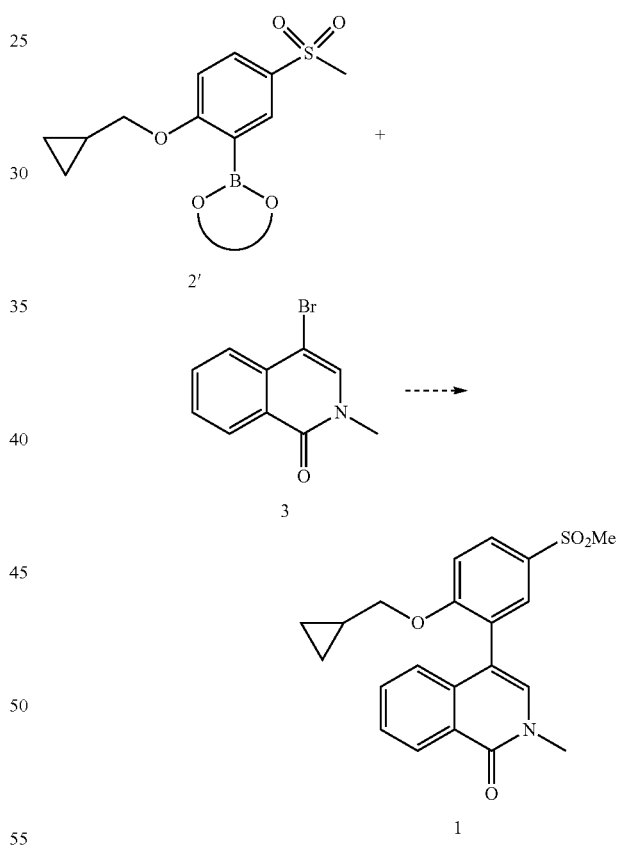

Problematically, previous efforts to prepare boronate esters such as Compound 2' have been met with difficulty related to product stability and scalability. In the present disclosure, the inventors describe a solution to this problem employing the use of boronate ester Compound 2, shown below. Compound 2 was prepared on a multi-kilogram scale, in high purity, without the need for cumbersome purification operations and was successfully coupled to bromide Compound 3 to produce the target Compound 1 with high yield and purity.

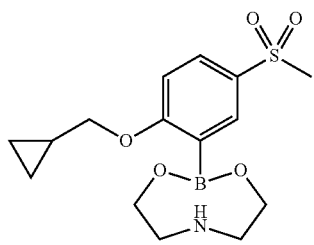

II. Synthesis of Compound 1

In one aspect a process for the preparation of a compound of formula I, a hydrate, solvate, prodrug, or pharmaceutically acceptable salt thereof is provided, wherein the compound of formula I has the following structure:

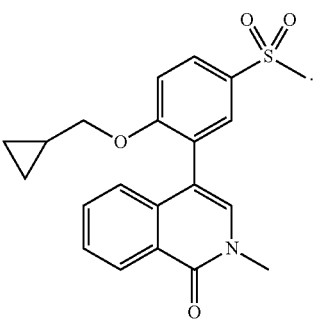
(I)

The process or method preferably comprises coupling a compound of formula II with a compound of formula III, to provide the compound of formula I,

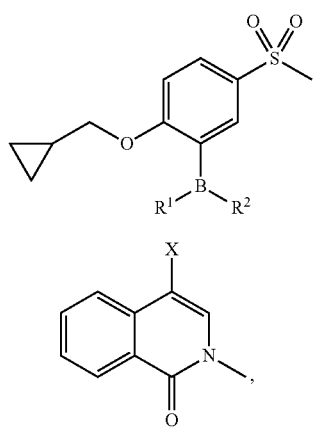
(II)

(III)

wherein:
X is Cl, Br, or I; and
$R^1$ and $R^2$ are each independently selected from H, OH, optionally substituted $C_1$-$C_8$ alkyl, optionally substituted $C_1$-$C_8$ alkoxy, optionally substituted $C_1$-$C_5$ alkenyl, optionally substituted $C_1$-$C_5$ alkynyl, optionally substituted 4-10 membered heterocyclyl, optionally substituted 5-10 membered heteroaryl, optionally substituted 6-10 membered aryl, or an optionally substituted 4-7 membered cycloalkyl; or $R^1$, $R^2$ and the boron to which they are attached together form an optionally substituted 5-10 membered ring comprising carbon and from 0 to 5 heteroatoms.

In some embodiments, $R^1$, $R^2$ and the boron to which they are attached form an optionally substituted 5-10 membered ring comprising carbon and from 0 to 5 heteroatoms. In some embodiments, the heteroatom(s) are each independently selected from O and N.

In some embodiments, $R^1$, $R^2$ and the boron to which they are attached form an optionally substituted 5 membered ring. In some embodiments, $R^1$, $R^2$ and the boron to which they are attached form an optionally substituted 6 membered ring. In some embodiments, $R^1$, $R^2$ and the boron to which they are attached form an optionally substituted 7 membered ring. In some embodiments, $R^1$, $R^2$ and the boron to which they are attached form an optionally substituted 8 membered ring. In some embodiments, $R^1$, $R^2$ and the boron to which they are attached form an optionally substituted 9 membered ring. In some embodiments, $R^1$, $R^2$ and the boron to which they are attached form an optionally substituted 5 membered ring.

In some embodiments, $R^1$, $R^2$ and the boron to which they are attached form an optionally substituted 5-10 membered ring comprising (i) carbon and no heteroatoms; (ii) carbon and 1 heteroatom; (iii) carbon and 2 heteroatoms; (iv) carbon and 3 heteroatoms; (v) carbon and 4 heteroatoms; or (vi) carbon and 5 heteroatoms.

In some embodiments, the heteroatom(s) are each independently selected from O, S, N, or P.

In some embodiments, the compound of formula II is of formula II-a:

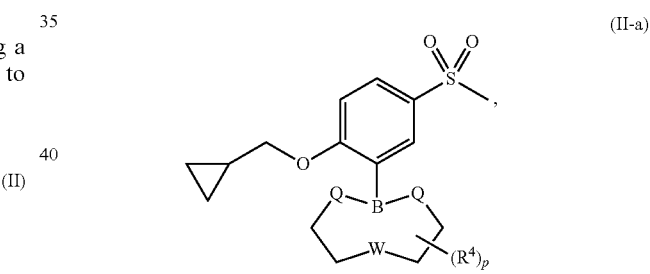
(II-a)

wherein:
each Q is independently selected from —O—, —NH— or —N($R^5$)—, or optionally substituted methylene;
W is —O—, —NH— or —N($R^5$)—;
each $R^4$ is independently selected from H, OH, CN, optionally substituted amino, —C(O)$R^5$, —COO$R^5$, —C(O)N($R^5$)$_2$, —SO$_2R^5$, an optionally substituted $C_1$-$C_5$ alkyl, an optionally substituted $C_1$-$C_5$ alkenyl, an optionally substituted $C_1$-$C_5$ alkynyl, an optionally substituted 4-10 membered heterocyclyl, an optionally substituted 5-10 membered heteroaryl, an optionally substituted 6-10 membered aryl, or an optionally substituted 4-7 membered cycloalkyl;
each $R^5$ is independently selected from H, an optionally substituted $C_1$-$C_5$ alkyl, an optionally substituted $C_1$-$C_5$ alkenyl, an optionally substituted $C_1$-$C_5$ alkynyl, an optionally substituted 4-10 membered heterocyclyl, an optionally substituted 5-10 membered heteroaryl, an optionally substituted 6-10 membered aryl, or an optionally substituted 4-7 membered cycloalkyl; and
p is 0 to 4.

In some embodiments the compound of formula II is of formula II-b:

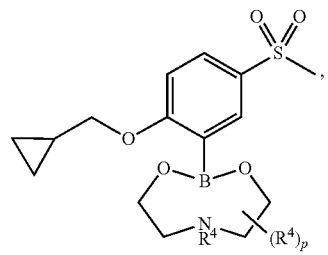

(II-b)

wherein:

each $R^4$ is independently selected from H, OH, CN, optionally substituted amino, —C(O)$R^5$, —COO$R^5$, —C(O)N($R^5$)$_2$, —SO$_2$$R^5$, an optionally substituted $C_1$-$C_5$ alkyl, an optionally substituted $C_1$-$C_5$ alkenyl, an optionally substituted $C_1$-$C_5$ alkynyl, an optionally substituted 4-10 membered heterocyclyl, an optionally substituted 5-10 membered heteroaryl, an optionally substituted 6-10 membered aryl, or an optionally substituted 4-7 membered cycloalkyl;

each $R^5$ is independently selected from H, an optionally substituted $C_1$-$C_5$ alkyl, an optionally substituted $C_1$-$C_5$ alkenyl, an optionally substituted $C_1$-$C_5$ alkynyl, an optionally substituted 4-10 membered heterocyclyl, an optionally substituted 5-10 membered heteroaryl, an optionally substituted 6-10 membered aryl, or an optionally substituted 4-7 membered cycloalkyl; and p is 0 to 4.

In some embodiments, the compound of formula II is:

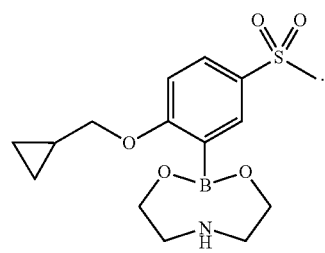 [SMILES: CS(=O)(=O)c1ccc(OCC2CC2)c(B2OCCNCCO2)c1]

Figure 5:
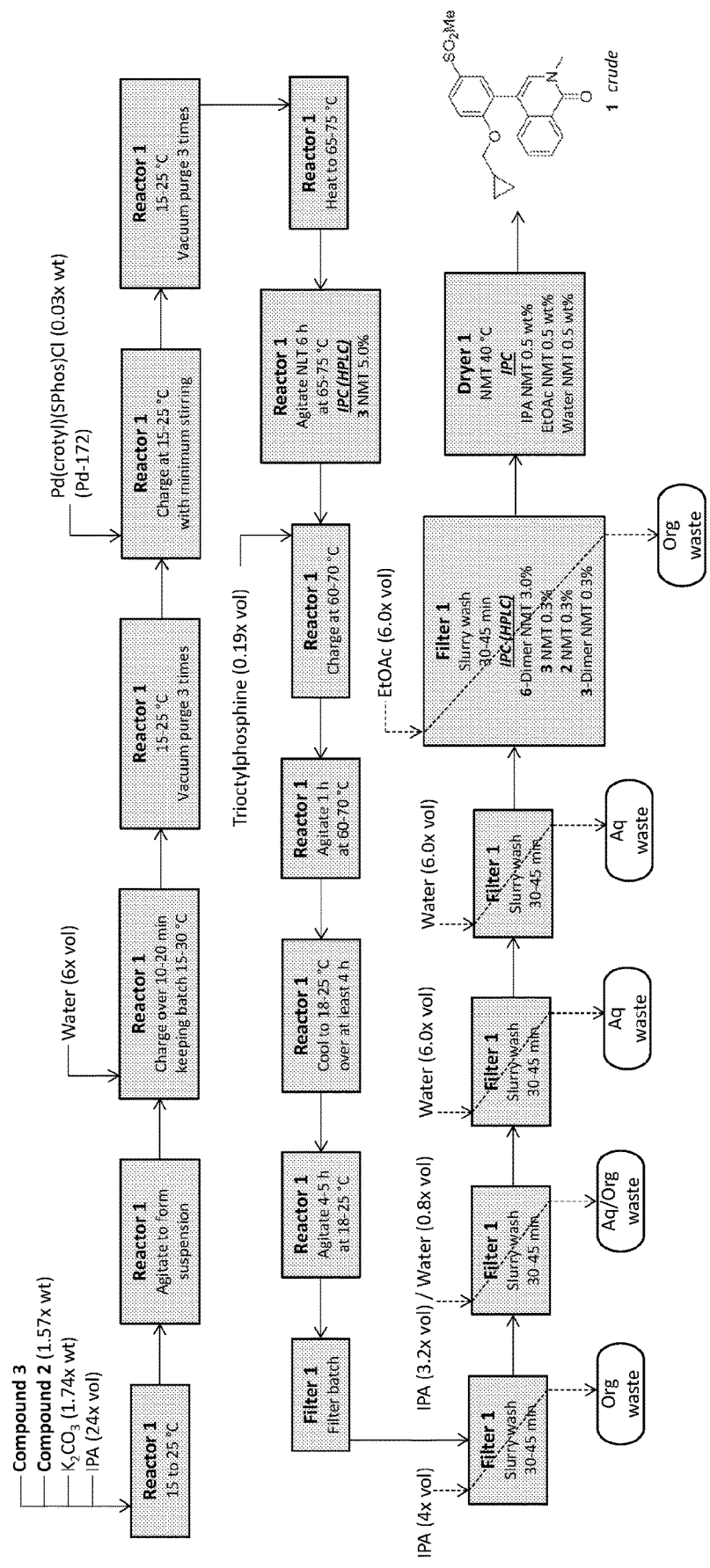
FIG. 5 illustrates a process for the process scale synthesis of target compound 1 by coupling cross-coupling partners 2 and 3.

Referring to FIG. 5, the process may comprise charging a reactor with the compound of formula II, the compound of formula III, a base, and isopropanol (IPA) at a temperature between about 15° C. to about 25° C. For example, the temperature can be about 15, about 16, about 17, about 18, about 19, about 20, about 21, about 22, about 23, about 24, or about 25° C.

In some embodiments, the ratio of the compound of formula II to the compound of formula III is between about 1:1 to about 3:1. In some embodiments, the base is potassium carbonate. The reactor can be agitated to form a suspension followed by charging with water over about 10 to about 20 minutes (or any time period in between or including these two values, such as about 10, about 11, about 12, about 13, about 14, about 15, about 16, about 17, about 18, about 19, or about 20 mins), and maintaining the temperature between about 15° C. to about 25° C. (e.g., about 15, about 16, about 17, about 18, about 19, about 20, about 21, about 22, about 23, about 24, or about 25° C.). The reactor is then vacuum purged 3× (3 times) followed by charging with Pd-catalyst. In one embodiment, the Pd catalyst is SPhos Pd(crotyl)Cl having the structure below wherein Cy is cyclohexyl:

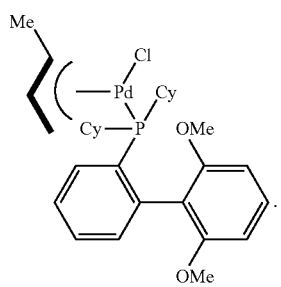

The reactor can be vacuum purged and then heated to between about 65° C. and 75° C. (e.g., about 65, about 66, about 67, about 68, about 69, about 70, about 71, about 72, about 73, about 74 or about 75° C.), and agitated for about 5 hr to about 8 hr (or any time period in between or including these two values, such as about 5, about 5.25, about 5.5, about 5.75, about 6, about 6.25, about 6.5, about 6.75, about 7, about 7.25, about 7.5, about 7.75, or about 8 hrs). The reactor is then charged with trioctylphosine at about 60° C. to 70° C. (or any temperature in between or including these two values, such as about 60, about 61, about 62, about 63, about 64, about 65, about 66, about 67, about 68, about 69, or about 70° C.) and agitated for about 0.5 hr to about 1.5 hr (or any time period in between or including these two values, such as about 0.5, about 0.6, about 0.7, about 0.8, about 0.9, about 1.0, about 1.1, about 1.2, about 1.3, about 1.4, or about 1.5 hrs). The process further comprises cooling the reactor to between about 18° C. and 25° C. (or any temperature in between or including these two values, such as about 18, about 19, about 20, about 21, about 22, about 23, about 24, or about 25° C.) over a period of time between about 3 hr and about 5 hr (or any time period in between or including these two values, such as about 3, about 3.25, about 3.5, about 3.75, about 4, about 4.25, about 4.5, about 4.75, or about 5 hrs). The reaction slurry in the reactor is then filtered, washed with IPA and filtered, washed with IPA/water and filtered, and washed with water and optionally filtered twice. The slurry is then washed with ethyl acetate and filtered, then dried at a temperature not more than about 40° C. to furnish crude 1.

Figure 6:
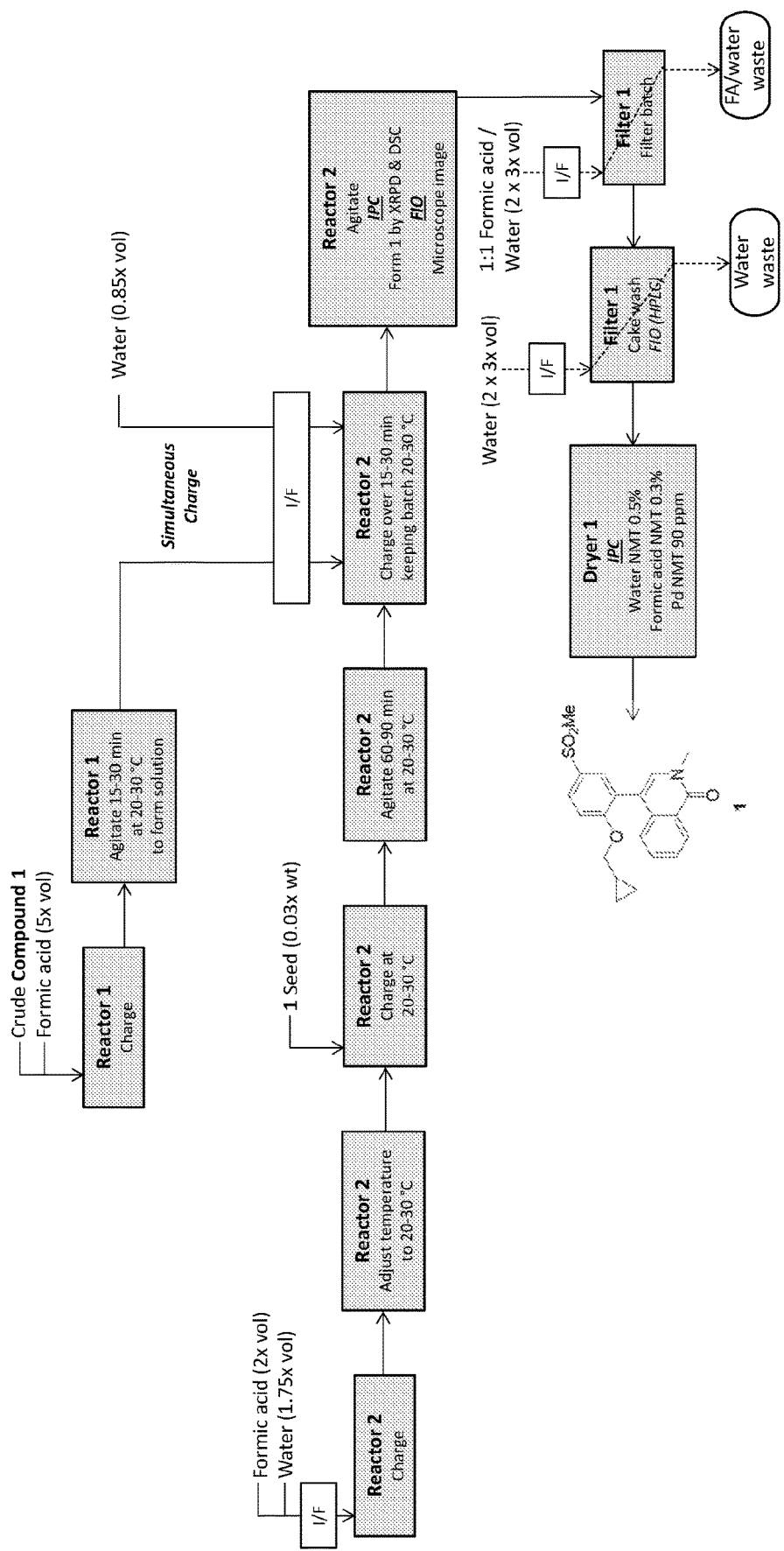
FIG. 6 illustrates a process for the process scale purification of 1.

In some embodiments, the process further comprises crystallizing the compound of formula I from formic acid and water. Referring to FIG. 6, in some embodiments, crystallizing comprises charging a first reactor with Compound 1 in formic acid and agitating for about 15 min to about 30 min (or any time period in between or including these two values, such as about 15, about 16, about 17, about 18, about 19, about 20, about 21, about 22, about 23, about 24, about 25, about 26, about 27, about 28, about 29 or about 30 mins) at a temperature between about 20° C. and about 30° C. (or any temperature in between or including these two values such as about 20, about 21, about 22, about 23, about 24, about 25, about 26, about 27, about 28, about 29, about or 30° C.). A second reactor is charged with formic acid and water, adjusted to a temperature between about 20° C. and about 30° C. (or any temperature in between or including these two values such as about 20, about 21, about 22, about 23, about 24, about 25, about 26, about 27, about 28, about 29, about or 30° C.), seeded with Compound 1, and agitated for about 60 min to about 90 min. (or any time period in between or including these two values, such as about 60, about 65, about 70, about 75, about 80, about 85, or about 90 mins). Over a period of about 15 to about 30 mins (or any time period in between or including these two values, such as about 15, about 16, about 17, about 18, about 19, about 20, about 21, about 22, about 23, about 24, about 25, about 26, about 27, about 28, about 29 or about 30 mins), the second reactor is simultaneously charged with the solution from the first reactor and water while maintaining the temperature in the second reactor between about 20° C. and about 30° C. (or any temperature in between or including these two values such as about 20, about 21, about 22, about 23, about 24, about 25, about 26, about 27, about 28, about 29, about or 30° C.). The mixture in the second reactor is agitated and the solids filtered and washed with a formic acid/water mixture, then just water. The solids are dried to furnish crystalized 1.

In some embodiments, crystalized Compound 1 is polymorph Form 1, comprising the X-ray powder diffraction (XRPD) pattern of Table 2:

TABLE 2

| No. | Pos. [°2 theta] | d-spacing [Å] | Rel. Int. [%] |
|---|---|---|---|
| 1 | 7.807098 | 11.32447 | 13.16 |
| 2 | 8.691139 | 10.17446 | 15.67 |
| 3 | 8.944468 | 9.88685 | 40.82 |
| 4 | 11.47771 | 7.70979 | 20.22 |
| 5 | 13.75333 | 6.43883 | 19.45 |
| 6 | 15.27651 | 5.80009 | 8.04 |
| 7 | 15.69109 | 5.64776 | 64.51 |
| 8 | 15.99297 | 5.54183 | 66.46 |
| 9 | 16.27756 | 5.44557 | 7.77 |
| 10 | 16.89633 | 5.24752 | 43.12 |
| 11 | 17.50072 | 5.06763 | 36.25 |
| 12 | 17.96524 | 4.93763 | 88.03 |
| 13 | 19.20236 | 4.62223 | 11.22 |
| 14 | 19.70334 | 4.50582 | 15.85 |
| 15 | 20.50266 | 4.33193 | 20.82 |
| 16 | 21.13626 | 4.20348 | 38.66 |
| 17 | 21.89583 | 4.05935 | 81.05 |
| 18 | 22.10196 | 4.02195 | 61.36 |
| 19 | 22.57031 | 3.93954 | 13.52 |
| 20 | 22.97552 | 3.87097 | 16.48 |
| 21 | 23.32722 | 3.8134 | 25.65 |
| 22 | 23.5865 | 3.77206 | 13.16 |
| 23 | 24.44054 | 3.64216 | 100 |
| 24 | 25.17524 | 3.53751 | 6.64 |
| 25 | 25.60385 | 3.47925 | 14.72 |
| 26 | 26.41086 | 3.37474 | 9.88 |
| 27 | 27.71849 | 3.21844 | 12.35 |
| 28 | 28.72787 | 3.10761 | 4.64 |
| 29 | 29.60304 | 3.0177 | 3.73 |
| 30 | 31.95225 | 2.801 | 2.61 |
| 31 | 32.84832 | 2.72661 | 5.47 |
| 32 | 33.83981 | 2.64895 | 2.15 |
| 33 | 34.39729 | 2.60729 | 2.3 |
| 34 | 35.02682 | 2.56186 | 3.75 |
| 35 | 35.70021 | 2.51506 | 2.55 |
| 36 | 37.16499 | 2.41923 | 2.11 |
| 37 | 38.06795 | 2.3639 | 8.22 |
| 38 | 38.94192 | 2.31284 | 1.09 |

In some embodiments, the purity of a compound of formula I is at least about 90%. In some embodiments, the purity of compound of formula I is at least about 91%, about 92%, about 93%, about 94%, about 95%, about 96%, about 97%, about 98%, or about 99%. In some embodiments, the purity of a compound of formula I is at least 99%. In some embodiments, the purity of a compound of formula I is at least 99.5%. In some embodiments, the purity of a compound of formula I is at least 99.9%.

III. Synthesis of Cross-Coupling Partner Compound 2

In some embodiments, the compound of formula II is formed by reacting a compound of formula IV:

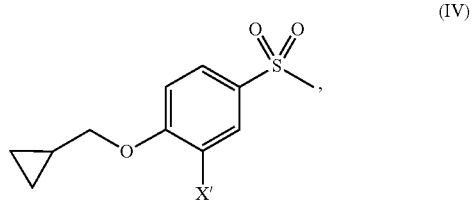

wherein $X^1$ is Cl, Br, or I; with bis(pinacolato)diboron ($B_2pin_2$), a palladium catalyst, and diethanolamine (DEA). In some embodiments, X' is Br.

In some embodiments, the compound of formula IV is obtained by monobromination of a compound of formula V:

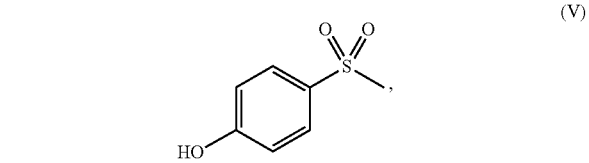

to produce a compound of formula VI:

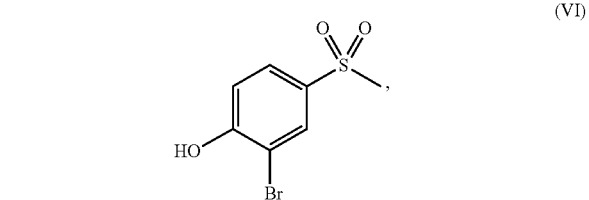

and O-alkylating the compound of formula VI to produce the compound of formula IV, wherein X' is Br (Compound 6).

In some embodiments, monobromination proceeds over dibromination of the compound of formula V at a ratio of about 80:20 or greater. In some embodiments, monobromination proceeds over dibromination of the compound of formula V at a ratio of about 90:10 or greater. In some embodiments, monobromination proceeds over dibromination of the compound of formula V at a ratio of about 95:5 or greater. In some embodiments, monobromination proceeds over dibromination of the compound of formula V at a ratio of about 95:5 or greater. In some embodiments, monobromination proceeds over dibromination of the compound of formula V at a ratio of about 99:1 or greater.

In another aspect, described is a process of monobrominating a compound of formula VII:

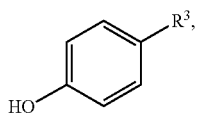

(VII)

to produce a compound of formula (VIII):

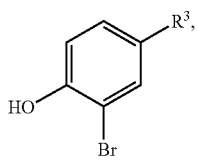

(VIII)

is provided,
wherein:

R³ is selected from the group consisting of $SO_2R^4$, $NO_2$, CN, $SO_3H$, CHO, $C(O)R^4$, $COOR^4$, $CO_2H$, $C(O)N(R^4)_2$, and $C(O)NH_2$;

R⁴ is H optionally substituted $C_1$-$C_8$ alkyl, optionally substituted $C_1$-$C_8$ cycloalkyl, optionally substituted 4-10 membered heterocyclyl, optionally substituted 6-10 membered aryl, and optionally substituted 5-10 membered heteroaryl; and wherein the compound of formula VIII has a purity of greater than about 90%, about 91%, about 92%, about 93%, about 94%, about 95%, about 96%, about 97%, about 98% or about 99% by weight. The process or method can comprise monobrominating the compound of formula VII to produce the compound of formula VIII.

In some embodiments, monobrominating comprises contacting the compound of formula VII with N-bromosuccinimide (NBS). In some embodiments, the washing of the crude compound of formula VIII with water is at about 18° C. to about 23° C. (or any temperature in between or including these two values, such as about 18, about 19, about 20, about 21, about 22 or about 23° C.). In some embodiments, the process further comprises subjecting the washed crude compound of formula VIII to drying at a temperature from about 23° C. to about 85° C. (or any value in between or including these two temperatures, such as about 23, about 25, about 30, about 35, about 40, about 45, about 50, about 55, about 60, about 65, about 70, about 75, about 80, about or 85° C.). In some embodiments, the crude compound of formula VIII is washed with acetonitrile (MeCN) prior to washing with water. In some embodiments, the washing with MeCN is at a temperature between about –12° C. and about –8° C. (or any temperature in between or including these two values, such as about –12, about –11, about –10, about –9, or about –8° C.).

The procedure allows for the following modifications. Solvents: Alternative solvents could be used. Examples include chlorinated solvents, such as chloroform or 1,2 dichloroethane, and non-chlorinated solvents such as acetonitrile, tetrahydrofuran, or 2-methyltetrahydrofuran. Reaction concentration: The reaction concentration can be varied from about 2× vol to about 20× vol (with respect to Compound 4). Brominating agents: Additional brominating reagents include bromine and 1,3-dibromo-5,5-dimethylhydantoin. Bromination reagent stoichiometry: Different amounts of the brominating reagent can be used, from about 0.8 equiv to about 1.9 equiv. Bromination reagent addition: The brominating reagent can be added all at once, portion wise in about 2 to about 20 portions, or continuously. The addition times can vary from about 0 to about 72 hours. Temperature: Reaction temperatures from about 0° C. to about 40° C. could be used. Acids: Different acids can be envisioned, including benzenesulfonic acid, para-toluenesulfonic acid, triflic acid, hydrobromic acid, and trifluoroacetic acid. Isolation: Instead of directly filtering the product and washing with methylene chloride and water, at the end of reaction an organic solvent capable of dissolving Compound 5 could be charged, followed by an aqueous workup to remove succinimide, and addition of an antisolvent or solvent exchange to an appropriate solvent to crystallize Compound 4. Drying: A temperature range of about 10 to about 60° C. could be used for drying.

An alternative process to Compound 5 has also been developed. This process is advantageous in that it does not use a chlorinated solvent, and provides additional controls over the formation of the Compound 5-a dibromo impurity. See Oberhauser, T. J. Org. Chem 1997, 62, 4504-4506. The process is as follows. Compound 4 (10 g, 58 mmol) and acetonitrile (100 ml) were charged to the reactor and agitated. The batch was cooled to –20° C. Triflic acid ($CF_3SO_3H$ or TfOH, 5.5 mL, 62 mmol) was charged while maintaining a batch temperature of –10 to –25° C. N-bromosuccinimide was charged (NBS, 11.4 g, 64 mmol), stirred at –10 to –25° C. for 30 minutes, then warmed to 20° C. over 3 to 4 hours. Agitation was continued at 15° C. to 25° C. until reaction completion. If the reaction conversion plateaued before completion, the reaction was cooled to –5 to –15° C., and additional NBS was added, the amount based off of unreacted starting material, followed by warming to 15° C. to 25° C. and reacting until complete.

Alternatives to the above procedure employing MeCN and TfOH are as follows. Brominating agents: Additional brominating reagents include bromine and 1,3-dibromo-5, 5-dimethylhydantoin. Bromination Reagent Stoichiometry: Different amounts of the brominating reagent can be used, from about 0.8 equiv to about 2 equiv. Drying: A temperature range of about 10° C. to about 60° C. could be used for drying.

In some embodiments, the compound of formula VIII has a purity of greater than about 90% by weight. In some embodiments, the compound of formula VIII has a purity of greater than about 91%, about 92%, about 93%, about 94%, about 95%, about 96%, about 97%, about 98%, or about 99% by weight. In some embodiments, the compound of formula VIII has a purity of greater than about 99% by weight. In some embodiments, the compound of formula VIII has a purity of greater than about 99.9% by weight.

Referring to FIG. 1, the compound of formula VI (Compound 5) may be prepared from the compound of formula V (Compound 4) by charging a reactor with acetonitrile (MeCN) and Compound 4 at a temperature between about –20° C. and about –12° C. (or any amount in between or including these two values, such as about –20, about –19, about –18, about –17, about –16, about –15, about –14, about –13, or about –12° C.). The reactor is then charged with an acid and MeCN. In some embodiments, the acid is triflic acid (TfOH). N-bromosuccinimide (NBS) is then added to the reactor in portions and the reactor aged between about 4 and about 5 hr. The reactor is then warmed to a temperature between about –5° C. to about 0° C. (or any amount in between or including these two values, such as about –5, about –4, about –3, about –2, about –1, or about 0° C.)

The process further comprises warming the reactor to between about 18° C. and about 23° C. (or any temperature in between or including these values, such as about 18, about 19, about 20, about 21, about 22, or about 23° C.) over a period of time of about 1 hr to about 2 hr (or any time period in between or including these two values, such as about 1, about 1.25, about 1.75, or about 2 hrs) and aging for an additional time period between about 3 hr to about 6 hr (or any time period in between or including these values, such as about 3, about 3.25, about 3.5, about 3.75, about 4, about 4.25, about 4.5, about 4.75, about 5, about 5.25, about 5.5, about 5.75, or about 6 hrs). The process further comprises warming the reactor to between about 45° C. and about 50° C. (or any temperature in between or including these values, such as about 45, about 46, about 47, about 48, about 49, or about 50° C.) and distilling waste off the slurry under vacuum. The reactor is then cooled to between about −12° C. and about −8° C. (or any temperature in between these two values, such as about −12, about −11, about −10, about −9, about −8° C.) over a period of time of about 0.1 hr to about 4 hr (or any time period in between or including these values, such as about 0.1, about 0.5, about 1, about 1.25, about 1.5, about 1.75, about 2, about 2.25, about 2.5, about 2.75, about 3, about 3.25, about 3.5, about 3.75, or about 4 hrs) and aging the batch at this temperature for at least about 1 hr. The slurry is then filtered and washed with cold MeCN, warmed to between about 18° C. and about 23° C. (or any temperature in between these two values, such as about 18, about 19, about 20, about 21, about 22 or about 23° C.) and filtered and washed with water. The remains are then dried at a temperature between about 23° C. and about 85° C. (or any temperature in between these two values, such as about or any value in between or including these two temperatures, such as about 23, about 25, about 30, about 35, about 40, about 45, about 50, about 55, about 60, about 65, about 70, about 75, about 80, about or 85° C.) to furnish Compound 5.

Figure 2:
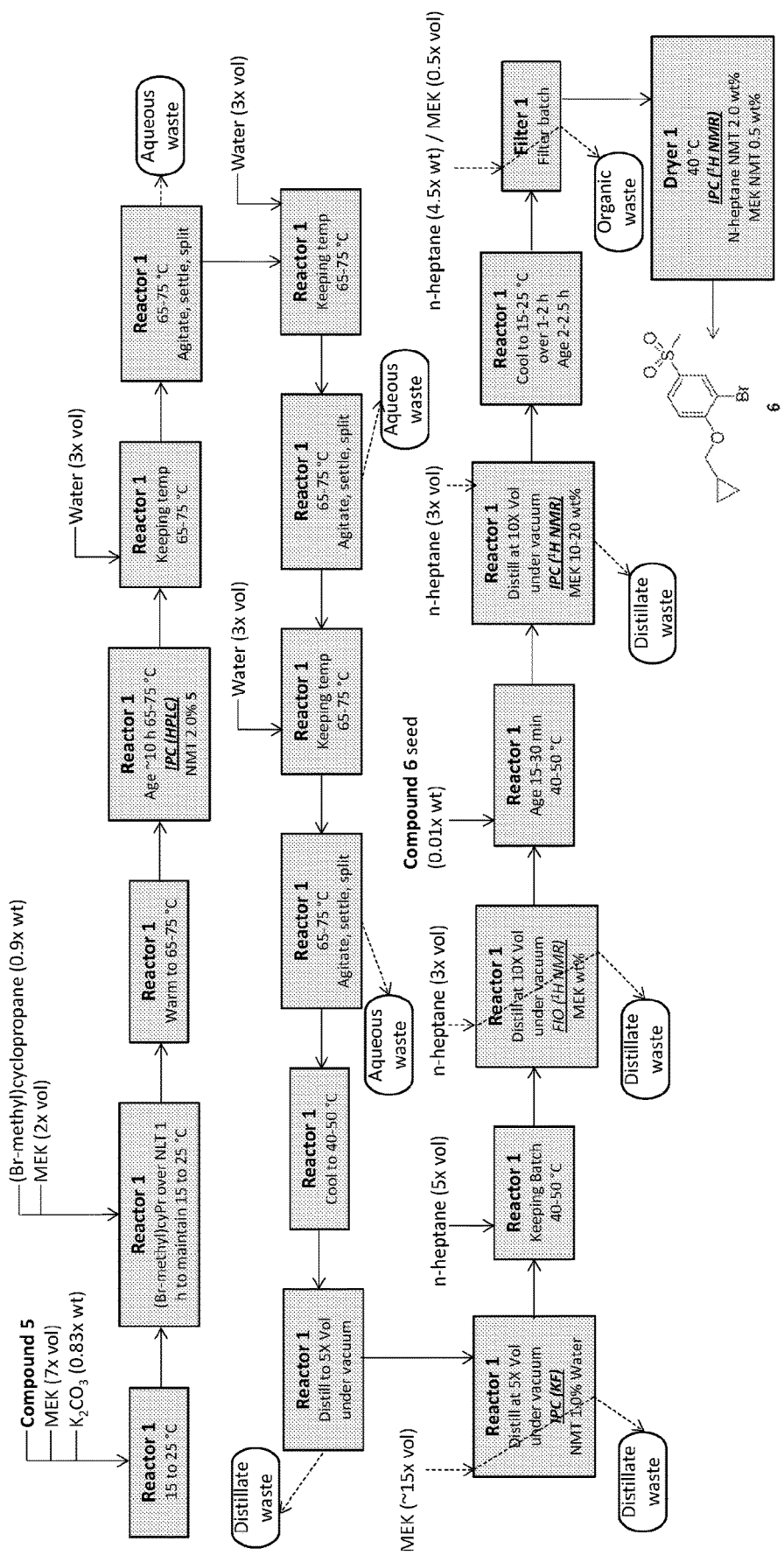
FIG. 2 illustrates a process for the process scale synthesis of intermediate 6 from intermediate 5.

Referring to FIG. 2, Compound 6 is prepared by charging a reactor at a temperature between about 15° C. and about 25° C. (or any temperature in between these two values, such as about 15, about 16, about 17, about 18, about 19, about 20, about 21, about 22, about 23, about 24, or about 25° C.) with Compound 5, methyl ethyl ketone (MEK) and a base. In some embodiments, the base is potassium carbonate. The reactor is then charged with bromomethyl cyclopropane in MEK over a period of time greater than about 1 hr. The reactor is then warmed to a temperature between about 65° C. and about 75° C. (or any temperature in between or including these two values, such as about 65, about 66, about 67, about 68, about 69, about 70, about 71, about 72, about 73, about 74, about 75° C.) and aged for a period of time between about 7 and about 13 hrs (or any time period in between or including these two values, such as about 7, about 8, about 9, about 10, about 11, about 12, about or 13 hours). The reactor is subsequently charged with water, agitated, and the aqueous layer removed followed by repeating this step of charging with water, agitating and removal of the aqueous layer, two more times.

The reactor is then cooled to a temperature between about 40 and about 50° C. (or any temperature in between or including these two values, such as about 40, about 41, about 42, about 43, about 44, about 45, about 46, about 47, about 48, about 49, or about 50° C.). The slurry is distilled under vacuum to remove distillate waste, charged with MEK, distilled under vacuum to remove distillate waste, charged with heptane, and distilled under vacuum to remove distillate waste once again. The reactor is then seeded with Compound 6, charged with heptane, and distilled under vacuum to remove distillate waste. The reactor is then cooled to a temperature between about 15° C. and about 25° C. (or any temperature in between these two values, such as about 15, about 16, about 17, about 18, about 19, about 20, about 21, about 22, about 23, about 24, or about 25° C.) over a period of time between about 1 to about 2 hr (or any time period in between or including these values, such as about 1, about 1.1, about 1.2, about 1.3, about 1.4, about 1.5, about 1.6, about 1.7, about 1.8, about 1.9, or about 2 hrs), and aged for about 2 to about 2.5 hr (or any time period in between or including these values, such as about 2, about 2.1, about 2.2, about 2.3, about 2.4, or about 2.5 hrs). The mixture is then filtered and washed with heptane and MEK and dried at a temperature between about 30° C. and about 50° C. (or any temperature in between or including these values, such as about 30, about 35, about 40, about 45, about 50° C.) to furnish Compound 6.

Figure 3:
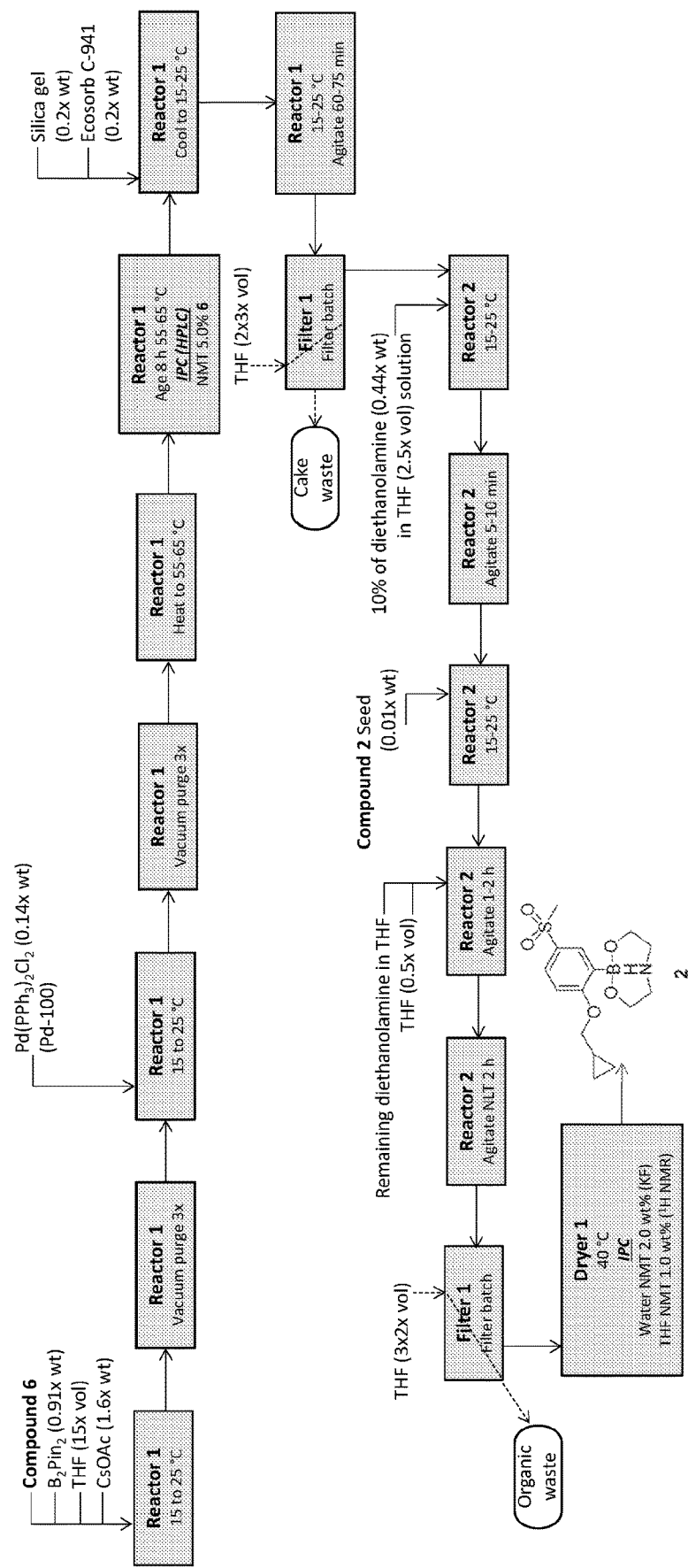
FIG. 3 illustrates a process for the process scale synthesis of cross-coupling partner 2 from intermediate 6.

Referring to FIG. 3, finally Compound 6 is converted to the cross-coupling partner Compound 2 as follows. A first reactor at a temperature between about 15° C. and about 25° C. (or any temperature in between these two values, such as about 15, about 16, about 17, about 18, about 19, about 20, about 21, about 22, about 23, about 24, or about 25° C.) is charged with Compound 6, bis(pinacolato)diboron ($B_2Pin_2$), and cesium acetate in THF. The first reactor is vacuum purged then charged with Pd catalyst and purged again. In some embodiments, the Pd catalyst is bis(triphenylphosphine) palladium(II) dichloride or $Pd(PPh_3)_2Cl_2$. The first reactor is then heated to a temperature between about 55° C. and about 65° C. (or any temperature in between or including these values, such as about 55, about 56, about 57, about 58, about 59, about 60, about 61, about 62, about 62, about 64, or about 65° C.), aged for about 6 to about 10 hours (or any time period in between or including these values, such as about 6, about 7, about 8, about 9, about or 10 hrs), cooled to between about 15° C. and about 25° C. (or any temperature in between these two values, such as about 15, about 16, about 17, about 18, about 19, about 20, about 21, about 22, about 23, about 24, or about 25° C.) and charged with silica gel and activated carbon. In some embodiments, the activated carbon is escrob C-941. Other suitable compounds can also be used in this aspect of the method.

The reactor is then agitated for about 30 min to 24 hours, and optionally about 60 min to about 75 min (or any time period in between or including these values, such as about 30 mins, about 40 mins, about 50 mins, about 60 mins, about 1 hr, about 2 hrs, about 3 hrs, about 4 hrs, about 5 hrs, about 6 hrs, about 7 hrs, about 8 hrs, about 9 hrs, about 10 hrs, about 11 hrs, about 12 hrs, about 13 hrs, about 14 hrs, about 15 hrs, about 16 hrs, about 17 hrs, about 18 hrs, about 19 hrs, about 20 hrs, about 21 hrs, about 22, hrs, about 23 hrs, or about 24 hrs) and filtered and washed with tetrahydrofuran (THF). The solid is removed and the filtrate is charged into a second reactor at a temperature between about 15° C. and about 25° C. (or any temperature in between these two values, such as about 15, about 16, about 17, about 18, about 19, about 20, about 21, about 22, about 23, about 24, or about 25° C.). The second reactor is charged with a solution of diethanolamine (DEA) in THF and agitated for a period of time between about 1 min and about 10 min (or any time period in between or including these values, such as about 1, about 2, about 3, about 4, about 5, about 6, about 7, about 8, about 9, or about 10 mins), then seeded with Compound 2. A second portion of DEA in THF is added over about 1 hr to about 2 hr and the reactor agitated for an additional about 2 hr to about 5 hr (or any time period in between or including these values, such as about 2, about 3, about 4, or about 5 hrs). The slurry is filtered and washed with THF then dried at a temperature between about 30° C. and about 50° C. (or any temperature in between or including these values such as about 30, about 35, about 40, about 45, about 50° C.) to furnish Compound 2.

The following modifications of the above reaction, synthesis of 6 from 5, may be employed as well. Solvent: Different solvents could be used, for example acetone, methyl isobutyl ketone, ethyl acetate, isopropyl acetate, acetonitrile, or 2-methyl tetrahydrofuran. Reaction volume: Reaction volumes of 3 to 30 volumes with respect to 3 could be used. Base: Different inorganic bases, such as cesium carbonate or phosphate bases (sodium, potassium, or cesium) could be used. Also, organic bases, such as trimethylamine or diisopropyldiimide could be used. Base particle size: Different particle sizes of potassium carbonate from 325 mesh could be used. Reaction temperature: A lower temperature, such as 50° C. could be used. A higher temperature, such as 100° C. could be used. Any temperature above the boiling point of the solvent could be run in a pressure vessel. Isolation: Different solvent ratios of MEK to n-heptane could be used. Different amounts of residual water can be left. Different amounts of seeds, from 0 to 50% could be used. Seeding could take place later in the process and/or at a lower temperature. An un-seeded crystallization can be employed. A different isolation temperature, from 0° C. to 50° C. could be used. A different wash could be used, for example a different ratio of MEK to n-heptane. A different antisolvent from n-heptane could be used, such as hexane, pentane, or methyl tert-butyl ether. Alternatively, the batch could be solvent exchanged into a solvent where Compound 3 has a solubility of less than 100 mg/ml and isolated from this system. Drying: A temperature range of 10 to 60° C. could be used for drying.

The reaction to synthesize 2 from 6 may be modified as follows. Solvent: Different solvents from THF could be used, such as 1,4 dioxane or 2-methyltetrahydrofuran. Reaction volume: The reaction volume can be varied from 4 to 50 volumes with respect to compound 2. Catalyst and base: Different palladium catalysts and bases can be used for the borylation. Examples can be found in Chow, Wing Kin, et al., RSC Adv., 2013, 3, 12518-12539. Borylation reaction temperature: Reaction temperatures from room temperature (20° C.) to solvent reflux can be used. Carbon/Silica treatment: The treatment can be performed without silica gel. The process can be performed without a carbon treatment. Different carbon sources from Ecosorb C-941 can be used. Different amounts of silica, from 0.01× to 1× weight equivalents, can be used. Different amounts of Ecosorb C-941, from 0.01× to 1× weight equivalents, can be used. Crystallization: A different addition rate of diethanolamine can be used. Different amounts of diethanolamine, from 1.0 to 3.0 molar equivalents can be used. A different cake wash with more or less THF can be used. Different amount of seeds from 0.0001× wt to 50× wt can be used. Alternatively, the process can be unseeded. Drying: A temperature range of 10° C. to 60° C. could be used for drying.

IV. Synthesis of Cross-Coupling Partner Compound 3

Cross-coupling partner Compound 3, is prepared from commercially available Compound 8 as shown below.

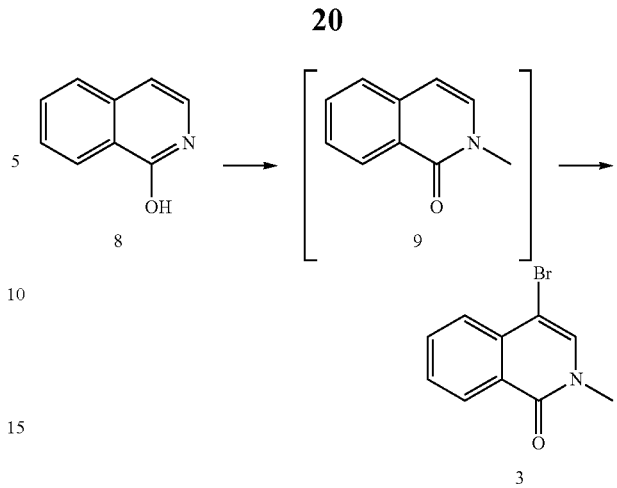

Figure 4A:
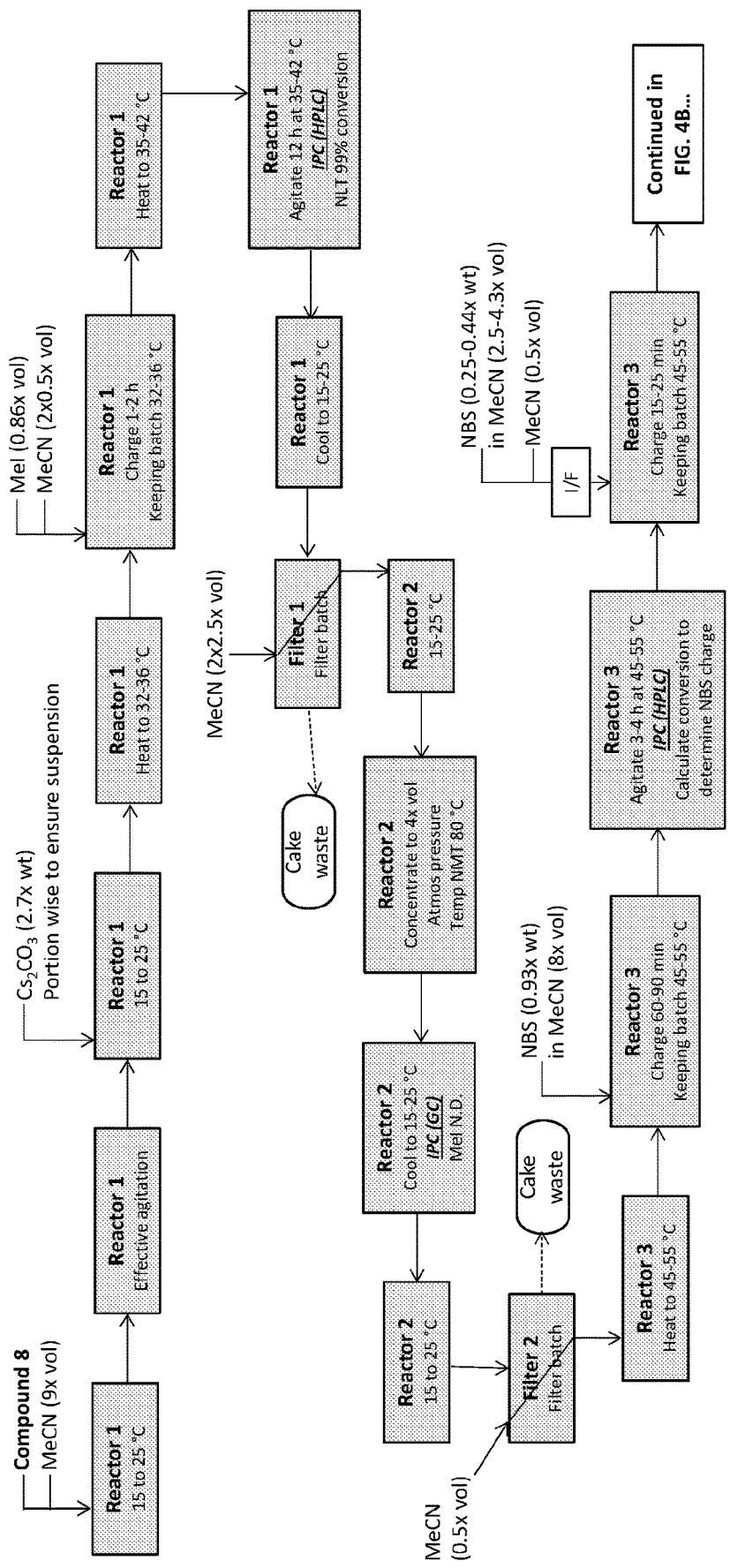
FIGS. 4A and 4B illustrate a process for the process scale synthesis of intermediate 3 from a commercially available compound.

Referring to FIG. 4A, a first reactor is charged with Compound 8 in MeCN at a temperature between about 15° C. and about 25° C. (or any temperature in between these two values, such as about 15, about 16, about 17, about 18, about 19, about 20, about 21, about 22, about 23, about 24, or about 25° C.). A base, in some embodiments, cesium carbonate, is then added to the first reactor portion wise and the first reactor then heated to a temperature between about 32° C. and about 36° C. (or any temperature in between or including these values, such as about 32, about 33, about 34, about 35, or about 36° C.). The first reactor is then charged with MeI (methyl iodide) in MeCN over about 1 hr to 2 hr (or any time period in between or including these values, such as about 1, about 1.25. about 1.5, about 1.75, or about 2 hrs). The first reactor is then heated to a temperature between about 35° C. and about 42° C. (or any temperature in between and including these values, such as about 35, about 36, about 37, about 38, about 39, about 40, about 41, or about 42° C.) and agitated for about 10 to about 14 hr (or any time period in between and including these values, such as about 10, about 10.5, about 11, about 11.5, about 12, about 12.5, about 13, about 13.5, or about 14 hrs). The first reactor is then cooled to a temperature between about 15° C. and about 25° C. (or any temperature in between these two values, such as about 15, about 16, about 17, about 18, about 19, about 20, about 21, about 22, about 23, about 24, or about 25° C.). filtered and washed with MeCN and the solids discarded while the filtrate is charged into a second reactor at a temperature between about 15° C. and about 25° C. (or any temperature in between these two values, such as about 15, about 16, about 17, about 18, about 19, about 20, about 21, about 22, about 23, about 24, or about 25° C.). The mixture in the second reactor is concentrated at atmospheric pressure at a temperature of about 80° C. The second reactor is then cooled to a temperature between about 15° C. and about 25° C. (or any temperature in between these two values, such as about 15, about 16, about 17, about 18, about 19, about 20, about 21, about 22, about 23, about 24, or about 25° C.) and filtered and washed with MeCN. The solids are discarded and the filtrate charged into a third reactor. The third reactor is then heated to a temperature between about 45° C. and about 55° C. (or any temperature in between or including these values, such as about 45, about 46, about 47, about 48, about 49, about 50, about 51, about 52, about 53, about 54 or about 55° C.). The third reactor is subsequently charged with NBS in MeCN while keeping the third reactor at a temperature between about 45° C. and about 55° C. (or any temperature in between or including these values, such as about 45, about 46, about 47, about 48, about 49, about 50, about 51, about 52, about 53, about 54 or about 55° C.). The third reactor is agitated for about 3 hr to about 4 hr (or any time period in between and including these values, such as about 3, about 3.25, about 3.5, about 3.75, or about 4 hrs) maintaining the temperature, then charged once again with NBS in MeCN and pure MeCN over about 15 min to about 25 min (or any time period in between these two values, such as about 15, about 16, about 17, about 18, about 19, about 20, about 21, about 22, about 23, about 24, or about 25 mins).

Figure 4B:
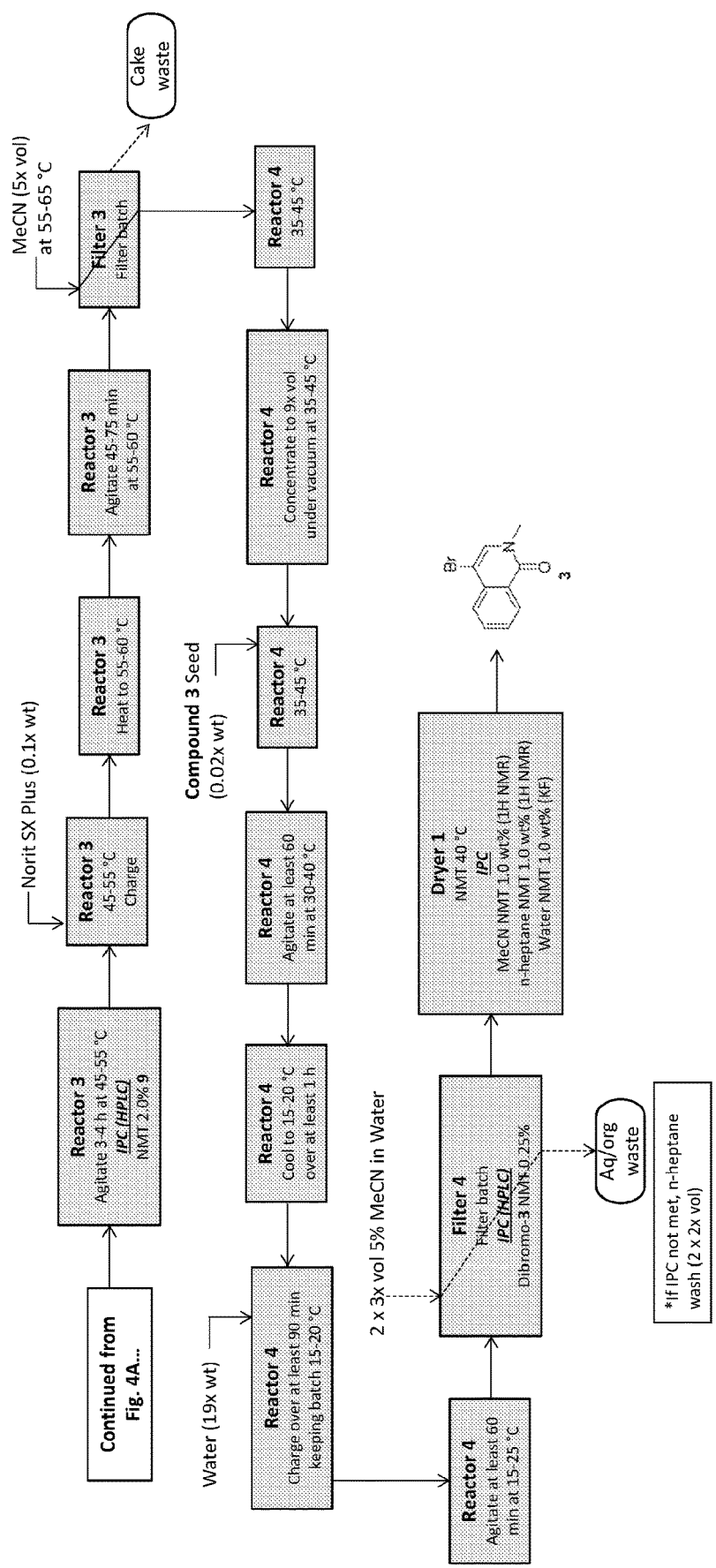

Now referring to FIG. 4B, the third reactor is agitated for about 3 hr to about 4 hr (or any time period in between and including these values, such as about 3, about 3.25, about 3.5, about 3.75, or about 4 hrs) then charged with activated charcoal. The third reactor is then heated to a temperature between about 55° C. and about 60° C. (or any temperature in between and including these values, such as about 55, about 56, about 57, about 58, about 59, or about 60° C.), filtered and washed with MeCN at the same temperature as the third reactor. The solids are discarded and the filtrate charged into a fourth reactor at a temperature between about 45° C. and about 55° C. (or any temperature in between and including these values, such as about 45, about 46, about 47, about 48, about 49, about 50, about 51, about 52, about 54, or about 55° C.). The mixture in the fourth reactor is then concentrated under vacuum at a temperature between about 45° C. and about 55° C. (or any temperature in between and including these values, such as about 45, about 46, about 47, about 48, about 49, about 50, about 51, about 52, about 52, about 54, or about 55° C.), then seeded with Compound 3, agitated at a temperature between about 30° C. and 40° C. (or any temperature in between and including these values, such as about 30, about 31, about 32, about 33, about 34, about 35, about 36, about 37, about 38, about 39, or about 40° C.) for about 60 to 120 min (or any time period in between and including these values, such as about 60, about 65, about 70, about 75, about 80, about 85, about 90, about 95, about 100, about 105, about 110, about 115, or about 120 mins). The fourth reactor is then cooled to a temperature between about 15° C. and 20° C. over about 1 hr to about 2 hr (or any time period in between and including these values, such as about 1, about 1.25, about 1.5, about 1.75, or about 2 hrs). The fourth reactor is then charged with water over about 90 min to about 3 hr maintaining the temperature and agitated for another time period of about 30 min to about 90 min (or any time period in between and including these values, such as about 30, about 35, about 40, about 45, about 50, about 55, about 60, about 65, about 70, about 75, about 80, about 85, or about 90 mins). The slurry was then filtered and washed with MeCN in water (an optionally heptane) and the solids dried at a temperature between about 30° C. and 50° C. (or any temperature in between and including these values, such as about 30, about 35, about 40, about 45, or about 50° C.) to furnish Compound 3.

The first method for synthesis of Compound 3 (Process A in the examples) may be practiced with alternative reagents and conditions as follows. Solvents: Alternative solvents could be used. Examples include chlorinated solvents, such as methylene chloride, chloroform or 1,2 dichloroethane, and non-chlorinated solvents such as tetrahydrofuran, or 2-methyltetrahydrofuran. Reaction concentration: The reaction concentration can be varied from about 2× vol to about 40× vol (with respect to Compound 9). Brominating agents: Additional brominating reagents include bromine and 1,3-dibromo-5,5-dimethylhydantoin. Bromination reagent Stoichiometry: Different amounts of the brominating reagent can be used, from about 0.8 equiv to about 2 equiv. Crystallization: Different amounts of water, including about 5 volumes to about 50 volumes can be used. The crystallization can also proceed without the addition of seeds. Different water addition times and final hold times can be used. Different wash procedures can be used. Drying: A temperature range of about 10° C. to about 60° C. could be used for drying.

The second process (Process B in the examples) for synthesis of Compound 3 may be modified as follows. Solvents: Alternative solvents could be used. Examples include chlorinated solvents, such as methylene chloride, chloroform or 1,2 dichloroethane, and non-chlorinated solvents such as tetrahydrofuran, or 2-methyltetrahydrofuran. Reaction concentration: The reaction concentration can be varied from 2× vol to 40× vol (with respect to Compound 8). Alkylating reagent: Alternative methylating reagents to methyl iodide can be used such as dimethylsulfate. Alkylating reagent stoichiometry: about 1 to about 10 molar equivalents of methyl iodide may be used. Base: Different inorganic bases, such as potassium carbonate or phosphate bases (sodium, potassium, or cesium) could be used. Brominating agents: Additional brominating reagents include bromine and 1,3-dibromo-5,5-dimethylhydantoin. Bromination reagent stoichiometry: Different amounts of the brominating reagent can be used, from about 0.8 equiv to about 2 equiv. Crystallization: Different amounts of water, including about 5 volumes to about 50 volumes can be used. Seeding levels from about 0.0001% to about 50% can be used. The crystallization can also proceed without the addition of seeds. Different water addition times and final hold times can be used. Different wash procedures can be used. Drying: A temperature range of about 10 to about 60° C. could be used for drying.

V. Coupling Compounds 2 and 3 to Form Compound 1

In one embodiment, provided is a process for the preparation of a compound of Compound 1, a hydrate, solvate, prodrug, or pharmaceutically acceptable salt thereof:

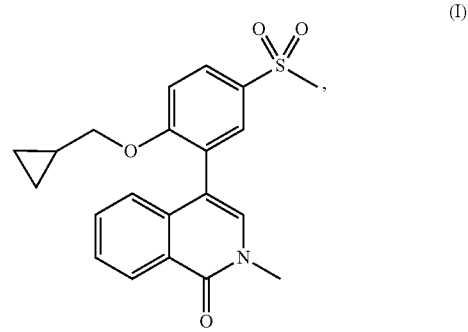 [SMILES: Cn1cc(-c2cc(S(C)(=O)=O)ccc2OCC2CC2)c2ccccc2c1=O]
(I)

wherein the process comprises coupling a compound of formula II with a compound of formula III, to provide the compound of formula I;

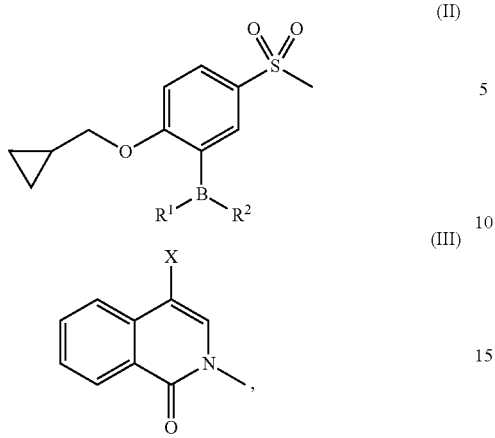

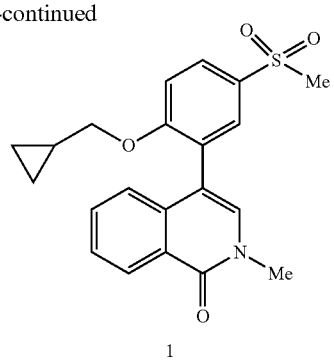

wherein:

X is Cl, Br, or I; and

R$^1$ and R$^2$ are each independently selected from H, OH, optionally substituted C$_1$-C$_8$ alkyl, optionally substituted C$_1$-C$_8$ alkoxy, optionally substituted C$_1$-C$_5$ alkenyl, optionally substituted C$_1$-C$_5$ alkynyl, optionally substituted 4-10 membered heterocyclyl, optionally substituted 5-10 membered heteroaryl, optionally substituted 6-10 membered aryl, or an optionally substituted 4-7 membered cycloalkyl; or R$^1$, R$^2$ and the boron to which they are attached together form an optionally substituted 5-10 membered ring comprising carbon and from 0 to 5 heteroatoms.

In other aspects of this method, (i) X is Br; and/or (ii) R$^1$, R$^2$ and the boron to which they are attached together form an optionally substituted 5-10 membered ring comprising carbon and from 0 to 5 heteroatoms selected from O and N. Further, in yet another aspect of the methods of the disclosure, R$^1$, R$^2$ and the boron to which they are attached together form an optionally substituted 5-10 membered ring wherein the two atoms of the ring directly attached to boron are oxygens. In another aspect of the methods, the optionally substituted 5-10 membered ring comprising boron comprises from 1 to 3 nitrogen atoms. Further, the optionally substituted ring comprising boron can be an 8 membered ring.

Scheme 10: Synthesis of Compound 1

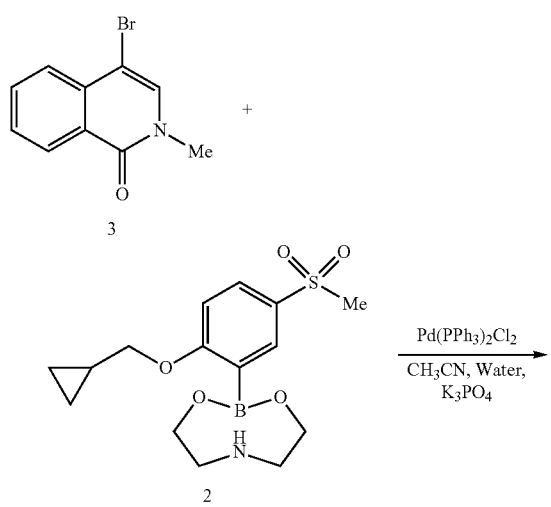

Acetonitrile (1.6 L) was charged to a mixture of Compound 2 (156.7 g, 460 mmol), Compound 3 (100 g, 420 mmol) and potassium phosphate tribasic (223 g, 1.05 mol). Agitation was begun and water (400 mL) charged to the batch. The system was vacuum purged three times with nitrogen and charged with Pd(PPh$_3$)$_2$Cl$_2$ (2.9 g, 4 mmol) and the system vacuum purged three times with nitrogen. The batch was heated to about 65 to about 75° C. (or any temperature in between and including these two values) and contents stirred for at least about 16 hours until reaction was complete by HPLC analysis. The batch was cooled to about 60 to about 70° C. (or any temperature in between and including these two values), agitation halted and the mixture allowed to settle. The bottom aqueous layer was removed. Water (150 mL) and acetonitrile (700 mL) were charged at about 60 to about 70° C. (or any temperature in between and including these two values). Ecosorb C-941 (15 g) and Celite (10 g) were charged to the reaction vessel at about 60 to about 70° C. (or any temperature in between and including these two values). After 1 h, the mixture was filtered to remove solids. The solids were washed twice each with 18% water in acetonitrile (500 mL) at about 60 to about 70° C. (or any temperature in between and including these two values). The filtrates were combined and concentrated under atmospheric pressure to a final volume of 1.5 L. The batch was cooled to about 60 to about 65° C. (or any temperature in between and including these two values) and seeded with Compound 1 (1 g). After 1 h, water (500 mL) was charged over at least 1 hour at about 60 to about 65° C. (or any temperature in between and including these two values). The slurry was cooled to about 15 to about 25° C. (or any temperature in between and including these two values) over 4 hours. The product was collected by suction filtration. The wet cake was washed with 45% water in acetonitrile (500 mL) twice. The product was dried under vacuum at about 40° C. with nitrogen purge. Yield: 139 g of 1.

The above procedure for coupling Compound 3 and Compound 2 to produce Compound 1 may be modified in any of the ways that follow. Reaction solvents: Different reaction solvents from acetonitrile can be used, including tetrahydrofuran, 2-methyl tetrahydrofuran, toluene, and isopropanol. Boronic ester: Different boronic esters from Compound 2 can be used, including pinacolato ester compound 7, and the free boronic acid of Compound 2. Examples of boronic esters can be found in Lennox et al., Chem. Soc. Rev., 43: 412 (2014). Carbon treatment: Different carbon treatments from Ecosorb C-941 could be used. Different amounts of carbon, from 0.01 to 0.5× weight can be used. The carbon can be eliminated. Different amounts of Celite, from 0.01 to 0.5× weight can be used. Crystallization: Different amounts of water, including 5 volumes to 50 volumes can be used. The crystallization can also proceed without the addition of seeds. Different water addition times and final hold times can be used. Different wash procedures can be used. Drying: A temperature range of 10 to 60° C. could be used for drying. Catalysts: Different metal and ligand combination could be used. Examples of metal/ligand combinations can be found in Maluenda, Irene; Navarro, Oscar, *Molecules,* 2015, 20, 7528. Various catalysts can be including: XPhos-3G (cas #1445085-55-1); cataCXium® A Pd 3G (CAS #1651823-59-4); PdCl$_2$(DtBPF) (CAS #95408-45-0); SPhos 3G (Cas #1445085-82-4); AmPhos 3G (Cas #1820817-64-8); PCy$_3$ 3G (Cas #1445086-12-3); Pd PEPPSI IPent Cas #1158652-41-5); Pd(PPh$_3$)$_2$Cl$_2$ (Cas #13965-03-2). Examples of catalyst systems that have been demonstrated to afford Compound 1 are listed below in Table 4 using boronic esters 2 or 7 in coupling to 3.

TABLE 4

Catalyst screen summary

| | Conversion to Product at t = 3 h | |
|---|---|---|
| Solvent_Ligand | HB071 | HB075 |
| THF_XPhos 3G | 79.7 | 88.8 |
| THF_CataCXium A 3G | 80.8 | 83.8 |
| THF_PdCl2(DtBPF) | 89.8 | 86.4 |
| THF_SPhos 3G | 71.5 | 88.7 |
| THF_APhos 3G | 83.8 | 85.2 |
| THF_PCy3 3G | 70.0 | 55.2 |
| THF_Pd PEPPSI IPent | 62.2 | 81.9 |
| THF_Pd(PPh3)2Cl2 | 74.8 | 82.5 |
| 2-MeTHF_XPhos 3G | 92.1 | 81.3 |
| 2-MeTHF_CataCXium A 3G | 89.8 | 87.6 |
| 2-MeTHF_PdCl2(DtBPF) | 89.3 | 86.7 |
| 2-MeTHF_SPhos 3G | 86.3 | 88.5 |
| 2-MeTHF_APhos 3G | 90.9 | 86.5 |
| 2-MeTHF_PCy3 3G | 78.6 | 69.8 |
| 2-MeTHP_Pd PEPPSI IPent | 74.6 | 61.7 |
| 2-MeTHF_Pd(PPh3)2Cl2 | 77.9 | 88.7 |
| MeCN_XPhos 3G | 95.5 | 84.1 |
| MeCN_CataCXium A 3G | 78.5 | 69.5 |
| MeCN_PCl2(DtBPF) | 91.6 | 85.3 |
| MeCN_SPhos 3G | 92.6 | 85.8 |
| MeCN_APhos 3G | 88.3 | 88.3 |
| MeCN_PCy3 3G | 86.8 | 35.3 |
| MeCN_Pd PEPPSI IPent | 87.4 | 90.5 |
| MeCN_Pd(PPh3)2Cl2 | 86.5 | 90.6 |

VI. Purification of Compound 1 (CC-90010) by Crystallization from Formic Acid and Water Described herein are methods of purifying Compound 1 by crystallization from formic acid and water. Also described are methods for obtaining three different polymorphs of Compound 1, including the most stable form, Form 1 and two metastable forms, Form 4 The crystallization can also proceed without the addition of seeds. Different water addition times and final hold times can be used. Different wash procedures can be used, Drying: A temperature range of 10 to 60° C. could be used for drying, Catalysts: Different metal and ligand combination could be used. Examples of metal/ligand combinations can be found in Maluenda, Irene; Navarro, Oscar, *Molecules,* 2015, 20, 7528. Various catalysts can be including: XPhos-30 (cas #1445085-55-1); cataCXium® A Pd 3G (CAS #1651823-59-4); PdCl$_2$(DtBPF) (CAS #95408-45-0); SPhos 3G (Cast 1445085-82-4); AmPhos 36 (Cas #1820817-64-8); PCy$_3$ 30 (Cas #1445086-12-3); Pd. PEPPSI Went Cas #1158652-41-5); Pd(PPh$_3$)$_2$Cl$_2$ (Cas #13965-03-2). Examples of catalyst systems that have been demonstrated to afford Compound 1 are listed below in Table 4 using boronic esters 2 or 7 in coupling to 3.

TABLE 4

Catalyst screen summary

| | Conversion to Product at t = 3 h | |
|---|---|---|
| Solvent_Ligand | HB071 | HB075 |
| THF_XPhos 3G | 79.7 | 88.5 |
| THF_CataCXium A 3G | 80.8 | 85.8 |
| THF_PdCl2(DtBPF) | 89.8 | 86.4 |
| THF_SPhos 3G | 71.5 | 85.7 |
| THF_APhos 3G | 83.8 | 85.3 |
| THF_PCy3 3G | 70.0 | 55.2 |
| THF_Pd PEPPSI IPent | 62.2 | 51.9 |
| THF_Pd(PPh3)2Cl2 | 74.8 | 32.9 |
| 2-MeTHF_XPhos 3G | 92.1 | 81.3 |
| 2-MeTHF_CataCXium A 3G | 89.8 | 87.5 |
| 2-MeTHF_PdCl2(DtBPF) | 89.3 | 86.7 |
| 2-MeTHF_5Phos 3G | 86.3 | 85.5 |
| 2-MeTHF_APhos 3G | 90.9 | 86.9 |
| 2-MeTHF_PCy3 3G | 78.6 | 69.8 |
| 2-MeTHF_Pd PEPPSI IPent | 74.6 | 61.7 |
| 2-MeTHF_Pd(PPh3)2Cl2 | 77.9 | 38.7 |
| MeCN_XPhos 3G | 95.5 | 84.1 |
| MeCN_CataCXium A 3G | 78.5 | 69.8 |
| MeCN_PdCl2(DtBPF) | 91.6 | 85.3 |
| MeCN_SPhos 3G | 92.6 | 85.9 |
| MeCN_APhos 3G | 88.3 | 89.3 |
| MeCN_PCy3 3G | 86.8 | 35.3 |
| MeCN_Pd PEPPSI IPent | 87.4 | 90.5 |
| MeCN_Pd(PPh3)2Cl2 | 86.5 | 90.6 |

HB071

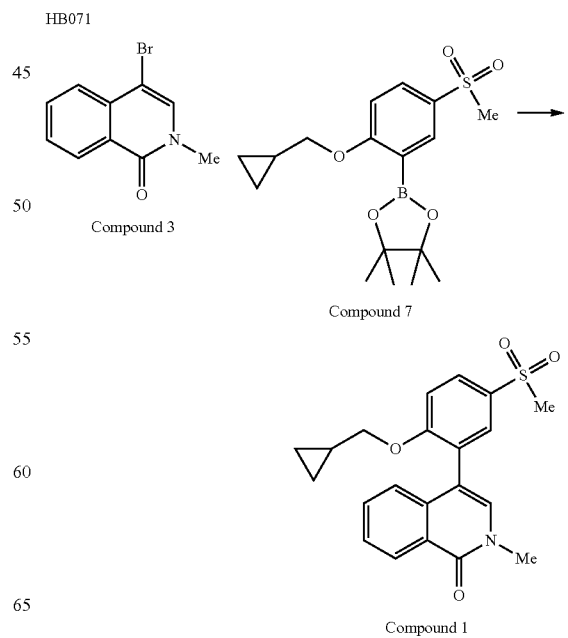

Compound 3

Compound 7

Compound 1

TABLE 4-continued

Catalyst screen summary

| | Conversion to Product at t = 3 h | |
|---|---|---|
| Solvent_Ligand | HB071 | HB075 |
| HB075 | | |

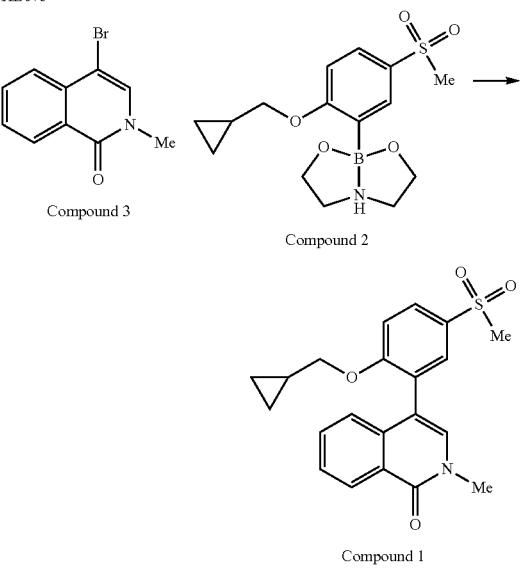

Compound 3

Compound 2

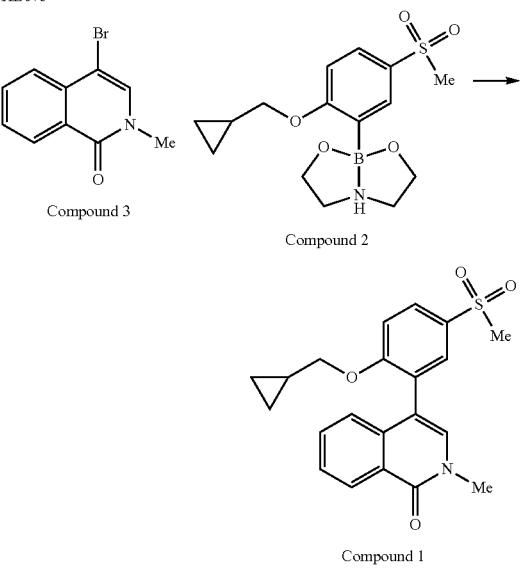

Compound 1

VI. Purification of Compound 1 (CC-90010) by Crystallization from Formic Acid and Water Described herein are methods of purifying Compound 1 by crystallization from formic acid and water. Also described are methods for obtaining three different polymorphs of Compound 1, including the most stable form, Form 1 and two metastable forms, Form 4 and Form 5. Supporting data (XRPD, DSC, photomicroscopy) for all three forms is provided in the examples below.

The structure of Compound 1 (CC-90010) is shown below:

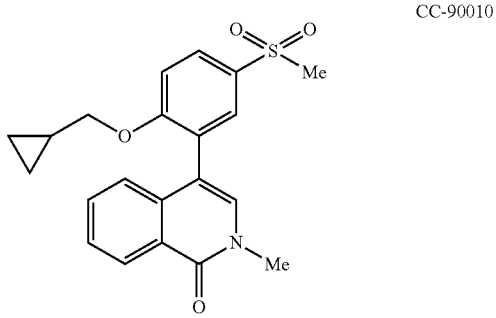 [SMILES: Cn1cc(-c2cc(S(C)(=O)=O)ccc2OCC2CC2)c2ccccc2c1=O]

CC-90010

Crystallization is the primary technique for isolating active pharmaceutical ingredients. A crystallization should be purifying and should result in control of the polymorph. This process discussed describes a method for crystallizing the most stable known form of Compound 1 (CC-90010) from formic acid and water. It also describes methods for isolating two metastable forms.

In particular, described are methods for purifying Compound 1 (CC-90010) from formic acid and water, a system never before used. By varying the solvent composition, addition rates, and drying, different polymorphs can be obtained.

The initial isolation process for final Compound 1 (CC-90010), Form 1, involves using 39 volumes of two ICH class II solvents, methanol and tetrahydrofuran, and a number of distillations which add to the complexity of the process. The process is unseeded, thereby relying on a stochastic formation of solids, which does not allow for control of polymorph or physical attributes.

Four processes are described below. All use only formic acid, an ICH class III solvent, and water. The two processes to Form 1 (most stable polymorph) both control the polymorph by seeding with Form 1, and are more volumetrically efficient (14 to 16× vol). A process to form (metastable) Form 4, and process to form (metastable) Form 5, are also provided. For all of the methods described, the solvent ratios can be changed, the temperature can be changed, the seed amount can be changed, the wash compositions and amounts can be changed, and the drying temperature can be changed.

Process 1 (for Form 1): Compound 1 (1.0× wt) and formic acid (7.0× vol) are charged to Reactor 1. This mixture is agitated and then transferred to reactor 2 via a polish filter. Formic acid (1.0× vol) is charged to reactor 1 then transferred through the same polish filter to Reactor 2. Water (2.2× vol) is charged via a separate polish filter to Reactor 2 over 1 hour. Compound 1 seeds (1% wt, Form 1) are charged and the batch is held at about 20° C. to about 25° C. (or any temperature in between and including these two values, such as about 20, about 21, about 22, about 23, about 24, or about 25° C.). Water (4.8× vol) is charged to reactor 2 via a polish filter in three separate charges (0.25, 0.60, and 3.95× vol). Each charge is added over 1 hour, with a 1 hour hold between charges. After all three charges, the batch is held for at least one hour. A batch temperature of about 20° C. to about 25° C. (or any temperature in between and including these two values, such as about 20, about 21, about 22, about 23, about 24, or about 25° C.) is maintained for all charges.

The batch is filtered, washed twice with polish filtered formic acid and water (1.5× vol formic acid+1.5× vol water each), twice with polish filtered water (3× vol each), and dried under reduced pressure at about 35° C. to about 45° C. (or any temperature in between and including these two values, such as about 35, about 36, about 37, about 38, about 39, about 40, about 41, about 42, about 43, about 44, or about 45° C.).

Process 2 (for Form 1): Compound 1 (CC-90010) (1.0× wt) is charged to formic acid (5.0× vol) in Reactor 1 and agitated at 20° C. to 30° C. (or any temperature in between and including these two values, such as about 20, about 21, about 22, about 23, about 24, about 25, about 26, about 27, about 28, about 29, or about 30° C.) until dissolved. Polish filtered formic acid (2.0× vol) and polish filtered water (1.8× vol) are charged to Reactor 2 and agitated at about 20° C. to about 30° C. (or any temperature in between and including these two values, such as about 20, about 21, about 22, about 23, about 24, about 25, about 26, about 27, about 28, about 29, or about 30° C.). Compound 1 (CC-90010) seeds (Form 1, 0.02 to 0.04× wt) are charged to Reactor 2, and the resulting slurry is agitated for at least 60 minutes.

The Compound 1 (CC-90010)/formic acid solution in Reactor 1 and water (4.4× vol) are then simultaneously charged via polish filters to the seed bed slurry in Reactor 2 over 6 to 10 hours (or any time period in between and including these two values, such as about 6, about 6.5, about 7, about 7.5, about 8, about 8.5, about 9, about 9.5, or about 10 hrs) while maintaining a temperature of about 20° C. to about 30° C. (or any temperature in between and including these two values, such as about 20, about 21, about 22, about 23, about 24, about 25, about 26, about 27, about 28, about 29, or about 30° C.). After the addition, formic acid (1× vol) is charged to Reactor 1. The formic acid rinse in Reactor 1 and water (0.9× vol) are simultaneously charged via polish filters to the batch in Reactor 2 over at least about 15 minutes while maintaining a temperature of about 20° C. to about 30° C. (or any temperature in between and including these two values, such as about 20, about 21, about 22, about 23, about 24, about 25, about 26, about 27, about 28, about 29, or about 30° C.).

Process for Form 4: Compound 1 (CC-90010) (1.0× wt) is charged to a reaction flask followed by formic acid (8.0× vol) and water 2.2× vol). A small amount of Form 1 seeds are charged and this mixture is agitated at about 20° C. to about 25° C. (or any temperature in between and including these two values, such as about 20, about 21, about 22, about 23, about 24, or about 25° C.) for about 2 hours or for any suitable time period. The slurry is filtered and the wet cake is not dried.

Process for Form 5: Compound 1 (CC-90010) (1.0× wt) is charged to the reaction flask followed by formic acid (8.0× vol) and water 2.2× vol). This mixture is agitated at about 15° C. (or at any suitable temperature) for about 4 hours (or for any suitable time period). The slurry is filtered and the wet cake is not dried. The batch is filtered, washed twice with polish filtered formic acid and water (1.5× vol formic acid+1.5× vol water each), twice with polish filtered water (3× vol each), and dried under reduced pressure at about 35° C. to about 45° C. (or any temperature in between and including these two values, such as about 35, about 36, about 37, about 38, about 39 or about 40° C.).

VI. Definitions

The following definitions are provided to facilitate understanding of certain terms used throughout this specification.

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Thus, unless context indicates otherwise, the word "or" means any one member of a particular list and also includes any combination of members of that list. Other than in the operating examples, or where otherwise indicated, all numbers expressing quantities of ingredients or reaction conditions used herein should be understood as modified in all instances by the term "about."

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims. In order that the present disclosure can be more readily understood, certain terms are first defined. Additional definitions are set forth throughout the detailed description.

The bromodomain inhibitor compound described herein (i.e., Compound 1) is a bromodomain 4 (BRD4) inhibitor. In preliminary in vitro studies, BRD4 inhibition was observed, in addition to other cancer-related inhibitory activity, in several different cell lines (Raji, human Burkitts lymphoma cells; HL-60, human proleukemia cells; and NCI-H460, human non-small cell lung cancer cells). See U.S. Pat. No. 9,034,900.

In the context of the present embodiments, 4-[2 (cyclopropylmethoxy)-S-methylsulfonylphenyl]-2-methylisoquinolin-1-one or Compound 1 and the like, includes crystalline forms, amorphous forms, solvates, hydrates, and pharmaceutically acceptable salts thereof, unless the context requires specificity (e.g., "Form 1"); as well as pharmaceutical compositions that include this compound. Unless otherwise stated, structures depicted herein are intended to include compounds that differ only in the presence of one or more isotopically enriched atoms or unnatural proportions of atomic isotopes at one or more atoms that constitute such compounds.

All numerical designations, e.g., pH, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art.

"FIO" refers to "for information only."

"HPLC" refers to high-performance liquid chromatography.

"IPC" refers to "in process control."

"NMR" refers to nuclear magnetic resonance.

"NMT" refers to "not more than."

As used herein, $C_{m-n}$, such as $C_{1-12}$, $C_{1-8}$, or $C_{1-6}$ when used before a group refers to that group containing m to n carbon atoms.

"Optionally substituted" refers to a group selected from that group and a substituted form of that group. Substituents may include any of the groups defined below. In one embodiment, substituents are selected from $C_1$-$C_{10}$ or $C_1$-$C_6$ alkyl, substituted $C_1$-$C_{10}$ or $C_1$-$C_6$ alkyl, $C_2$-$C_6$ alkenyl, $C_2$-$C_6$ alkynyl, $C_6$-$C_{10}$ aryl, $C_3$-$C_8$ cycloalkyl, $C_2$-$C_{10}$ heterocyclyl, $C_1$-$C_{10}$ heteroaryl, substituted $C_2$-$C_6$ alkenyl, substituted $C_2$-$C_6$ alkynyl, substituted $C_6$-$C_{10}$ aryl, substituted C3-C8 cycloalkyl, substituted $C_2$-$C_{10}$ heterocyclyl, substituted $C_1$-$C_{10}$ heteroaryl, halo, nitro, cyano, —$CO_2H$ or a $C_1$-$C_6$ alkyl ester thereof.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH3)(CH3CH2)CH$—), t-butyl (($CH3)3C$—), n-pentyl ($CH_3CH_2CH_2CH_2CH_2$), and neopentyl (($CH_3)_3CCH_2$—).

"Alkenyl" refers to monovalent straight or branched hydrocarbyl groups having from 2 to 10 carbon atoms and preferably 2 to 6 carbon atoms or preferably 2 to 4 carbon atoms and having at least 1 and preferably from 1 to 2 sites of vinyl (>C=C<) unsaturation. Such groups are exemplified, for example, by vinyl, allyl, and but 3 en 1 yl. Included within this term are the cis and trans isomers or mixtures of these isomers.

"Alkynyl" refers to straight or branched monovalent hydrocarbyl groups having from 2 to 10 carbon atoms and preferably 2 to 6 carbon atoms or preferably 2 to 3 carbon atoms and having at least 1 and preferably from 1 to 2 sites of acetylenic unsaturation. Examples of such alkynyl groups include acetylenyl (—C≡CH—), and propargyl (—CH2C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Heteroalkyl" refers to an alkyl group one or more carbons is replaced with —O—, —S—, $SO_2$, a P containing moiety as provided herein, —$NR^Q$—,

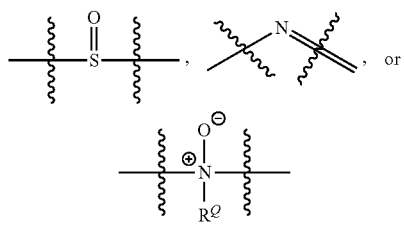

moieties where $R^Q$ is H or $C_1$-$C_6$ alkyl. Substituted heteroalkyl refers to a heteroalkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxyl, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to a vinyl (unsaturated) carbon atom.

"Heteroalkenyl" refers to an alkenyl group one or more carbons is replaced with —O—, —S—, $SO_2$, a P containing moiety as provided herein, —NRQ-,

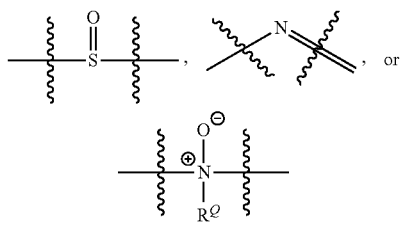

moieties where $R^Q$ is H or $C_1$-$C_6$ alkyl. Substituted heteroalkenyl refers to a heteroalkenyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO3H, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Heteroalkynyl" refers to an alkynyl group one or more carbons is replaced with —O—, —S—, SO$_2$, a P containing moiety as provided herein, —NRQ-,

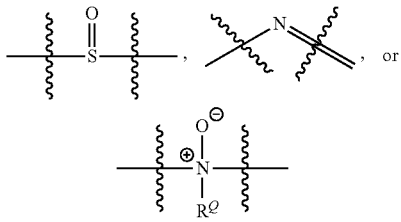

moieties where $R^Q$ is H or $C_1$-$C_6$ alkyl. Substituted heteroalkynyl refers to a heteroalkynyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Alkylene" refers to divalent saturated aliphatic hydrocarbyl groups having from 1 to 10 carbon atoms, preferably having from 1 to 6 and more preferably 1 to 3 carbon atoms that are either straight chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)— or —CH(CH$_3$)CH$_2$—), butylene (—CH$_2$CH$_2$CH$_2$CH$_2$—), isobutylene (—CH$_2$CH(CH$_3$—)CH$_2$—), sec-butylene (—CH$_2$CH$_2$(CH$_3$—)CH—), and the like. Similarly, "alkenylene" and "alkynylene" refer to an alkylene moiety containing respective 1 or 2 carbon carbon double bonds or a carbon carbon triple bond.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some embodiments, the alkylene has 1 to 2 of the aforementioned groups, or having from 1-3 carbon atoms replaced with —O—, —S—, or —NRQ- moieties where $R^Q$ is H or $C_1$-$C_6$ alkyl. It is to be noted that when the alkylene is substituted by an oxo group, 2 hydrogens attached to the same carbon of the alkylene group are replaced by "=O". "Substituted alkenylene" and "substituted alkynylene" refer to alkenylene and substituted alkynylene moieties substituted with substituents as described for substituted alkylene.

"Alkynylene" refers to straight or branched divalent hydrocarbyl groups having from 2 to 10 carbon atoms and preferably 2 to 6 carbon atoms or preferably 2 to 3 carbon atoms and having at least 1 and preferably from 1 to 2 sites of acetylenic (—C≡C—) unsaturation. Examples of such alkynylene groups include C≡C— and CH$_2$C≡C—.

"Substituted alkynylene" refers to alkynylene groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Heteroalkylene" refers to an alkylene group wherein one or more carbons is replaced with —O—, —S—, $SO_2$, a P containing moiety as provided herein, —$NR^Q$—,

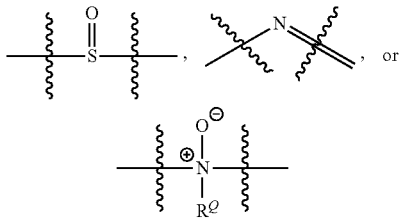

moieties where $R^Q$ is H or $C_1$-$C_6$ alkyl. "Substituted heteroalkylene" refers to heteroalkynylene groups having from 1 to 3 substituents, and preferably 1 to 2 substituents, selected from the substituents disclosed for substituted alkylene.

"Heteroalkenylene" refers to an alkenylene group wherein one or more carbons is replaced with —O—, —S—, $SO_2$, a P containing moiety as provided herein, —$NR^Q$—,

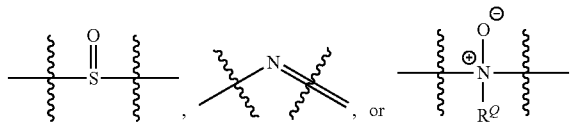

moieties where $R^Q$ is H or $C_1$-$C_6$ alkyl. "Substituted heteroalkenylene" refers to heteroalkynylene groups having from 1 to 3 substituents, and preferably 1 to 2 substituents, selected from the substituents disclosed for substituted alkenylene.

"Heteroalkynylene" refers to an alkynylene group wherein one or more carbons is replaced with —O—, —S—, $SO_2$, a P containing moiety as provided herein, —$NR^Q$—,

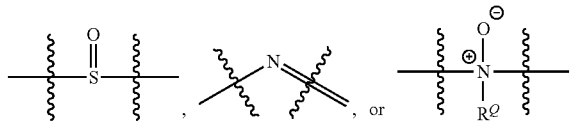

moieties where $R^Q$ is H or $C_1$-$C_6$ alkyl. "Substituted heteroalkynylene" refers to heteroalkynylene groups having from 1 to 3 substituents, and preferably 1 to 2 substituents, selected from the substituents disclosed for substituted alkynylene.

"Alkoxy" refers to the group O alkyl wherein alkyl is defined herein. Alkoxy includes, by way of example, methoxy, ethoxy, n propoxy, isopropoxy, n butoxy, t butoxy, sec butoxy, and n pentoxy.

"Substituted alkoxy" refers to the group O (substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{47}$C(O)alkyl, —$NR^{47}$C(O)substituted alkyl, —$NR^{47}$C(O)cycloalkyl, —$NR^{47}$C(O)substituted cycloalkyl, —$NR^{47}$C(O)cycloalkenyl, —$NR^{47}$C(O)substituted cycloalkenyl, —$NR^{47}$C(O)alkenyl, —$NR^{47}$C(O)substituted alkenyl, —$NR^{47}$C(O)alkynyl, —$NR^{47}$C(O)substituted alkynyl, —$NR^{47}$C(O)aryl, —$NR^{47}$C(O)substituted aryl, —$NR^{47}$C(O)heteroaryl, —$NR^{47}$C(O)substituted heteroaryl, —$NR^{47}$C(O)heterocyclic, and $NR^{47}$C(O)substituted heterocyclic wherein $R^{47}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group $NH_2$.

"Substituted amino" refers to the group —$NR^{48}R^{49}$ where $R^{48}$ and $R^{49}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, $SO_2$ alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{48}$ and $R^{49}$ are optionally joined, together with the nitrogen bound thereto to form a heterocyclic or substituted heterocyclic group, provided that $R^{48}$ and $R^{49}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^{48}$ is hydrogen and $R^{49}$ is alkyl, the substituted amino group is sometimes referred to herein as alkylamino. When $R^{48}$ and $R^{49}$ are alkyl, the substituted amino group is referred to herein as dialkylamino. When referring to a monosubstituted amino, it is meant that either $R^{48}$ or $R^{49}$ is hydrogen but not both. When referring to a disubstituted amino, it is meant that neither $R^{48}$ nor $R^{49}$ are hydrogen.

"Aminocarbonyl" refers to the group —C(O)NR$^{50}$R$^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)NR$^{50}$R$^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{47}$C(O)NR$^{50}$R$^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —NR$^{47}$C(S)NR$^{50}$R$^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —O—C(O)NR$^{50}$R$^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —SO$_2$NR$^{50}$R$^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group —O—SO$_2$NR$^{50}$R$^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^{47}$SO$_2$NR$^{50}$R$^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^{52}$)NR$^{50}$R$^{51}$ where $R^{50}$, $R^{51}$, and $R^{52}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2 benzoxazolinone, 2H 1,4 benzoxazin 3(4H) one 7 yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Arylene" refers to a divalent aromatic carbocyclic group of from 6 to 14 carbon atoms having a single ring or multiple condensed rings. "Substituted arylene" refers to an arylene having from 1 to 5, preferably 1 to 3, or more preferably 1 to 2 substituents as defined for aryl groups.

"Heteroarylene" refers to a divalent aromatic group of from 1 to 10 carbon atoms and 1 to 4 heteroatoms selected from the group consisting of oxygen, nitrogen and sulfur within the ring. "Substituted heteroarylene" refers to heteroarylene groups that are substituted with from 1 to 5, preferably 1 to 3, or more preferably 1 to 2 substituents selected from the group consisting of the same group of substituents defined for substituted aryl.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group S (substituted aryl), where substituted aryl is as defined herein.

"Carbonyl" refers to the divalent group —C(O)— which is equivalent to —C(=O)—.

"Carboxyl" or "carboxy" refers to COOH or salts thereof.

"Carboxyl ester" or "carboxy ester" refers to the group —C(O)(O)-alkyl, —C(O)(O)-substituted alkyl, —C(O)O-alkenyl, —C(O)(O)-substituted alkenyl, —C(O)(O)-alkynyl, —C(O)(O)-substituted alkynyl, —C(O)(O)-aryl, —C(O)(O)-substituted-aryl, —C(O)(O)-cycloalkyl, —C(O)(O)-substituted cycloalkyl, —C(O)(O)-cycloalkenyl, —C(O)(O)-substituted cycloalkenyl, —C(O)(O)-heteroaryl, —C(O)(O)-substituted heteroaryl, —C(O)(O)-heterocyclic, and —C(O)(O)-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino refers to the group —NR$^{47}$C(O)(O)-alkyl, —NR$^{47}$C(O)(O)-substituted alkyl, —NR$^{47}$C(O)O-alkenyl, —NR$^{47}$C(O)(O)-substituted alkenyl, —NR$^{47}$C(O)(O)-alkynyl, —NR$^{47}$C(O)(O)-substituted alkynyl, —NR$^{47}$C(O)(O)-aryl, —NR$^{47}$C(O)(O)-substituted-aryl, —NR$^{47}$C(O)(O)-cycloalkyl, —NR$^{47}$C(O)(O)-substituted cycloalkyl, —NR$^{47}$C(O)(O)-cycloalkenyl, —NR$^{47}$C(O)(O)-substituted cycloalkenyl, —NR$^{47}$C(O)(O)-heteroaryl, —NR$^{47}$C(O)(O)-substituted heteroaryl, —NR$^{47}$C(O)(O)-heterocyclic, and —NR$^{47}$C(O)(O)-substituted heterocyclic wherein R$^{47}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)(O)-substituted alkynyl, —O—C(O)O-aryl, —O—C(O)O-substituted-aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group CN.

"Cycloalkyl" refers to cyclic alkyl groups of from 3 to 10 carbon atoms having single or multiple cyclic rings including fused, bridged, and spiro ring systems. The fused ring can be an aryl ring provided that the non aryl part is joined to the rest of the molecule. Examples of suitable cycloalkyl groups include, for instance, adamantyl, cyclopropyl, cyclobutyl, cyclopentyl, and cyclooctyl.

"Cycloalkenyl" refers to non aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, substituted sulfonyloxy, thioacyl, thiol, alkylthio, and substituted alkylthio, wherein said substituents are as defined herein.

"Cyclopropano" refers to:

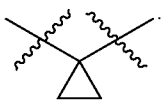 [SMILES: *C1(*)CC1]

"Cyclobutano" refers to:

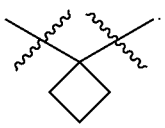 [SMILES: *C1(*)CCC1]

"Cycloalkyloxy" refers to —O-cycloalkyl.
"Substituted cycloalkyloxy refers to —O-(substituted cycloalkyl).
"Cycloalkylthio" refers to —S-cycloalkyl.
"Substituted cycloalkylthio" refers to —S-(substituted cycloalkyl).
"Cycloalkenyloxy" refers to —O-cycloalkenyl.
"Substituted cycloalkenyloxy" refers to —O-(substituted cycloalkenyl).
"Cycloalkenylthio" refers to —S-cycloalkenyl.
"Substituted cycloalkenylthio" refers to —S-(substituted cycloalkenyl).
"Guanidino" refers to the group —NHC(=NH)NH₂.
"Substituted guanidino" refers to —NR⁵³C(=NR⁵³)N(R⁵³)₂ where each R⁵³ is independently selected from the group consisting of hydrogen, alkyl, substituted alkyl, aryl, substituted aryl, heteroaryl, substituted heteroaryl, cycloalkyl, substituted cycloalkyl, heterocyclic, and substituted heterocyclic and two R⁵³ groups attached to a common guanidino nitrogen atom are optionally joined together with the nitrogen bound thereto to form a heterocyclic or substituted heterocyclic group, provided that at least one R⁵³ is not hydrogen, and wherein said substituents are as defined herein.
"Halo" or "halogen" refers to fluoro, chloro, bromo and iodo.
"Hydroxy" or "hydroxyl" refers to the group —OH.
"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N oxide (N→O), sulfinyl, or sulfonyl moieties. Certain non-limiting examples include pyridinyl, pyrrolyl, indolyl, thiophenyl, oxazolyl, thizolyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.
"Heteroaryloxy" refers to —O-heteroaryl.
"Substituted heteroaryloxy" refers to the group —O-(substituted heteroaryl).
"Heteroarylthio" refers to the group —S-heteroaryl.
"Substituted heteroarylthio" refers to the group —S-(substituted heteroaryl).
"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more of the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N oxide, sulfinyl, or sulfonyl moieties.
"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.
"Heterocyclyloxy" refers to the group —O-heterocycyl.
"Substituted heterocyclyloxy" refers to the group —O-(substituted heterocycyl).
"Heterocyclylthio" refers to the group —S-heterocycyl.
"Substituted heterocyclylthio" refers to the group —S-(substituted heterocycyl).
Examples of heterocycle and heteroaryls include, but are not limited to, azetidine, pyrrole, furan, thiophene, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4 tetrahydroisoquinoline, 4,5,6,7 tetrahydrobenzo[b]thiophene, thiazole, thiazolidine, thiophene, benzo[b]thiophene, morpholinyl, thiomorpholinyl (also referred to as thiamorpholinyl), 1,1 dioxothiomorpholinyl, piperidinyl, pyrrolidine, and tetrahydrofuranyl.
"Nitro" refers to the group —NO₂.
"Oxo" refers to the atom (=O).
Phenylene refers to a divalent aryl ring, where the ring contains 6 carbon atoms.
Substituted phenylene refers to phenylenes which are substituted with 1 to 4, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Spirocycloalkyl" and "spiro ring systems" refers to divalent cyclic groups from 3 to 10 carbon atoms having a cycloalkyl or heterocycloalkyl ring with a spiro union (the union formed by a single atom which is the only common member of the rings) as exemplified by the following structure:

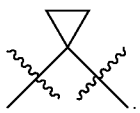 [SMILES: *C1(*)CC1]

"Sulfonyl" refers to the divalent group —$S(O)_2$—.

"Substituted sulfonyl" refers to the group —$SO_2$-alkyl, —$SO_2$-substituted alkyl, —$SO_2$-alkenyl, —$SO_2$-substituted alkenyl, 502-cycloalkyl, —$SO_2$-substituted cycloalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl —$SO_2$—, phenyl —$SO_2$—, and 4-methylphenyl-$SO_2$—.

"Substituted sulfonyloxy" refers to the group —$OSO_2$-alkyl, —$OSO_2$-substituted alkyl, —$OSO_2$-alkenyl, —$OSO_2$-substituted alkenyl, $OSO_2$-cycloalkyl, —$OSO_2$-substituted cycloalkyl, —$OSO_2$-cycloalkenyl, —$OSO_2$-substituted cylcoalkenyl, —$OSO_2$-aryl, —$OSO_2$-substituted aryl, —$OSO_2$-heteroaryl, —$OSO_2$-substituted heteroaryl, —$OSO_2$-heterocyclic, —$OSO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group SH.

"Thiocarbonyl" refers to the divalent group —C(S)— which is equivalent to —C(=S)—.

"Thioxo" refers to the atom (=S).

"Alkylthio" refers to the group S-alkyl wherein alkyl is as defined herein.

"Substituted alkylthio" refers to the group —S-(substituted alkyl) wherein substituted alkyl is as defined herein.

A substituted ring can be substituted with one or more fused and/or spiro cycles. Such fused cycles include a fused cycloalkyl, a fused heterocyclyl, a fused aryl, a fused heteroaryl ring, each of which rings can be unsubstituted or substituted. Such spiro cycles include a fused cycloalkyl and a fused heterocyclyl, each of which rings can be unsubstituted or substituted.

It is understood that the above definitions are not intended to include impermissible substitution patterns (e.g., methyl substituted with 5 fluoro groups). Such impermissible substitution patterns are well known to the skilled artisan.

It is understood that the above definitions are not intended to include impermissible substitution patterns (e.g., methyl substituted with 5 fluoro groups). Such impermissible substitution patterns are well known to the skilled artisan.

"Pharmaceutically acceptable salt" refers to salts of a compound, which salts are suitable for pharmaceutical use and are derived from a variety of organic and inorganic counter ions well known in the art and include, when the compound contains an acidic functionality, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate (see Stahl and Wermuth, eds., "Handbook of Pharmaceutically Acceptable Salts," (2002), Verlag Helvetica Chimica Acta, Zürich, Switzerland), for a discussion of pharmaceutical salts, their selection, preparation, and use.

Generally, pharmaceutically acceptable salts are those salts that retain substantially one or more of the desired pharmacological activities of the parent compound and which are suitable for in vivo administration. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like.

Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4 chlorobenzenesulfonic acid, 2-naphthalenesulfonic acid, 4-toluenesulfonic acid, camphorsulfonic acid, etc.), glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or by an ammonium ion (e.g., an ammonium ion derived from an organic base, such as, ethanolamine, diethanolamine, triethanolamine, morpholine, piperidine, dimethylamine, diethylamine, triethylamine, and ammonia).

EXAMPLES

The disclosed ingredients, formulations, processes and procedures for practicing the methods disclosed herein may correspond to that described above. Other embodiments and uses will be apparent to one skilled in the art in light of the present disclosures. The following examples are provided merely as illustrative of various embodiments and shall not be construed to limit the invention in any way.

Example 1: Synthesis of Compound 1

Synthesis of compound 1 was accomplished according to Scheme 1 below. Referring to Scheme 1, synthesis commenced with bromination of starting material 4-(methylsulfonyl)phenol 4, to produce compound 5. Compound 5 was O-alkylated with (bromomethyl)cyclopropane to produce compound 6. Boronate Compound 2 was then formed by borylation of Compound 6 with Pd catalyst and bis (pinacolato)diboron to produce transient Compound 7, which was subsequently treated with diethanolamine (DEA) to afford cross-coupling partner Compound 2. Cross-coupling partner Compound 3 was formed in one pot starting from commercially available Compound 8. Compound 8 was N-methylated and brominated to afford Compound 3. Compounds 2 and 3 were cross-coupled (Norio, M. and Suzuki, A., *Chem. Rev.*, 95(7), 2457-2483 (1995)) to afford the target compound 1.

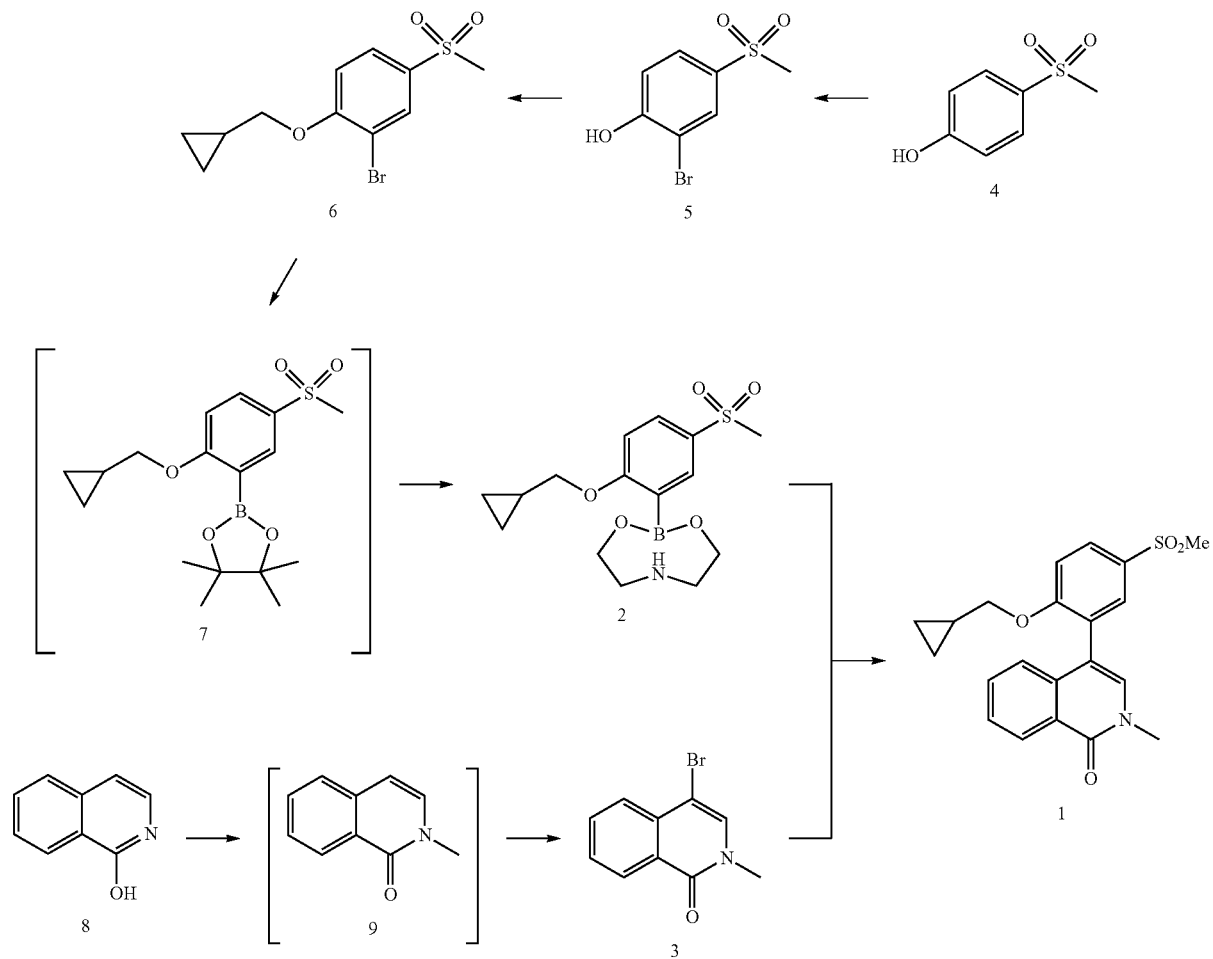

Scheme 1: Synthesis of compound 1

1.1: Bromination of 4

The bromination of Compound 4 to produce Compound 5 itself is simple, however stopping at the mono-brominated Compound 5 was challenging. The bis-brominated Compound 5-a (see Scheme 2 below) is a particularly pernicious impurity as it couples downstream to form a difficult-to-purge impurity.

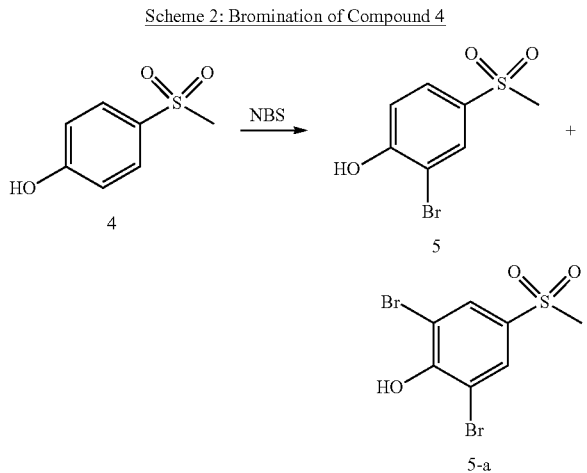

Scheme 2: Bromination of Compound 4

The key to high purity with reasonable yield was to exploit the solubility differences of the starting material Compound 4 (46 mg/ml at 20° C.) and the product Compound 5 (8 mg/ml) in $CH_2Cl_2$. These solubility differences are summarized in Table 3 below.

TABLE 3

| Compound | Solubility in $CH_2Cl_2$, 10° C. | Solubility in $CH_2Cl_2$, 20° C. | Solubility in $CH_2Cl_2$, 30° C. | Solubility in $CH_2Cl_2$, 10% $H_2SO_4$, 10° C. | Solubility in $CH_2Cl_2$, 10% $H_2SO_4$, 20° C. | Solubility in $CH_2Cl_2$, 10% $H_2SO_4$, 30° C. |
|---|---|---|---|---|---|---|
| Compound 4 | 30 mg/ml | 46 mg/ml | 198 mg/ml | 19 mg/ml | 51 mg/ml | 390 mg/ml |
| Compound 5 | 6 mg/ml | 8 mg/ml | 20 mg/ml | 5 mg/ml | 8 mg/ml | 11 mg/ml |
| Compound 5-a diBr | 5 mg/ml | 7 mg/ml | 10 mg/ml | 5 mg/ml | 7 mg/ml | 14 mg/ml |

This solubility difference is exploited by performing the reaction at a high concentration to drive Compound 5 out of solution once formed, thereby minimizing its ability to react further with the brominating reagent to form Compound 5-a diBr. The reaction is seeded with Compound 5 to initiate its crystallization.

Figure 22:
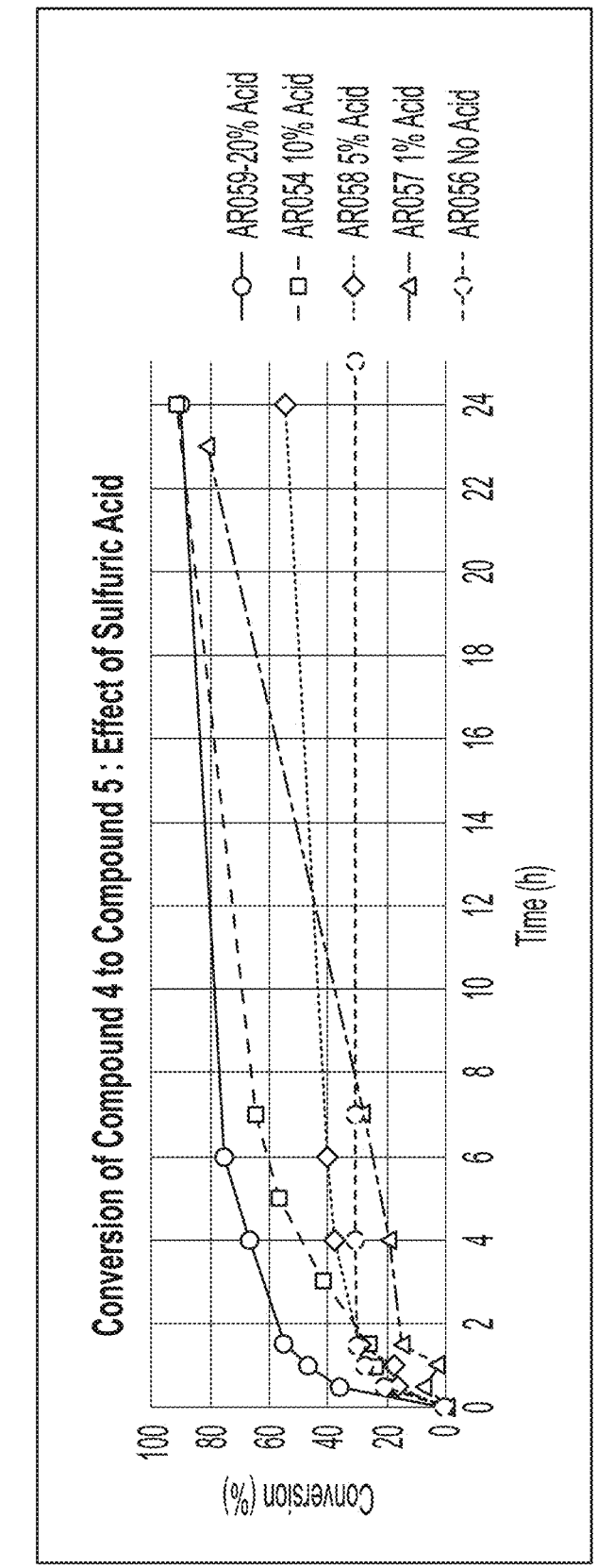
FIG. 22 shows conversion of Compound 4 to Compound 5: Effect of Sulfuric Acid.
Figure 23:
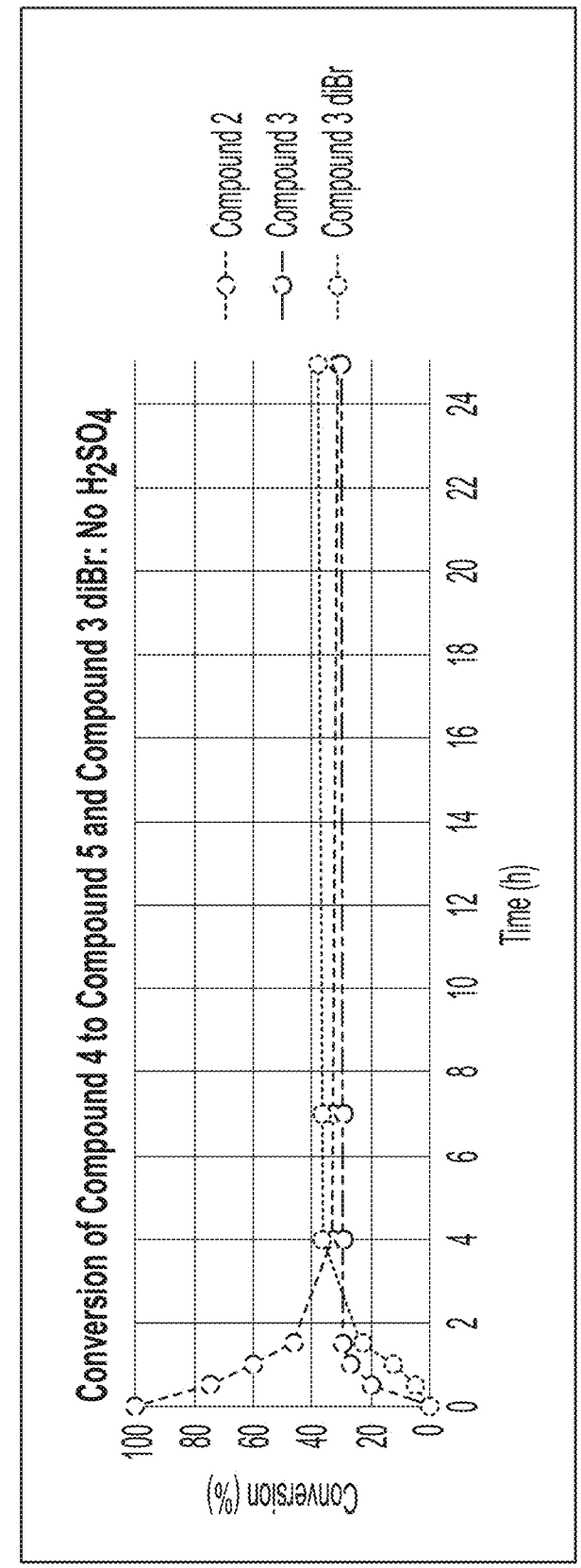
FIG. 23 shows conversion of Compound 5 and Compound 5-a diBr: No $H_2SO_4$.

In FIG. 22 (Conversion of Compound 4 to Compound 5: Effect of Sulfuric Acid) it can be seen that in the absence of acid the initial reaction to Compound 5 is rapid, however the conversion plateaus at about 30% Compound 5. The main side product was found to be the impurity Compound 5-a diBr (see FIG. 23: Conversion of Compound 5 and Compound 5-a diBr: No $H_2SO_4$). Addition of increasing amounts of sulfuric acid leads to a higher conversion to desired Compound 5.

Figure 24:
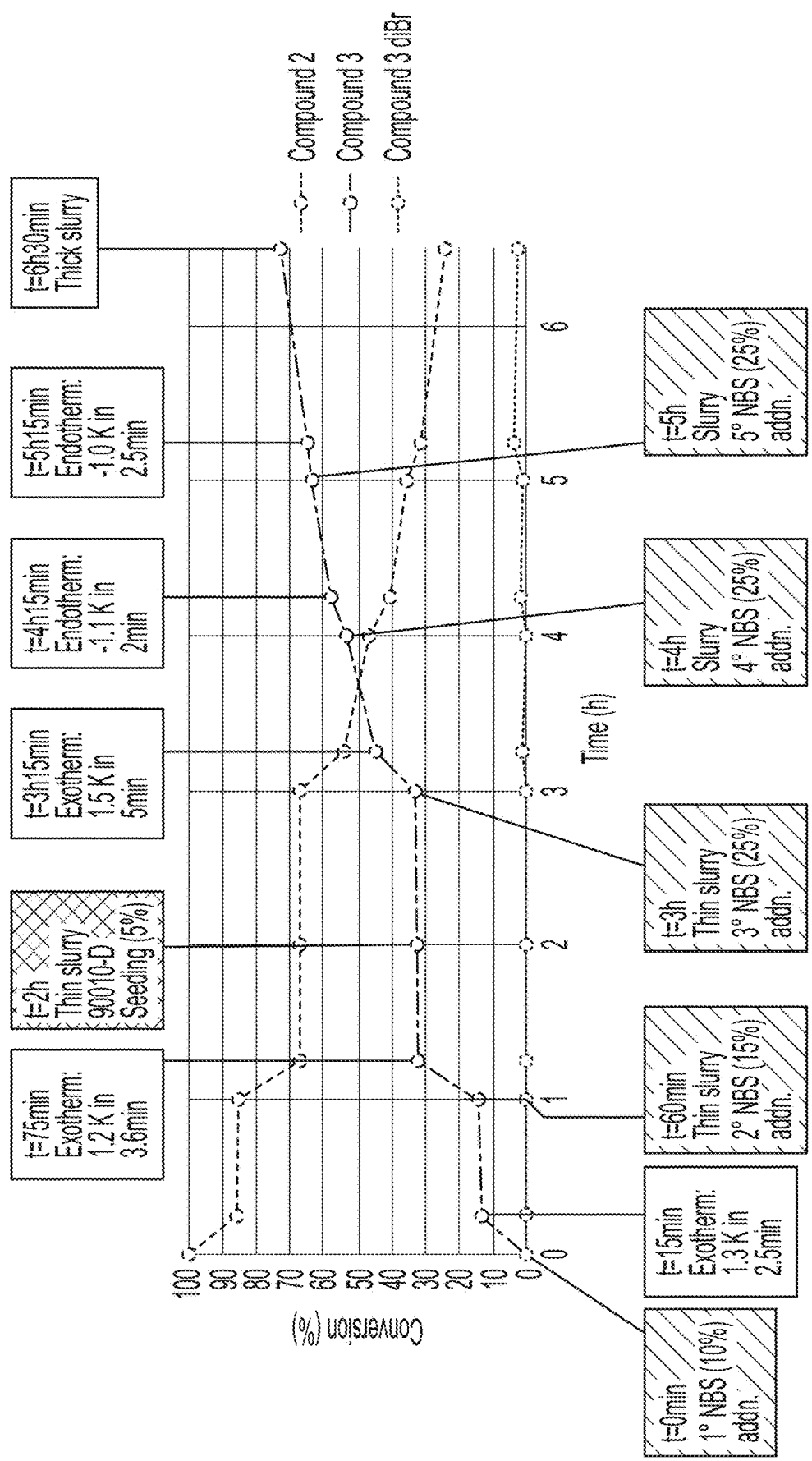
FIG. 24 shows Compound 4 to Compound 5 Reaction Profile: Portion-wise Addition of NBS, Seeding.

FIG. 24 (Compound 4 to Compound 5 Reaction Profile: Portion-wise Addition of NBS, Seeding) depicts further reaction control. The portion-wise addition of NBS after addition of catalytic sulfuric acid minimizes the temperature rise, and the addition of Compound 5 after an initial NBS charge promotes the reactive crystallization of Compound 5. After about 6 to 7 hours of reaction it can be seen that the major product is Compound 5, with only a small (<5%) of the di-brominated impurity formed. In contrast, in a reaction where Compound 4 and all of the NBS were charged followed by the addition of 4 volumes of methylene chloride, a rapid exotherm resulted and undesired Compound 5-a diBr was found to be the major product.

Thus, the reaction was run under a high concentration in $CH_2Cl_2$ with a portion-wise solid addition of NBS (to control both availability of the electrophile and the exotherm). An end of reaction slurry sample typically showed not more than 5% of the starting material Compound 4 remaining. After filtration the crude cake was washed with cold $CH_2Cl_2$ and the $CH_2Cl_2$-washed filter cake contained not more than 0.5% by weight dibrominated Compound 5-a. It also contained a large amount of HPLC-silent succinimide.

The following procedure was carried out: Compound 4 (25 g, 145 mmol) followed by $CH_2Cl_2$ (100 mL) were added to a reaction vessel and agitated. The batch was adjusted to 17° C. to 23° C. Sulfuric acid was charged (2.7 mL, 51 mmol) to the batch maintaining 17° C. to 23° C. The batch was stirred at 17° C. to 23° C. for 10 minutes to 20 minutes. The first portion of N-bromosuccimide (NBS) was charged (6.5 g, 36.5 mmol) to the batch at 17° C. to 23° C. and stirred for at least 30 min. The second portion of NBS was charged (6.5 g, 36.5 mmol) to the batch at 17° C. to 23° C. and stirred for at least 30 min. The batch was seeded with Compound 5 (0.02 wt) and stirred for ca. 30 min at 17° C. to 23° C. to induce crystallization.

The third portion of NBS was charged (6.5 g, 36.5 mmol) to the batch at 17° C. to 23° C. and stirred for at least 30 min. NBS (6.5 g, 36.5 mmol) was charged to the batch at 17° C. to 23° C. and stirred for at least 30 min. Additional $CH_2Cl_2$ was charged (50 mL) to the batch while maintaining 17° C. to 23° C. to aid in agitation and transfer for filtration. The batch was stirred at 17° C. to 23° C. until complete by HPLC analysis (~20-40 h). The product was collected by suction filtration. The filter cake was slurry washed with $CH_2Cl_2$ (3×50 mL) at 17° C. to 23° C. (target 20° C.). The filter cake was slurry washed with purified water (3.0 vol) at 65° C. to 75° C. for 2 to 3 hours. Then, the filter cake was slurry washed with purified water (3×1.0 vol, 3×1.0 wt) at 17° C.

to 23° C. The wet cake was dried under vacuum with nitrogen bleed at 60° C. Yield: 27 g 5 (74% molar)>97% by weight. $^1$H NMR (500 MHz, d6-DMSO) 8.01 (1H, d, $^4$J=2.1 Hz, RO—Ar meta-$\underline{H}$), 7.76 (1H, dd, J=8.6 and $^4$J=2.1 Hz, RO—Ar meta-$\underline{H}$), 7.14 (1H, d, J=8.6 Hz, RO—Ar ortho-$\underline{H}$), 3.38 (1H, br s, O$\underline{H}$), 3.20 (3H, s, C$\underline{H}_3$); MS (ES$^-$) calc. 249/251; found 249/251. Melting point (MP): (DSC) 188° C.

The above procedure allowed for the following modifications. Solvents: Alternative solvents could be used. Examples include chlorinated solvents, such as chloroform or 1,2 dichloroethane, and non-chlorinated solvents such as acetonitrile, tetrahydrofuran, or 2-methyltetrahydrofuran. Reaction concentration: The reaction concentration can be varied from about 2× vol to about 20× vol (with respect to Compound 4). Brominating agents: Additional brominating reagents include bromine and 1,3-dibromo-5,5-dimethylhydantoin. Bromination reagent stoichiometry: Different amounts of the brominating reagent can be used, from about 0.8 equiv to about 1.9 equiv. Bromination reagent addition: The brominating reagent can be added all at once, portion wise in about 2 to about 20 portions, or continuously. The addition times can vary from about 0 to about 72 hours. Temperature: Reaction temperatures from about 0° C. to about 40° C. could be used. Acids: Different acids can be envisioned, including benzenesulfonic acid, para-toluenesulfonic acid, triflic acid, hydrobromic acid, and trifluoroacetic acid. Isolation: Instead of directly filtering the product and washing with methylene chloride and water, at the end of reaction an organic solvent capable of dissolving Compound 5 could be charged, followed by an aqueous workup to remove succinimide, and addition of an antisolvent or solvent exchange to an appropriate solvent to crystallize Compound 4. Drying: A temperature range of about 10 to about 60° C. could be used for drying.

An alternative process to Compound 5 has also been developed. This process is advantageous in that it does not use a chlorinated solvent, and provides additional controls over the formation of the Compound 5-a dibromo impurity. See Oberhauser, T. *J. Org. Chem* 1997, 62, 4504-4506. The process is as follows. Compound 4 (10 g, 58 mmol) and acetonitrile (100 ml) were charged to the reactor and agitated. The batch was cooled to −20° C. Triflic acid (CF$_3$SO$_3$H or TfOH, 5.5 mL, 62 mmol) was charged while maintaining a batch temperature of −10 to −25° C. N-bromosuccinimide was charged (NBS, 11.4 g, 64 mmol), stirred at −10 to −25° C. for 30 minutes, then warmed to 20° C. over 3 to 4 hours. Agitation was continued at 15° C. to 25° C. until reaction completion. If the reaction conversion plateaued before completion, the reaction was cooled to −5 to −15° C., and additional NBS was added, the amount based off of unreacted starting material, followed by warming to 15° C. to 25° C. and reacting until complete.

After reaction completion, the batch was warmed to 40° C. to 50° C. and concentrated under reduced pressure to 40 mL. The batch was cooled to −5° C. to −15° C. and the resulting product solids were filtered off. The solids were slurry washed three times, each with 20 mL water, for at least 15 minutes. The final cake was dried at 50° C. to 60° C. under reduced pressure to furnish 10 g of 5 containing less than 0.1% MeCN, 0.07% water, and 0.1% triflic acid (TfOH) by weight.

Alternatives to the above procedure employing MeCN and TfOH are as follows. Brominating agents: Additional brominating reagents include bromine and 1,3-dibromo-5,5-dimethylhydantoin. Bromination Reagent Stoichiometry: Different amounts of the brominating reagent can be used, from about 0.8 equiv to about 2 equiv. Drying: A temperature range of about 10° C. to about 60° C. could be used for drying.

The impurity 5-a is was prepared and characterized as follows. 10 g of Compound 4 and sulfuric acid (35 mol %) were dissolved in MeOH (10 vol). The mixture was set to stir at 20° C. to 25° C. for 5-10 min and 2.0 equivalents of NBS were charged in one portion. The resulting yellow mixture was stirred for three days at 20-25° C. The batch was concentrated under reduced pressure and the resulting solid was slurried in water at 95-100° C. for 3 hours. After a second overnight slurry in CH$_2$Cl$_2$ at room temperature, the batch was filtered and dried to give a white solid 5-a (15.0 g, 78%). $^1$H NMR (500 MHz, d6-DMSO), 8.05 (2H, s, Ar$\underline{H}$), 3.40 (1H, br s, $\underline{H}$O—Ar), 3.28 (3H, s, CH$_3$); MS (ES$^-$) calc. 327/329/331; found 327/329/331; MP (DSC): 226° C. (onset 221° C., 102 J/g); lit. 224-226° C.

1.2: O-Alkylation of 5 to Produce 6

Compound 6 was prepared according to Scheme 7 below.

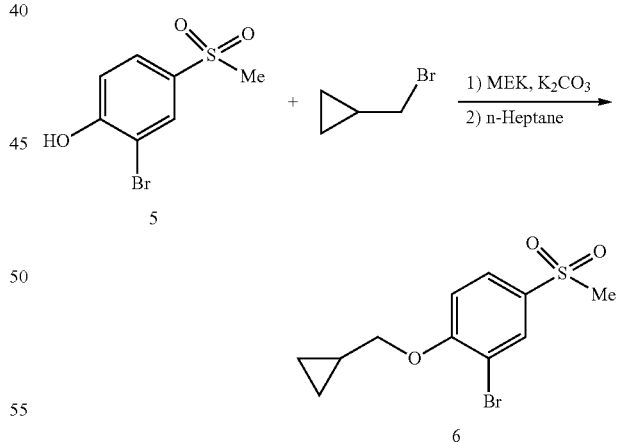

Compound 5 (100 g, 398 mmol) and methyl ethyl ketone (MEK, 700 mL) were charged to the reaction vessel and agitated. Potassium carbonate (K$_2$CO$_3$, 325 mesh 82.56 g, 597 mmol) was then charged to the stirred reaction vessel at 15° C. to 25° C. Bromomethylcyclopropane (64.4 mL, 664 mmol) was charged to the reaction vessel over at least 1 hour, maintaining the temperature between 15° C. to 25° C. MEK (200 mL) was added into the reactor and the reactor heated to 65 to 75° C. The contents of the reaction vessel were stirred at 65 to 75° C. for approximately 10 hours until reaction was complete by HPLC analysis. Water (3.0 vol, 3.0 wt) was charged to the vessel maintaining the temperature at 65 to 75° C. The batch was stirred at 65 to 75° C. The phases were allowed to separate at 65° C. to 75° C. and the lower aqueous phase was removed. Water (300 mL) was charged to the vessel maintaining the temperature at 65° C. to 75° C. The batch was agitated for at least 10 minutes at 65 to 75° C. The phases were allowed to separate at 65° C. to 75° C. and the lower aqueous phase was removed. The water wash was repeated once. The temperature was adjusted to 40 to 50° C. The mixture was concentrated to ca. 500 mL under reduced pressure. The mixture was distilled under reduced pressure at up to 50° C. with MEK until the water content was <1.0% w/w. n-heptane (500 mL) was charged to the vessel maintaining the temperature at 40 to 50° C. The mixture was continuously distilled under vacuum with n-heptane (300 mL), maintaining a 1 L volume in the reaction vessel. Compound 6 seeds (0.01 wt) were added at 40 to 50° C. The mixture was continuously distilled under reduced pressure at up to 50° C. with n-heptane (300 mL) while maintaining 1 L volume in the reactor. The batch was cooled to 15 to 25° C. and aged for 2 hours. The product was collected by suction filtration. The filter cake was washed with a solution of 10% MEK in n-heptane (5 vol) at 15 to 25° C. The filter cake was dried under reduced pressure at up to 40° C. under vacuum with nitrogen flow to afford 95 g of 6. $^1$H NMR (500 MHz, d$_6$-DMSO) 8.07 (1H, d, $^4$J=2.2 Hz, Ar H), 7.86 (1H, d, J=8.7 Hz, meta-ArH), 7.29 (1H, d, J=8.8 Hz, ortho-ArH), 4.04 (2H, d, J=6.9 Hz, OCH$_2$CH), 3.21 (3H, s, CH$_3$), 1.31-1.24 (1H, m, OCH), 0.62-0.58 (2H, m, 2×CHC H$_a$H$_b$), 0.40-0.37 (2H, m, 2×CHCH$_a$H$_b$); MS (ES$^+$) calc. 305/307; found 305/307; MP: (DSC) 93° C.

The following modifications of the above reaction, synthesis of 6 from 5, may be employed as well. Solvent: Different solvents could be used, for example acetone, methyl isobutyl ketone, ethyl acetate, isopropyl acetate, acetonitrile, or 2-methyl tetrahydrofuran. Reaction volume: Reaction volumes of 3 to 30 volumes with respect to 3 could be used. Base: Different inorganic bases, such as cesium carbonate or phosphate bases (sodium, potassium, or cesium) could be used. Also, organic bases, such as trimethylamine or diisopropyldiimide could be used. Base particle size: Different particle sizes of potassium carbonate from 325 mesh could be used. Reaction temperature: A lower temperature, such as 50° C. could be used. A higher temperature, such as about 100° C. could be used. Any temperature above the boiling point of the solvent could be run in a pressure vessel. Isolation: Different solvent ratios of MEK to n-heptane could be used. Different amounts of residual water can be left. Different amounts of seeds, from 0 to 50% could be used. Seeding could take place later in the process and/or at a lower temperature. An un-seeded crystallization can be employed. A different isolation temperature, from 0° C. to 50° C. could be used. A different wash could be used, for example a different ratio of MEK to n-heptane. A different antisolvent from n-heptane could be used, such as hexane, pentane, or methyl tert-butyl ether. Alternatively, the batch could be solvent exchanged into a solvent where Compound 3 has a solubility of less than 100 mg/ml and isolated from this system. Drying: A temperature range of 10 to 60° C. could be used for drying.

Compound 10, shown below may also be formed as a result of O-alkylation of unreacted 4 present in product 5, or alternatively from or via a palladium mediated proteodesbromination or proteodesborylation in subsequent chemistry discussed in Example 1.3 below.

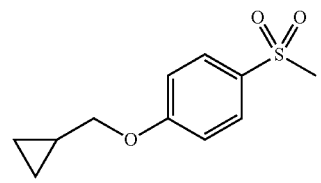

10

Preparation of methylsulfonylphenyl(cyclopropylmethyl) ether 10: Compound 4 (0.86 g, 5.0 mmol) and K$_2$CO$_3$ (1.04 g, 7.5 mmol) were slurried in acetone (17 mL, 20 vols). Cyclopropylmethyl bromide (0.73 mL, 7.5 mmol) was added in several small portions over ~1 minute and the reaction mixture heated to 50° C. for 48 hours, then cooled to 25° C. Water (5.0 mL) was added with stirring and the acetone was evaporated on a rotary evaporator from which a fine white solid formed which was filtered off and returned to a vessel as a damp paste. A 1:1 mixture of MeOH/water (8 mL) was added and heated to 40° C. with stirring. After 1 hour, the white solid was filtered off. Some residual solid was washed out with fresh water that was also rinsed through the cake, which was then isolated and left to air dry over the two days to give a dense white solid 10 (1.00 g, 88%). $^1$H NMR (500 MHz, CDCl$_3$) 7.85 (2H, d, J=8.8 Hz, RO—Ar ortho-H), 7.00 (2H, d, J=8.8 Hz, RO—Ar meta-H), 3.87 (2H, d, J=7.0 Hz, OCH$_2$CH), 3.02 (3H, s, CH$_3$), 1.34-1.23 (1H, m, OCH$_2$CH), 0.72-0.60 (2H, m, 2×CHC H$_a$H$_b$), 0.42-0.31 (2H, m, 2×CHCH$_a$H$_b$).

1.3: Synthesis and Isolation Coupling Partner Boronic Ester 2

The final bond forming step to Compound 1 is a Suzuki-Miyaura coupling between Compounds 2 and 3, as shown in Scheme 3 below (Norio, M. and Suzuki, A., Chem. Rev., 95(7), 2457-2483 (1995)). Early studies demonstrated that the boronic ester of the isoquinolinone Compound 3-a had poor physical attributes and solid phase stability (Kaila, N. et al., J. Med. Chem., 57: 1299-1322 (2014)). The pinacolatoboronate of the O-alkyl phenol, Compound 7, had acceptable solid phase stability and could be isolated via crystallization.

Scheme 3: Suzuki-Miyaura coupling between 2 and 3

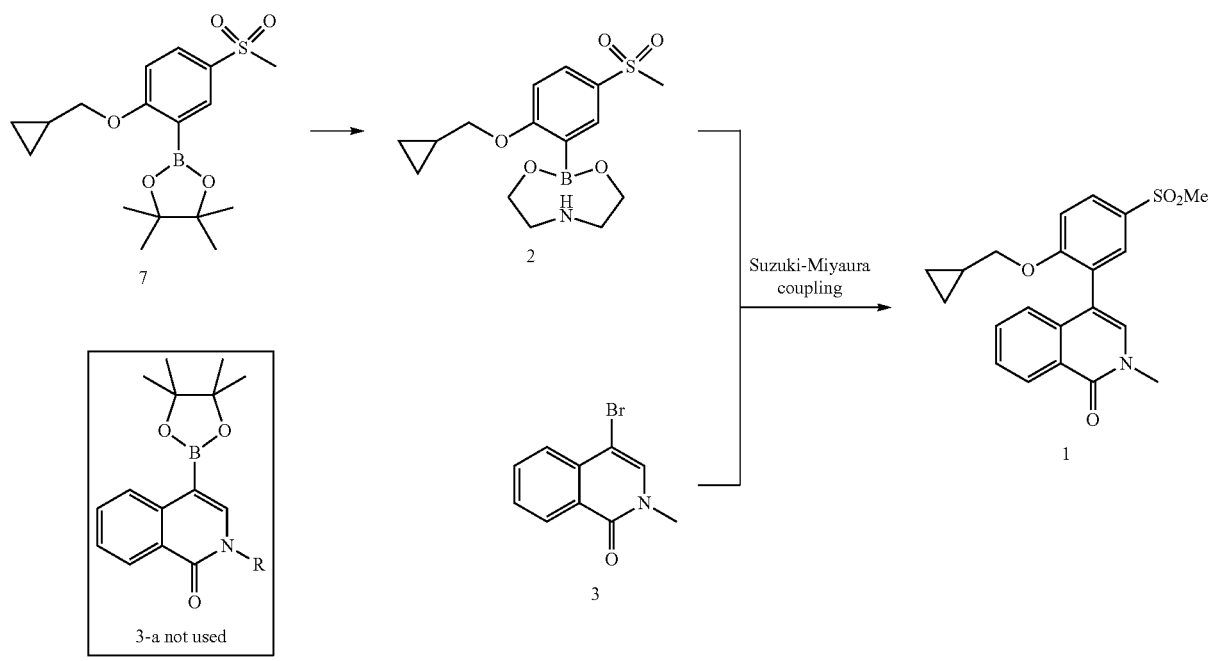

Process robustness studies for the isolation of Compound 7, however, indicated that Compound 7 has poor solution stability, decomposing primarily to the proteodeborylated compound 10, as shown in Scheme 4 below. This was particularly problematic as the isolation process involved a solvent exchange from 2-MeTHF (2-methyl tetrahydrofuran) to iPrOAc (isopropyl acetate), which is not a fast unit operation on scale.

A search for a more stable boronic ester was undertaken. Early attempts targeted making N-methyliminodiacetic acid (MIDA) boronate Compound 2-a (E. Gilis and M. Burke, "Multistep Synthesis of Complex Boronic Acids from Simple MIDA Boronates," *J. Am. Chem. Soc.,* 130(43): 14084-14085 (2008)), however, all attempts resulted in product decomposition. Applicant then turned to a relatively obscure boronate formed by the addition of diethanolamine Scheme 4: Modification of 7

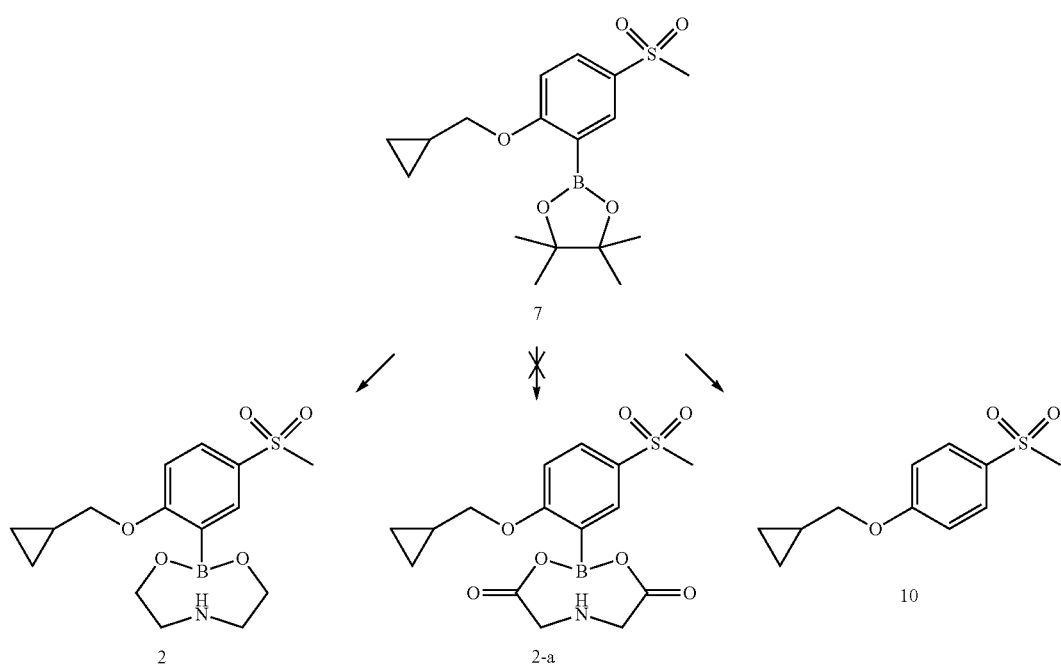

to Compound 7 (Bonin et al., *Tetrahedron Lett.*, 52:1132-1135 (2011)). Addition of diethanolamine to a solution of Compound 7 led to rapid ester formation and concomitant crystallization of Compound 2.

The discovery of boronic ester Compound 2 allowed for a simple, fast, high-yielding, high-purity process comprising the following procedure. Tetrahydrofuran (THF, 1500 mL) was charged to a flask containing Compound 6 (100 g, 328 mmol), bis(pinacolato)diboron (90.7 g, 357 mmol) and cesium acetate (CsOAc, 158 g, 822 mmol). The system was vacuum purged three times with nitrogen. Pd(PPh$_3$)$_2$Cl$_2$ (13.8 g, 20 mmol) was charged to the reaction and the system was vacuum purged three times with nitrogen. The reaction was then heated to 55 to 65° C.

The batch was stirred for approximately 8 hours until reaction was complete by HPLC analysis. The batch was cooled to 15 to 25° C. (target 20° C.) and charged with silica gel (20 g) and Ecosorb C-941 (20 g). After 1 h, the mixture was filtered to remove solid. The residual solids were washed twice, each with THF (300 mL). The filtrate and washes were combined. In a separate vessel, diethanolamine (34.5 mL, 360 mmol) was dissolved in THF (250 mL). The diethanolamine solution in THF (25 mL) was then charged to the batch. After 10 minutes, the batch was seeded with 2 (1 g) and aged for 1 to 2 hours. The remaining of the diethanolamine solution in THF was charged to the batch over at least 2 hours and the slurry was stirred for at least 2 hours. The product 2 was collected by suction filtration. The wet cake was washed thrice with THF (200 mL). The material was dried under vacuum at 40° C. with nitrogen purge yielding 94.6 g of 2.

The reaction to synthesize Compound 2 from Compound 6 described above may be modified as follows. Solvent: Different solvents from THF could be used, such as 1,4 dioxane or 2-methyltetrahydrofuran. Reaction volume: The reaction volume can be varied from 4 to 50 volumes with respect to compound 2. Catalyst and base: Different palladium catalyst and bases can be used for the borylation. Examples can be found in Chow et al., *RSC Adv.*, 3: 12518-12539 (2013). Borylation reaction temperature: Reaction temperatures from room temperature (20° C.) to solvent reflux can be used. Carbon/Silica treatment: The treatment can be performed without silica gel. The process can be performed without a carbon treatment. Different carbon sources from Ecosorb C-941 can be used. Different amounts of silica, from 0.01× to 1× weight equivalents, can be used. Different amounts of Ecosorb C-941, from 0.01× to 1× weight equivalents, can be used. Crystallization: A different addition rate of diethanolamine can be used. Different amounts of diethanolamine, from 1.0 to 3.0 molar equivalents can be used. A different cake wash with more or less THF can be used. Different amount of seeds from 0.0001× wt to 50× wt can be used. Alternatively, the process can be unseeded. Drying: A temperature range of 10° C. to 60° C. could be used for drying.

The subsequent Suzuki-Miyaura coupling between Compounds 2 and 3 also proceeded well, providing over 20 kg of crude compound 1 with an average molar yield of 80% and LCAP of 99.7%.

1.4: Synthesis of Coupling Partner 3

Cross-coupling partner 3 was prepared by two different processes corresponding to Schemes 8 and 9 shown below.

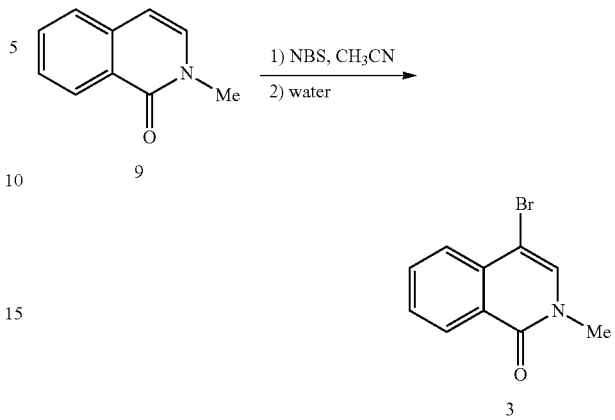

Scheme 8: Process A for the preparation of 3

According to Process A, Compound 9 (100 g, 628 mmol) was dissolved in acetonitrile (450 mL) at room temperature. In a separate vessel, N-bromosuccinimide (NBS, 112 g, 628 mmol) was suspended in acetonitrile (1 L). Compound 9 in acetonitrile was charged to the NBS slurry over at least 45 minutes. The contents of the reaction vessel were warmed to 45° C. to 55° C. and the batch stirred until the reaction was complete by HPLC analysis. The batch was cooled to 35° C. to 45° C. and ensured dissolution. Norit SX plus carbon (10 g) was charged to the mixture and the reaction mixture adjusted to 55° C. to 60° C. The mixture was stirred at 55° C. to 60° C. for about 1 h and the mixture filtered at 55° C. to 60° C. to remove solids. The solids were washed with acetonitrile (500 mL) at 55° C. to 60° C. The volume of the combined filtrate was reduced to 900 mL by distilling off acetonitrile under reduced pressure. The batch with Compound 3 (1 g) and stirred at 35° C. to 45° C. for at least 60 minutes. The contents of the reaction vessel were cooled to 15° C. to 25° C. over at least 1 hour. Water (2000 mL) was charged to the reaction vessel over at least 90 minutes and the slurry aged for at least 60 minutes. The product was collected by suction filtration. The cake was washed with a premixed 5% solution of acetonitrile in water (300 mL). The wet cake was dried under vacuum at 40° C. with nitrogen purge. Yield: 120 g of 3.

The above procedure, Process A for this synthesis of 3, may be practiced with alternative reagents and conditions as follows. Solvents: Alternative solvents could be used. Examples include chlorinated solvents, such as methylene chloride, chloroform or 1,2 dichloroethane, and non-chlorinated solvents such as tetrahydrofuran, or 2-methyltetrahydrofuran. Reaction concentration: The reaction concentration can be varied from 2× vol to 40× vol (with respect to Compound 9). Brominating agents: Additional brominating reagents include bromine and 1,3-dibromo-5,5-dimethylhydantoin. Bromination reagent Stoichiometry: Different amounts of the brominating reagent can be used, from 0.8 equiv to 2 equiv. Crystallization: Different amounts of water, including 5 volumes to 50 volumes can be used. The crystallization can also proceed without the addition of seeds. Different water addition times and final hold times can be used. Different wash procedures can be used. Drying: A temperature range of 10° C. to 60° C. could be used for drying.

Scheme 9: Process B for preparation of 3

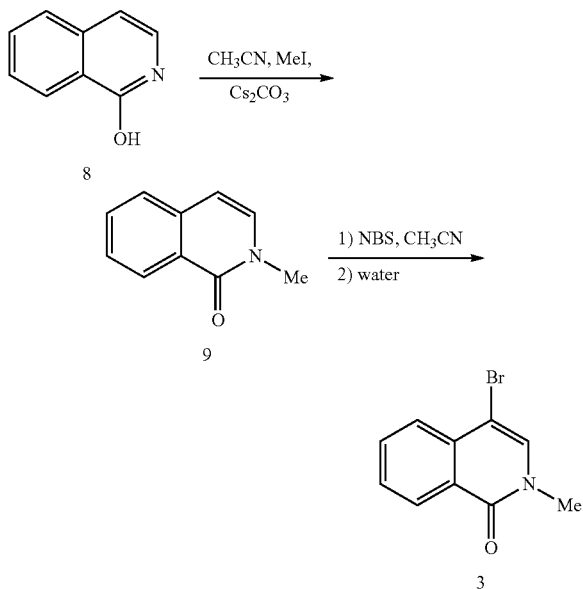

According to Process B, Compound 3 can be formed starting from 8 via non-isolated compound 9 as follows. Compound 8 (80 g, 55 mmol), cesium carbonate ($Cs_2CO_3$, 215 g, 66 mmol), and acetonitrile (800 mL) were charged to the reactor. The temperature was adjusted from 15 to 25° C. and iodomethane charged to the reactor (MeI, 86 g, 0.61 mol) while maintaining a batch temperature below 25° C. The batch was heated to 40° C. and agitated for 10 hours to form Compound 9. The batch was cooled to 25° C., filtered into a fresh reactor to remove solids, and the solids washed twice with acetonitrile. The combined organic layers were concentrated via atmospheric distillation to about 320 mL.

In a separate reactor N-bromosuccinimide (NBS, 98.1 g, 0.55 mol) was charged to acetonitrile (800 mL) and agitated. The batch containing Compound 9 was transferred to the NBS solution while maintaining a batch temperature of 15 to 25° C. The batch was heated to 45 to 55° C. and agitated for at least 4 hours to allow for reaction completion to Compound 3. Upon reaction completion, Norit SX Plus activated carbon (8 g) was charged, and agitated at 45 to 55° C. for one hour. The batch was filtered into a fresh vessel, the Norit SX plus cake was washed with 400 ml of 45 to 55° C. acetonitrile. The acetonitrile layers were combined, cooled to 35 to 45° C., and distilled under reduced pressure to 720 mL. The batch was adjusted to a temperature of 40° C., charged with Compound 3 seeds (0.8 g), agitated for one hour, cooled to 15 to 25° C. over at least on hour, then charged with water (1600 mL) over at least two hours. The mixture was agitated for an additional one to two hours, filtered, the cake washed with a premixed 5% solution of acetonitrile in water (240 mL). The wet cake was dried under vacuum at 40° C. with nitrogen purge. Yield: 52 g of 3.

Process B to synthesize Compound 3, described above, may be modified as follows. Solvents: Alternative solvents could be used. Examples include chlorinated solvents, such as methylene chloride, chloroform or 1,2 dichloroethane, and non-chlorinated solvents such as tetrahydrofuran, or 2-methyltetrahydrofuran. Reaction concentration: The reaction concentration can be varied from 2x vol to 40x vol (with respect to Compound 8). Alkylating reagent: Alternative methylating reagents to methyl iodide can be used such as dimethylsulfate. Alkylating reagent stoichiometry: 1 to 10 molar equivalents of methyl iodide may be used. Base: Different inorganic bases, such as potassium carbonate or phosphate bases (sodium, potassium, or cesium) could be used. Brominating agents: Additional brominating reagents include bromine and 1,3-dibromo-5,5-dimethylhydantoin. Bromination reagent stoichiometry: Different amounts of the brominating reagent can be used, from 0.8 equiv to 2 equiv. Crystallization: Different amounts of water, including 5 volumes to 50 volumes can be used. Seeding levels from 0.0001% to 50% can be used. The crystallization can also proceed without the addition of seeds. Different water addition times and final hold times can be used. Different wash procedures can be used. Drying: A temperature range of 10 to 60° C. could be used for drying.

1.5: Cross-Coupling of 2 and 3 to Produce Target Compound 1

1 is synthesized by Suzuki cross-coupling of 3 and 2 according to Scheme 10 and as described below.

Scheme 10: Synthesis of 1

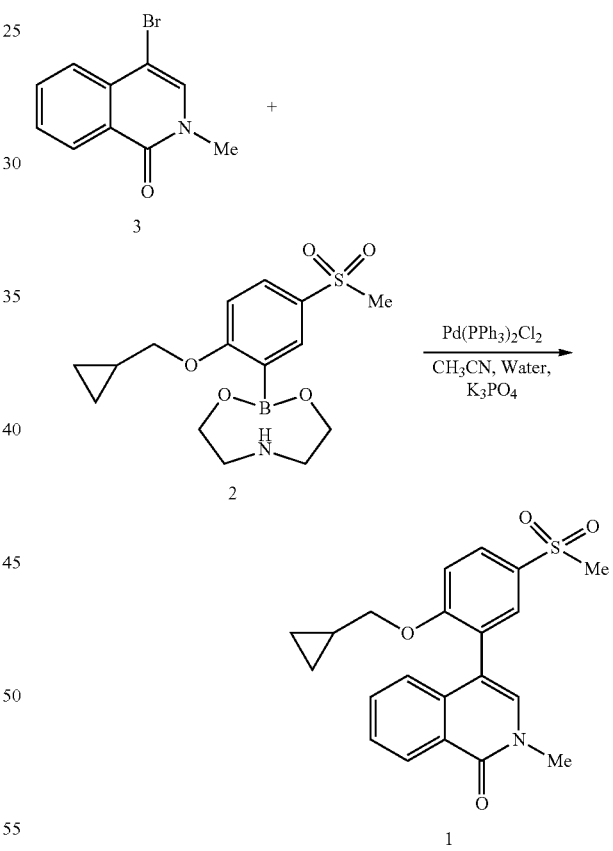

Acetonitrile (1.6 L) was charged to a mixture of Compound 2 (156.7 g, 460 mmol), Compound 3 (100 g, 420 mmol) and potassium phosphate tribasic (223 g, 1.05 mol). Agitation was begun and water (400 mL) charged to the batch. The system was vacuum purged three times with nitrogen and charged with $Pd(PPh_3)_2Cl_2$ (2.9 g, 4 mmol) and the system vacuum purged three times with nitrogen. The batch was heated to 65 to 75° C. and contents stirred for at least 16 hours until reaction was complete by HPLC analysis. The batch was cooled to 60 to 70° C., agitation halted and the mixture allowed to settle. The bottom aqueous layer was removed. Water (150 mL) and acetonitrile (700 mL) were charged at 60 to 70° C. Ecosorb C-941 (15 g) and Celite (10 g) were charged to the reaction vessel at 60 to 70° C. After 1 h, the mixture was filtered to remove solids. The solids were washed twice each with 18% water in acetonitrile (500 mL) at 60 to 70° C. The filtrates were combined and concentrated under atmospheric pressure to a final volume of 1.5 L. The batch was cooled to 60 to 65° C. and seeded with Compound 1 (1 g). After 1 h, water (500 mL) was charged over at least 1 hour at 60 to 65° C. The slurry was cooled to 15 to 25° C. over 4 hours. The product was collected by suction filtration. The wet cake was washed with 45% water in acetonitrile (500 mL) twice. The product was dried under vacuum at 40° C. with nitrogen purge. Yield: 139 g of 1.

The above procedure for coupling Compound 3 and Compound 2 to produce Compound 1 may be modified in any of the ways that follow. Reaction solvents: Different reaction solvents from acetonitrile can be used, including tetrahydrofuran, 2-methyl tetrahydrofuran, toluene, and isopropanol. Boronic ester: Different boronic esters from Compound 2 can be used, including pinacolato ester compound 7, and the free boronic acid of Compound 2. Examples of boronic esters can be found in Lennox, Alister, J. J., Lloyd-Jones, Guy C. Chem. Soc. Rev., 2014, 43, 412. Carbon treatment: Different carbon treatments from Ecosorb C-941 could be used. Different amounts of carbon, from 0.01 to 0.5× weight can be used. The carbon can be eliminated. Different amounts of Celite, from 0.01 to 0.5× weight can be used. Crystallization: Different amounts of water, including 5 volumes to 50 volumes can be used. The crystallization can also proceed without the addition of seeds. Different water addition times and final hold times can be used. Different wash procedures can be used. Drying: A temperature range of 10 to 60° C. could be used for drying. Catalysts: Different metal and ligand combination could be used. Examples of metal/ligand combinations can be found in Maluenda, Irene; Navarro, Oscar, Molecules, 2015, 20, 7528. Various catalysts can be including: XPhos-3G (cas #1445085-55-1); cataCXium® A Pd 3G (CAS #1651823-59-4); PdCl$_2$(DtBPF) (CAS #95408-45-0); SPhos 3G (Cas #1445085-82-4); AmPhos 3G (Cas #1820817-64-8); PCy$_3$ 3G (Cas #1445086-12-3); Pd PEPPSI IPent Cas #1158652-41-5); Pd(PPh$_3$)$_2$Cl$_2$ (Cas #13965-03-2). Examples of catalyst systems that have been demonstrated to afford Compound 1 are listed below in Table 4 using boronic esters 2 or 7 in coupling to 3.

TABLE 4

Catalyst screen summary

| Solvent_Ligand | Conversion to Product at t = 3 h | |
|---|---|---|
| | HB071 | HB075 |
| THF_xPhos 3G | 79.7 | 88.8 |
| THF_CataCXium A 3G | 80.8 | 85.8 |
| THF_PdCl2(DtBPF) | 89.8 | 86.4 |
| THF_SPhos 3G | 71.5 | 88.7 |
| THF_APhos 3G | 83.8 | 85.2 |
| THF_PCy3 3G | 70.0 | 85.2 |
| THF_Pd PEPPSI IPent | 62.2 | 51.9 |
| THF_Pd(PPh3)2Cl2 | 74.8 | 82.9 |
| 2-MeTHF_XPhos 3G | 92.1 | 81.3 |
| 2-MeTHF_CataCXium A 3G | 89.8 | 87.6 |
| 2-MeTHF_PdCl2(DtBPF) | 89.3 | 88.7 |
| 2-MeTHF_SPhos 3G | 86.3 | 85.5 |
| 2-MeTHF_APhos 3G | 90.9 | 88.9 |

TABLE 4-continued

Catalyst screen summary

| Solvent_Ligand | Conversion to Product at t = 3 h | |
|---|---|---|
| | HB071 | HB075 |
| 2-MeTHF_PCy3 3G | 78.6 | 89.8 |
| 2-MeTHF_Pd PEPPSI IPent | 74.6 | 61.7 |
| 2-MeTHF_Pd(PPh3)2Cl2 | 77.9 | 88.7 |
| MeCN_XPhos 3G | 95.5 | 84.1 |
| MeCN_CataCXium A 3G | 78.5 | 69.8 |
| MeCN_PdCl2(DtBPF) | 91.6 | 85.3 |
| MeCN_SPhos 3G | 92.6 | 85.9 |
| MeCN_APhos 3G | 88.3 | 89.8 |
| MeCN_PCy3 3G | 86.8 | 88.3 |
| MeCN_Pd PEPPSI IPent | 87.4 | 90.5 |
| MeCN_Pd(PPh3)2Cl2 | 86.5 | 90.6 |

1.6: Crystallization of 1

The final isolation of Compound 1 requires a polish filtration. For this, the batch must be completely soluble. Unfortunately, Compound 1 has low solubility in almost all International Council for Harmonisation of Technical Requirements for Pharmaceuticals for Human Use (ICH) Class 3 and common Class 2 (e.g. THF, MeCN) solvents (ICH Harmonized Guideline "Impurities: Guideline for Residual Solvents Q3C(R6)" Oct. 20, 2016). A reasonable solubility was obtained in a warm MeCN-water mix, but this is not an optimal system (requires a heated filtration, MeCN has a residual solvent limit of only 410 ppm). Additional solvents with reasonable solubility (>50 mg/ml) include N-methyl-2-pyrrolidone (NMP) and dimethylacetamide (DMAc); but the development of isolations from these solvents required large volumes and raised residual solvent limit concerns (530 ppm or less for NMT and 1090 ppm or less for DMAc).

catalyst systems that have been demonstrated to afford Compound 1 are listed below in Table 4 using boronic esters 2 or 7 in coupling to 3.

TABLE 4

Catalyst screen summary

| Solvent_Ligand | Conversion to Product at t = 3 h | |
|---|---|---|
| | HB071 | HB075 |
| THF_XPhos 3G | 79.7 | 88.8 |
| THF_CataCXium A 3G | 80.8 | 85.8 |
| THF_PdCl2(DtBPF) | 89.8 | 86.4 |
| THF_SPhos 3G | 71.5 | 88.7 |
| THF_APhos 3G | 83.8 | 85.2 |
| THF_PCy3 3G | 70.0 | 55.2 |
| THF_Pd PEPPSI IPent | 62.2 | 51.9 |
| THF_Pd(PPh3)2Cl2 | 74.8 | 52.3 |
| 2-MeTHF_XPhos 3G | 92.1 | 61.3 |
| 2-MeTHF_CataCXium A 3G | 89.8 | 87.6 |
| 2-MeTHF_PdCl2(DtBPF) | 89.3 | 86.7 |
| 2-MeTHF_SPhos 3G | 86.3 | 85.6 |
| 2-MeTHF_APhos 3G | 90.9 | 86.9 |
| 2-MeTHF_PCy3 3G | 78.6 | 69.8 |
| 2-MeTHF_Pd PEPPSI IPent | 74.6 | 61.7 |
| 2-MeTHF_Pd(PPh3)2Cl2 | 77.9 | 38.2 |
| MeCN_XPhos 3G | 95.5 | 84.1 |
| MeCN_CataCXium A 3G | 78.5 | 69.8 |
| MeCN_PdCl2(DtBPF) | 91.6 | 85.3 |
| MeCN_SPhos 3G | 92.6 | 85.9 |
| MeCN_APhos 3G | 88.3 | 89.3 |
| MeCN_PCy3 3G | 86.8 | 35.3 |
| MeCN_Pd PEPPSI iPent | 87.4 | 90.5 |
| MeCN_Pd(PPh3)2Cl2 | 86.5 | 90.6 |

TABLE 4-continued

Catalyst screen summary

| | Conversion to Product at t = 3 h | |
|---|---|---|
| Solvent_Ligand | HB071 | HB075 |

HB071

Compound 3 + Compound 7 → Compound 1

HB075

Compound 3 + Compound 2 → Compound 1

1.6: Crystallization of 1

The final isolation of Compound 1 requires a polish filtration. For this, the batch must be completely soluble. Unfortunately, Compound 1 has low solubility in almost all International Council for Harmonisation of Technical Requirements for Pharmaceuticals for Human Use (ICH) Class 3 and common Class 2 (e.g. THF, MeCN) solvents (ICH Harmonized Guideline "Impurities: Guideline for Residual Solvents Q3C(R6)" Oct. 20, 2016). A reasonable solubility was obtained in a warm MeCN-water mix, but this is not an optimal system (requires a heated filtration, MeCN has a residual solvent limit of only 410 ppm). Additional solvents with reasonable solubility (>50 mg/ml) include N-methyl-2-pyrrolidone (NMP) and dimethylacetamide (DMAc); but the development of isolations from these solvents required large volumes and raised residual solvent limit concerns (530 ppm or less for NMT and 1090 ppm or less for DMAc).

Figure 7:
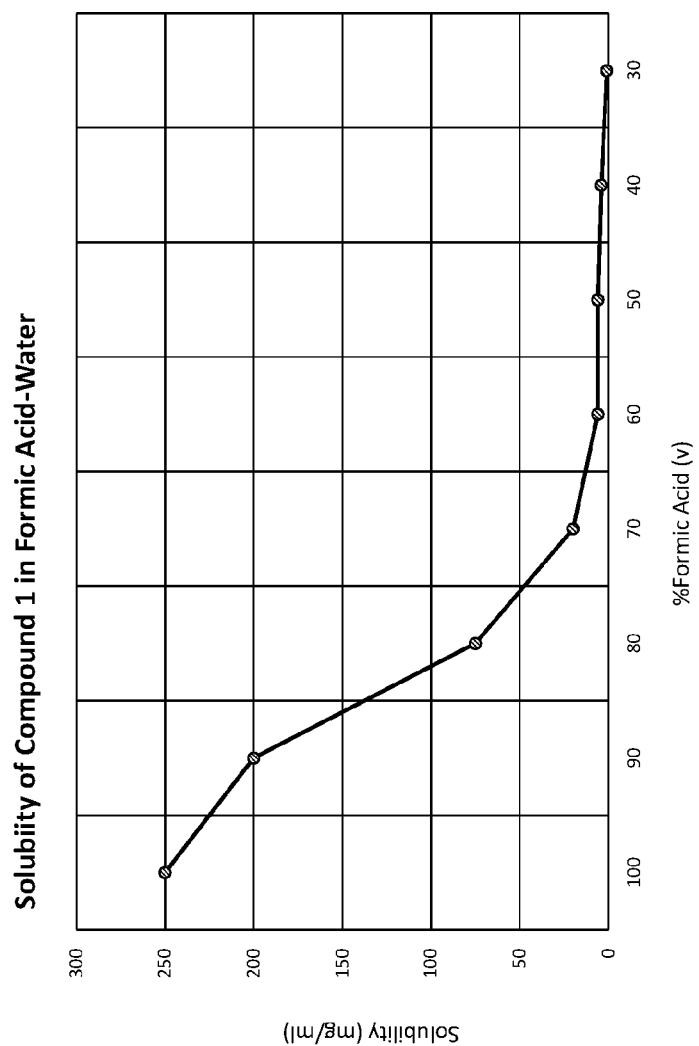
FIG. 7 shows the solubility curve of 1.

Formic acid is one ICH Class 3 solvent in which Compound 1 is highly soluble, having a solubility greater than 250 mg/ml at 20° C. The solubility curve of Compound 1 in formic acid-Water is quite steep (see FIG. 7), which enables a volumetrically efficient process.

Initial attempts to recrystallize crude Compound 1 involved dissolving in formic acid, polish filtering, and charging polish filtered water to about 20% supersaturation, followed by seeding with the thermodynamically most stable form (Form 1), followed by slow addition of water to the final solvent ratio, filtration, washing, and drying. Applicant observed that during the initial water charge, if the batch self-seeded it formed a thick slurry. X-ray diffraction (XRD), differential scanning calorimetry (DSC), and photomicroscopy demonstrated that a metastable form was produced. Once seeded with Form 1, the batch converted to the desired form (Form 1) prior to the addition of the remaining water. This process worked well during multiple lab runs, consistently delivering the desired form and purity with about 85% yield.

Figure 8:
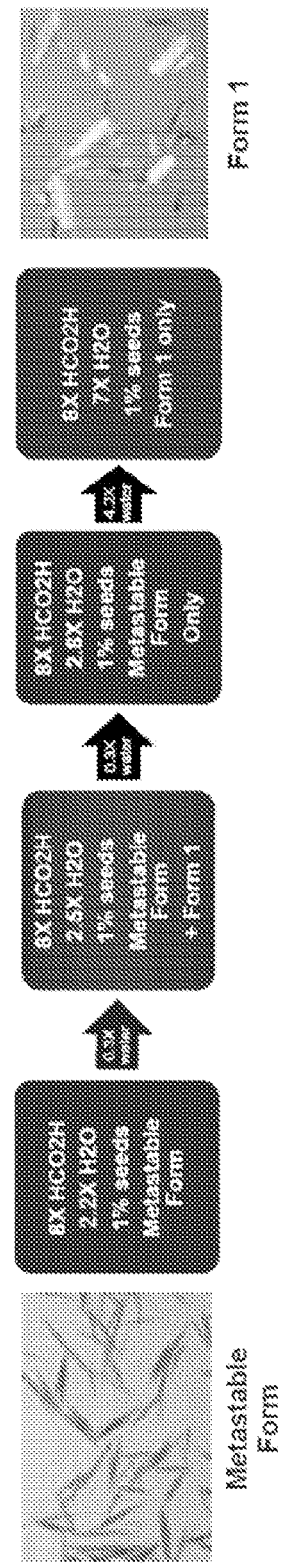
FIG. 8 shows a first schematic of polymorph interconversion during the process purification for 1.

Unfortunately, upon scale-up, the batch did not convert to Form 1 after seeding. Additional water was charged and the batch began to convert to the desired form (mix of Form 1 and the metastable form by X-ray powder diffraction (XRPD)). When additional water was charged, the XRPD indicated only the metastable form. After a few hours with no change, Applicant continued the water charge to the final solvent ratio, during which time the batch eventually converted to Form 1. This process is summarized in FIG. 8.

Figure 9:
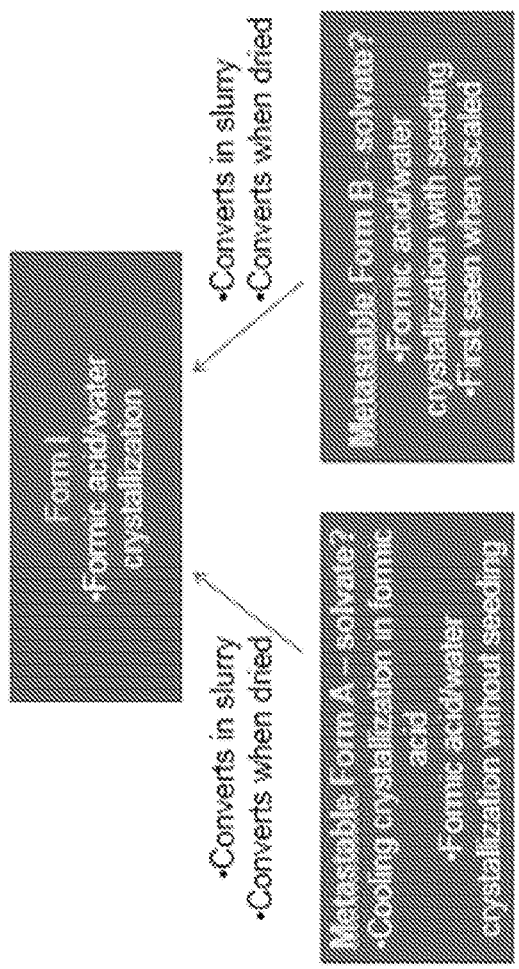
FIG. 9 shows a second schematic of polymorph interconversion during the process purification for 1.

It was subsequently found by closer analysis of the plant and laboratory retains that a new metastable form was formed during scale up, with a similar, but different XRPD pattern. This form (metastable B) could be reproduced in the laboratory, but only when the batch has a high formic acid:water ratio and is seeded with Form 1. Without Form 1 seeds, metastable A is the kinetic form. Both metastable forms converted to Form 1 with additional water and/or upon drying, leading Applicant to believe that the metastable forms are formic acid solvates. These findings are summarized in FIG. 9.

While there is little risk in not being able to control the final form, there is a risk of forming a difficult-to-stir slurry which can lead to processing issues. The crystallization procedure was therefore modified to keep a constant formic acid-water ratio. This was performed by charging 2.4× wt. formic acid and 1.75× wt. water (final solvent composition) to the crystallizer with 0.03× wt. Form 1 seeds, and performing a simultaneous addition of Compound 1 in 6.1× wt. formic acid and 4.4× wt. water. The batch filtered easily and was washed with formic acid/water, then water, and dried under reduced pressure to yield 8.9 kg of Compound 1 (92% yield) with 99.85% LCAP and N.D. formic acid.

Example 2: Exemplary High Throughput Experimentation Reaction

The following procedure is an exemplary high throughput experimentation reaction.

An overview of the reaction is shown below in Scheme 5:

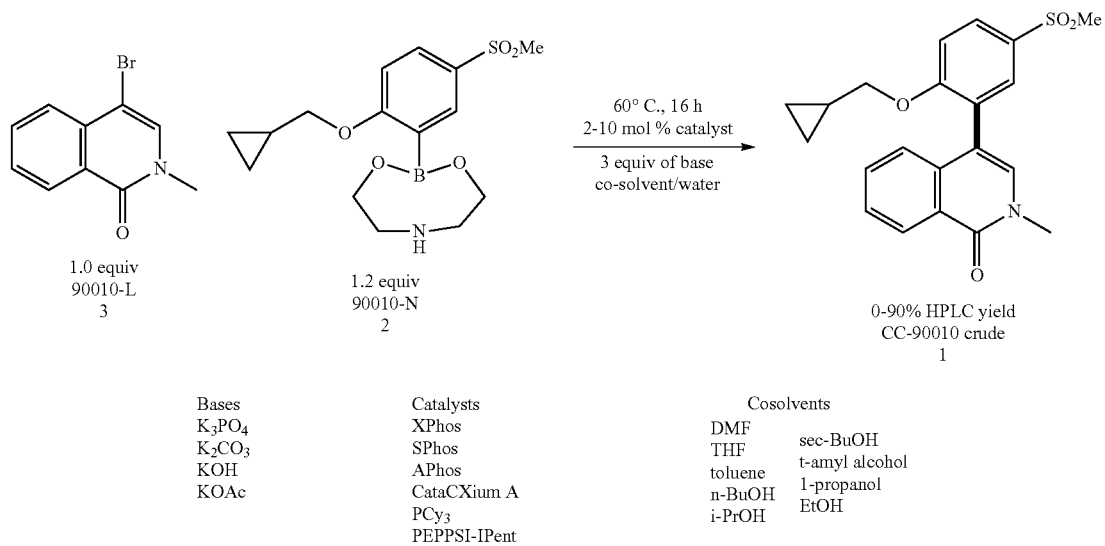

Pd catalysts were dosed into the 24-well reactor vial as solutions (100 μL of 0.01 M solution in tetrahydrofuran (THF) or dichloroethane (DCE) depending upon the solubility of the ligand). Plates of these ligands are typically dosed in advance of the reaction, the solvent is removed by evacuation in an evaporative centrifuge and plates are stored in the glovebox. The catalysts screened in the coupling are the following: XPhos, SPhos, CataCXium A, APhos, P(Cy)$_3$, PEPPSI-IPent. For the first five ligands, these were initially screened as the Buchwald Pd G2/G3 precatalysts.

To the plates was then added a stock solution of Compound 3 (10 μmol) and Compound 2 (12 μmol) dissolved in the following solvents: dimethylformamide (DMF), tetrahydrofuran (THF), butanol (n-BuOH), and toluene. The base was then added as a stock solution (30 μmol) in 20 μL of water.

A heatmap summarizing catalyst performance is shown in FIGS. 10A and 10B. High performance liquid chromatography (HPLC) yields for this screening span from <5% up to ~85%. Larger circles indicate higher yield. Lighter circles indicate higher cleanliness.

A similarly designed screening of base and solvent also indicate that a range of alcoholic solvents (methanol, ethanol, propanol, 2-butanol, 2-propanol, and t-amyl alcohol) are also all viable in this coupling chemistry. Bases such as potassium phosphate, potassium carbonate, potassium acetate, and potassium hydroxide were all successful in achieving the coupling. FIG. 10B shows a heatmap with HPLC yields ranging from ~50-95%. Larger, darker circles indicate higher yield.

This chemistry from microvial screening has been scaled to a laboratory process. To a 3-necked jacketed 250 mL flask equipped with overhead stirring, nitrogen inlet, and thermocouple was added Compound 3 (1.0 eq, 4.00 grams), Compound 2 (1.2 eq, 1.71× wt), potassium carbonate (3.0 eq, 1.74× wt). The reactor was inerted three times and then degassed 2-propanol (24× vol.) followed by degassed water (6× vol) was then added. Stirring was then initiated at 300 rpms. The reactor was then stirred and blanketed with nitrogen for 1 hour. The catalyst was then added (0.01 eq, 0.028× wt) and stirring continued (300 rpms) and the reactor was heated into the $T_j$=65° C.

After 2 hours, with full conversion confirmed analytically, trioctylphosphine (0.1 eq, 0.16× wt) dosed, and reaction mixture allowed to cool slowly to room temperature hours. The reaction mixture was then filtered, washed with 2-propanol (4× vol), 2-propanol:water (4:1, 4× vol), and then with water (4× vol). Note: If 2 is dimer present in cake, an additional ethyl acetate (EtOAc) wash (4× vol) can be added for purging. The cake was then transferred to a vacuum oven to dry overnight at 40° C., –40 cm Hg, under nitrogen flow. After transfer to a bottle, 6.03 grams of 1 were isolated, 98.6% assay, 91% overall yield.

Scheme 6: Alternative reagents and solvents for cross-coupling

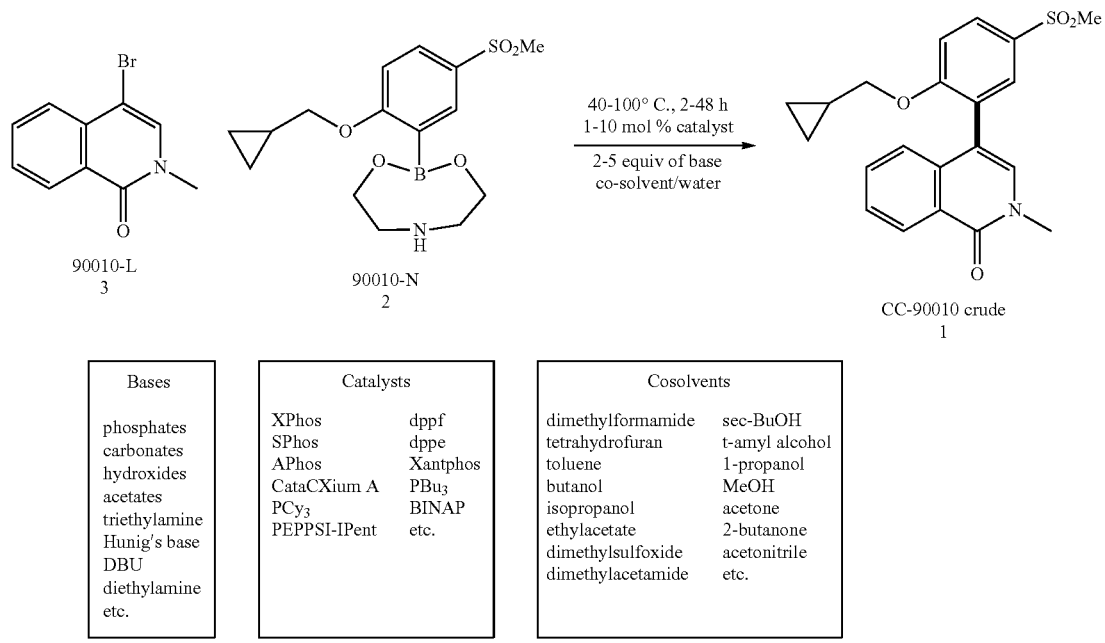

| Bases | Catalysts | | Cosolvents | |
|---|---|---|---|---|
| phosphates | XPhos | dppf | dimethylformamide | sec-BuOH |
| carbonates | SPhos | dppe | tetrahydrofuran | t-amyl alcohol |
| hydroxides | APhos | Xantphos | toluene | 1-propanol |
| acetates | CataCXium A | PBu$_3$ | butanol | MeOH |
| triethylamine | PCy$_3$ | BINAP | isopropanol | acetone |
| Hunig's base | PEPPSI-IPent | etc. | ethylacetate | 2-butanone |
| DBU | | | dimethylsulfoxide | acetonitrile |
| diethylamine | | | dimethylacetamide | etc. |
| etc. | | | | |

Based on the previously delineated results, it was expected that a variety of monodentate (PPh$_3$ [triphenylphosphine], PBu$_3$ [tributylphosphine], etc.) and bidentate phosphines (dppf [1,1'-bis(diphenylphosphino)ferrocene], BINAP [2,2'-bis(diphenylphosphino)-1,1'-binaphthyl], Xantphos [4,5-bis(diphenylphosphino)-9,9-dimethylxanthene], dppe [1,2-bis(diphenylphosphino)ethane], etc.) ligated to any number of Pd sources (Pd halides, Pd(II) precatalyts, Pd(O) sources) could reasonably be employed to arrive at the Compound 1 crude material. A range of organic solvents ranging from non-polar (heptane, benzene), protic (alcohols), polar aprotic (dimethylsulfoxide, dimethylformamide, dimethylacetamide, acetonitrile) as well as a variety of esters and ketones (acetone, 2-butanone, ethylacetate) should also serve as effective solvents for this reactivity. Finally, inorganic bases of varying strength (phosphates, carbonates, acetates, etc.) along with organic variants such as triethylamine, 1,8-diazabicyclo(5.4.0)undec-7-ene, and others in a wide pKa range are viable as stoichiometric basic additives.

Example 3: Exemplary Compound 5 Process

The purpose of this example was to describe an exemplary process for making Compound 5.

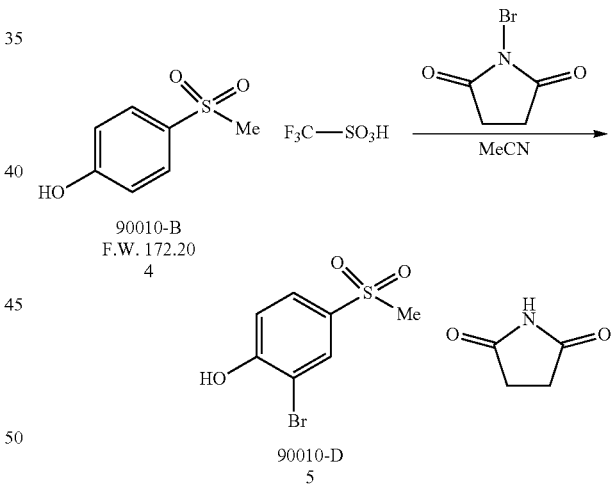

TABLE 5

| | | | Basis SM wt MW 172.02 g 10.00 Mol 0.058 | | | | | | | |
|---|---|---|---|---|---|---|---|---|---|---|
| Reagent | Grade | MW | Mol Eq. | M M/L | Density g/mL | Mass g | Vol mL | Moles | X Wt. | X Vol. |
| 90010-B; 4 | 97% (14763-60-1) | 172.02 | 1.00 | | | 10.00 | — | 0.058 | 1.00 | — |
| NBS | Reagent (128-08-5) | 177.98 | 1.10 | | | 11.38 | — | 0.064 | 1.14 | — |

TABLE 5-continued

Basis SM wt
MW 172.02
g 10.00
Mol 0.058

| Reagent | Grade | MW | Mol Eq. | M M/L | Density g/mL | Mass g | Vol mL | Moles | X Wt. | X Vol. |
|---|---|---|---|---|---|---|---|---|---|---|
| Triflic acid | Reagent Plus (1493-13-6) | 150.08 | 1.07 | | 1.70 | 9.34 | 5.5 | 0.062 | 0.93 | 0.55 |
| MeCN | reagent (75-05-8) | 41.05 | 33.00 | | 0.79 | 78.75 | 100.2 | 1.918 | 7.87 | 10.02 |
| 90010-D; 5 | (20951-43-3) | 251.10 | 1.00 | | | 14.60 | — | 0.058 | 1.46 | — |
| water | reagent (7732-18-5) | 18.00 | 29.00 | | 1.00 | 30.35 | 30.3 | 1.686 | 3.03 | 3.03 |

Charge 4 (10 g, 58 mmol) and acetonitrile (100 mL) to a reaction vessel and start the stirrer. Adjust the batch to −18° C. to −22° C. (target −20° C.). Charge triflic acid (5.5 mL, 62 mmol) to the batch maintaining −10° C. to −25° C. (target −20° C.). Stir the batch at −10° C. to −25° C. (target −20° C.) for 10 to 20 minutes. Charge NBS (11.38 g, 64 mmol) to the batch at −10° C. to −25° C. (target −20° C.) and stir for ca. 30 min at −10° C. to −25° C. (target −20° C.). Warm the batch to 20° C. over 3-4 hours (reaction will occur when internal temp is between 5° C. and 15° C.). Stir the batch at 15° C. to 25° C. (target 20° C.) for approximately 1 hour and sample for reaction completion.

If Compound 4 relative to Compound 5 is more than 5%:

Cool the bath to −5° C. to −15° C. (target −10° C.) (cooling below 0° C. to ensure selectivity). Charge NBS to the batch according to the follow formula: Mass of NBS=(% Compound 4×10 g). Warm the batch to 20° C. over 1-2 hours. Stir the batch at 15° C. to 25° C. (target 20° C.) for approximately 1 hour and check reaction for completion. Proceed to next line.

If Compound 4 relative to Compound 5 is less than 5%:

Warm the batch to 40° C. to 50° C. (target 48° C.). Concentrate the batch under reduced pressure to a final volume of ~40 mL. Cool the batch to −15° C. to −5° C. (target −10° C.) and stir for ca. 1 h. Filter the batch by suction filtration. Slurry wash the filter cake with purified water (3×20 mL) at 15° C. to 25° C. (target 20° C.) for 10 to 15 minutes each wash. Remove a sample of the filter cake for analysis by $^1$H NMR. Continue washing cake until the residual succimide is below 1.0% mol % relative to 5. Dry the filter cake at up to 60° C. under vacuum and nitrogen purge. Analyse the 5 by HPLC analysis (97% w/w to 99% w/w). Expected yield: 60-85% theory (90-110% w/w).

Example 4: Purification of Compound 1 (CC-90010) by Crystallization from Formic Acid and Water This example describes a method for the purification of Compound 1 by crystallization from formic acid and water. Also detailed are methods for obtaining three different polymorphs of Compound 1, including the most stable form, Form 1.

Figure 11:
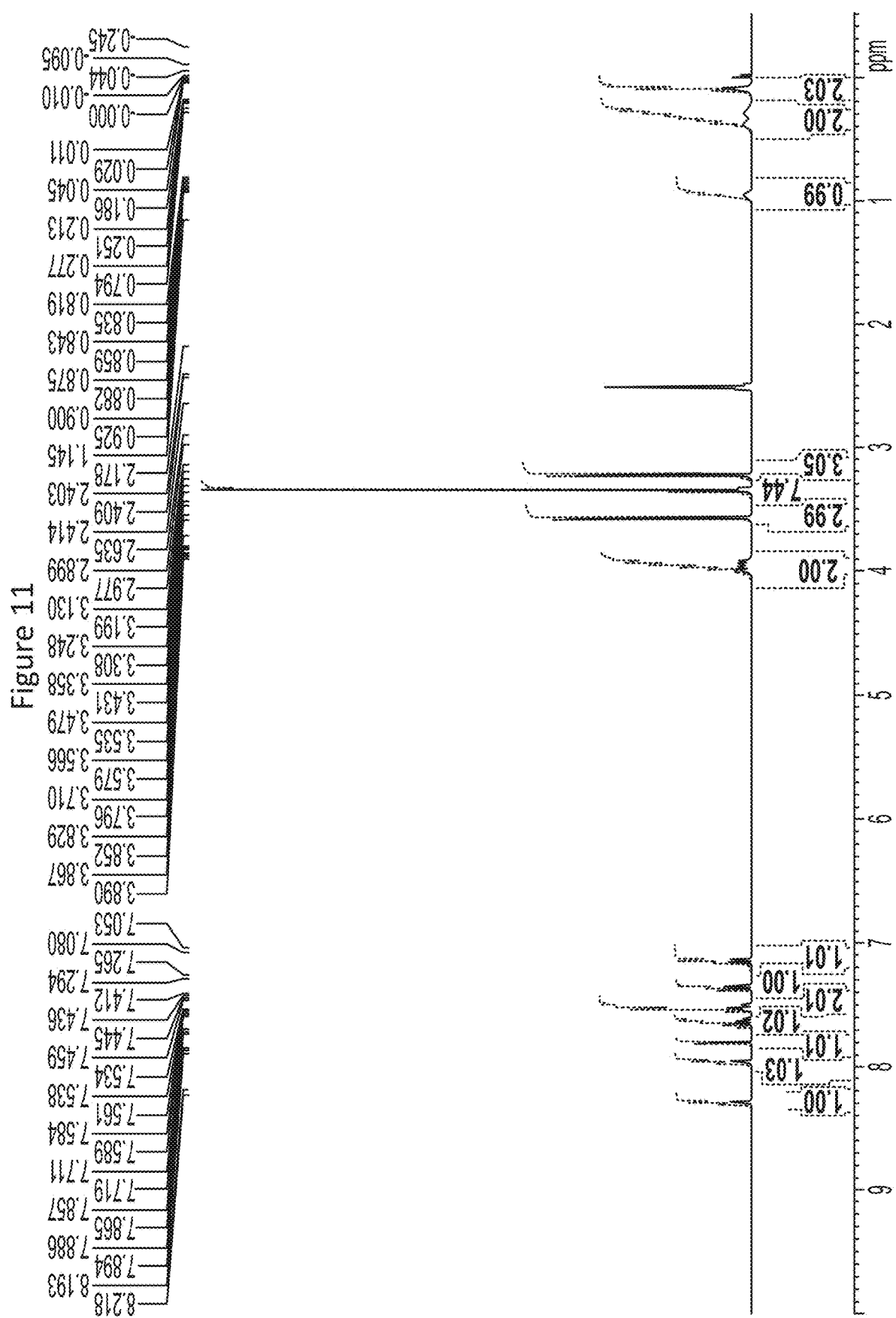
FIG. 11 shows 1H NMR of Compound 1 (CC-90010). Solvent: d6DMSO.
Figure 12:
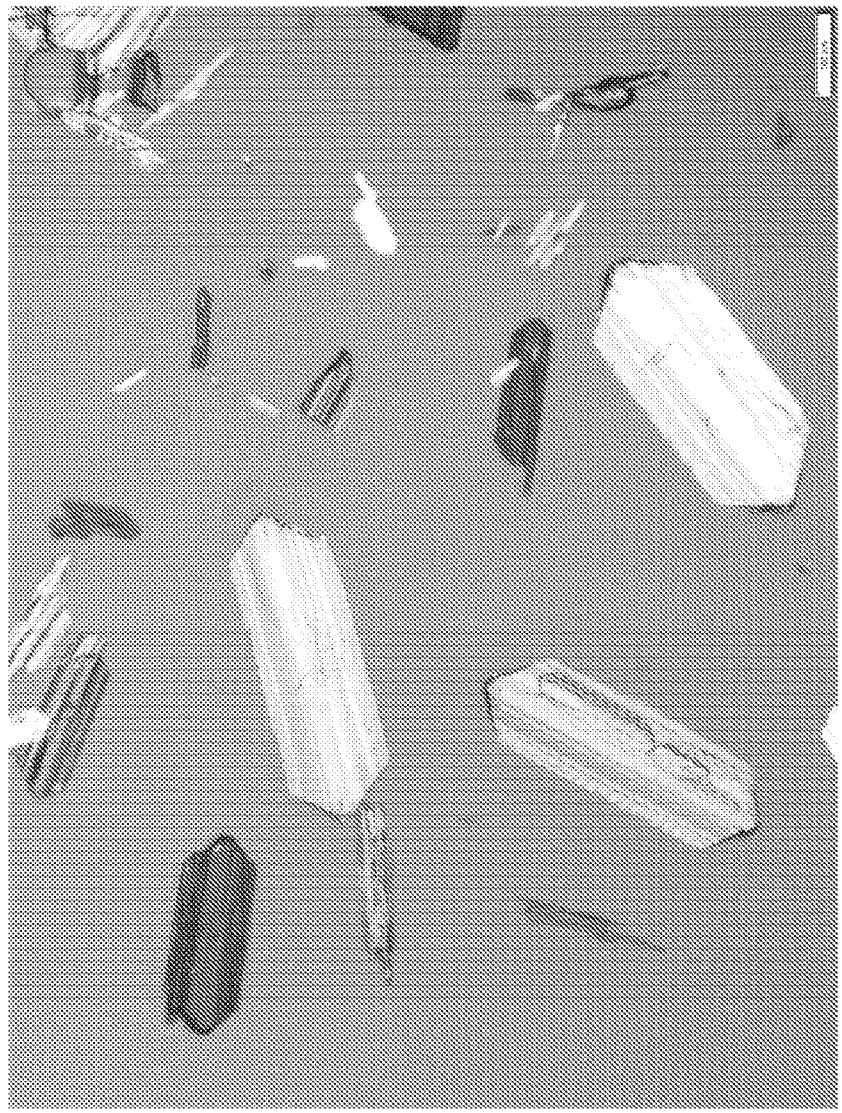
FIG. 12 shows microscopy of Compound 1 (CC-90010) Form I.
Figure 13:
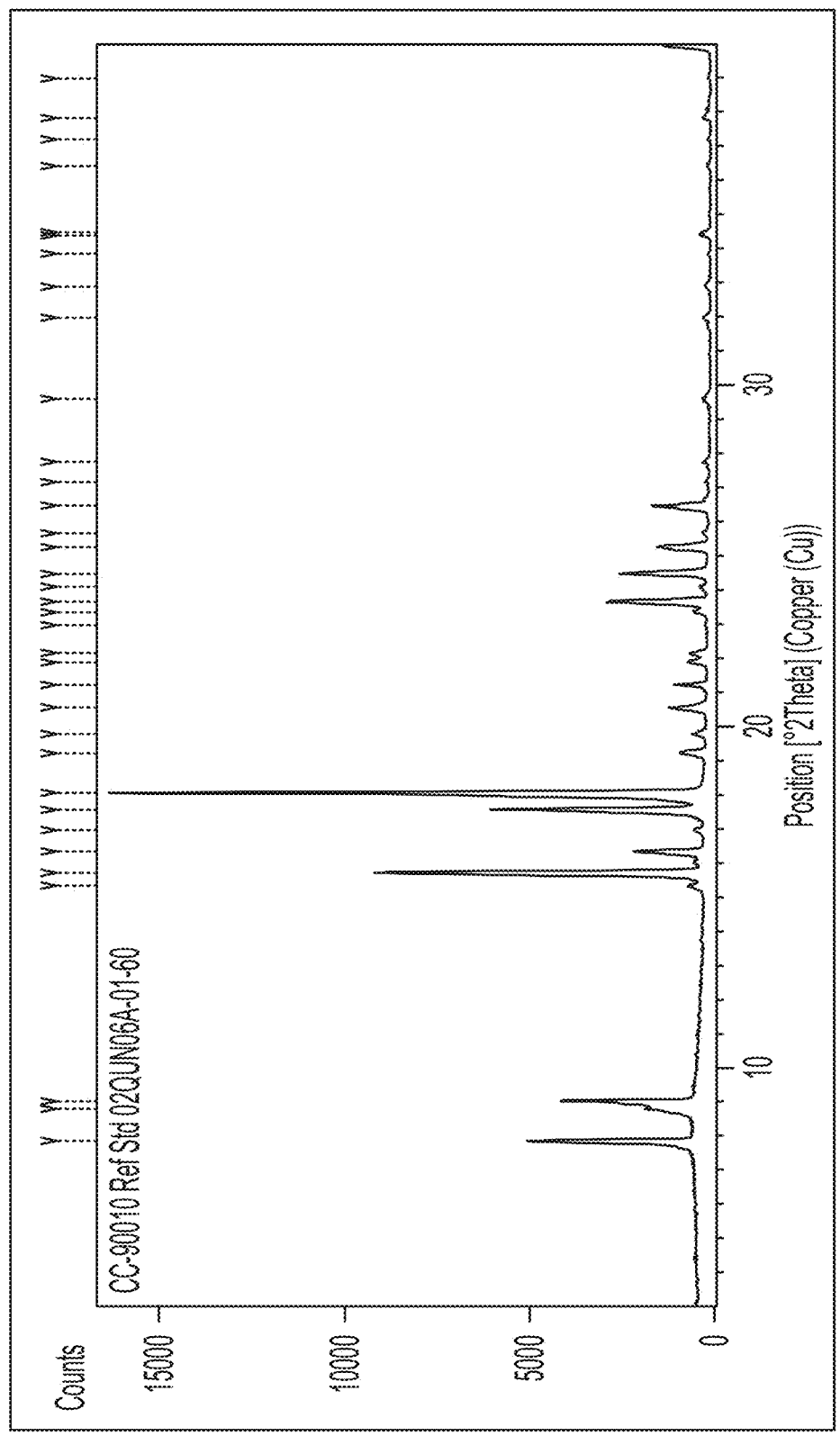
FIG. 13 shows XRPD of Compound 1 (CC-90010) Form I.

FIG. 11 shows $^1$H NMR of Compound 1 (CC-90010). Solvent: d6DMSO; and FIG. 12 shows microscopy of Compound 1 (CC-90010) Form I. FIG. 13 shows XRPD of Compound 1 (CC-90010) Form I, with peak information detailed in Table 6:

TABLE 6

| No. | Pos. [°2Th.] | d-spacing [Å] | Rel. Int. [%] |
|---|---|---|---|
| 1 | 7.848639 | 11.26463 | 28.08 |
| 2 | 8.786152 | 10.06464 | 8.34 |
| 3 | 9.029003 | 9.79448 | 22.96 |
| 4 | 15.3269 | 5.78113 | 2.61 |
| 5 | 15.7163 | 5.63876 | 54.48 |
| 6 | 16.33764 | 5.42569 | 12.05 |
| 7 | 16.96594 | 5.22614 | 1.71 |
| 8 | 17.56643 | 5.04883 | 35.98 |
| 9 | 18.04998 | 4.91464 | 100 |
| 10 | 19.22664 | 4.61645 | 4.27 |
| 11 | 19.77337 | 4.49002 | 2.3 |
| 12 | 20.54306 | 4.3235 | 6.21 |
| 13 | 21.22113 | 4.18686 | 4.48 |
| 14 | 21.87546 | 4.06308 | 3.19 |
| 15 | 22.13877 | 4.01535 | 2.89 |
| 16 | 22.97622 | 3.87085 | 0.46 |
| 17 | 23.35649 | 3.80869 | 2.35 |
| 18 | 23.65442 | 3.76139 | 16.68 |
| 19 | 24.08656 | 3.69487 | 1.33 |
| 20 | 24.47663 | 3.63687 | 14.86 |
| 21 | 25.2578 | 3.52613 | 8.13 |
| 22 | 25.65436 | 3.47252 | 0.89 |
| 23 | 26.45718 | 3.36894 | 9.48 |
| 24 | 27.16849 | 3.28233 | 0.45 |
| 25 | 27.74005 | 3.21599 | 1.05 |
| 26 | 29.58503 | 3.0195 | 1.03 |
| 27 | 31.96313 | 2.80007 | 1.19 |
| 28 | 32.88567 | 2.7236 | 0.86 |
| 29 | 33.84791 | 2.64834 | 0.31 |
| 30 | 34.38817 | 2.6058 | 1.64 |
| 31 | 34.47198 | 2.60181 | 1.58 |
| 32 | 36.42635 | 2.46658 | 0.63 |
| 33 | 37.21594 | 2.41604 | 0.33 |
| 34 | 37.82887 | 2.37829 | 1.25 |
| 35 | 38.99599 | 2.30976 | 0.47 |

Figure 14:
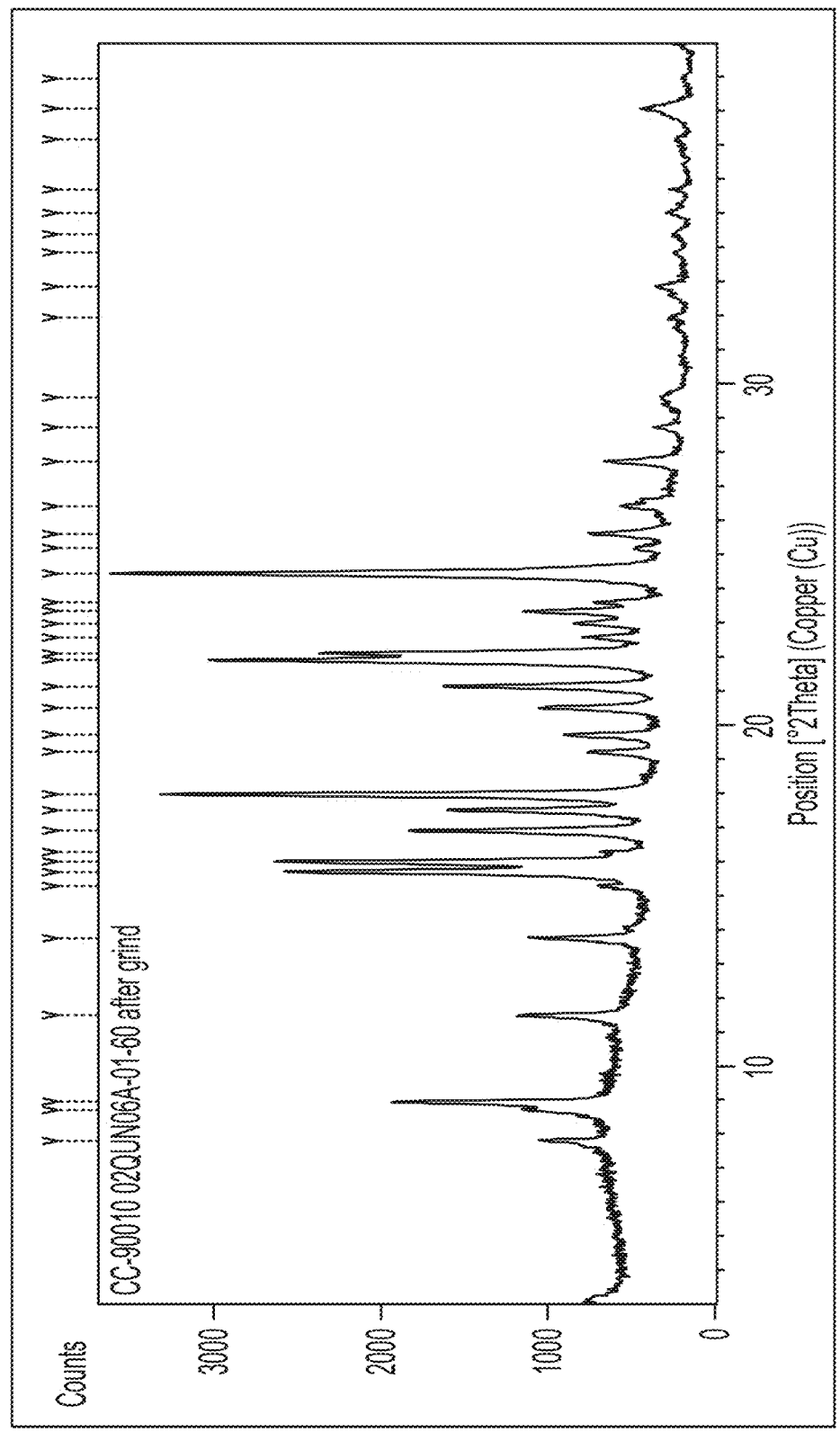
FIG. 14 shows XRPD of CC-90010 Form I after grinding (preferred orientation).

FIG. 14 shows XRPD of CC-90010 Form 1 after grinding (preferred orientation), with peak information detailed in Table 7:

TABLE 7

| No. | Pos. [°2Th.] | d-spacing [Å] | Rel. Int. [%] |
|---|---|---|---|
| 1 | 7.807098 | 11.32447 | 13.16 |
| 2 | 8.691139 | 10.17446 | 15.67 |
| 3 | 8.944468 | 9.88685 | 40.82 |
| 4 | 11.47771 | 7.70979 | 20.22 |
| 5 | 13.75333 | 6.43883 | 19.45 |
| 6 | 15.27651 | 5.80009 | 8.04 |
| 7 | 15.69109 | 5.64776 | 64.51 |
| 8 | 15.99297 | 5.54183 | 66.46 |
| 9 | 16.27756 | 5.44557 | 7.77 |
| 10 | 16.89633 | 5.24752 | 43.12 |

TABLE 7-continued

| No. | Pos. [°2Th.] | d-spacing [Å] | Rel. Int. [%] |
|---|---|---|---|
| 11 | 17.50072 | 5.06763 | 36.25 |
| 12 | 17.96524 | 4.93763 | 88.03 |
| 13 | 19.20236 | 4.62223 | 11.22 |
| 14 | 19.70334 | 4.50582 | 15.85 |
| 15 | 20.50266 | 4.33193 | 20.82 |
| 16 | 21.13626 | 4.20348 | 38.66 |
| 17 | 21.89583 | 4.05935 | 81.05 |
| 18 | 22.10196 | 4.02195 | 61.36 |
| 19 | 22.57031 | 3.93954 | 13.52 |
| 20 | 22.97552 | 3.87097 | 16.48 |
| 21 | 23.32722 | 3.8134 | 25.65 |
| 22 | 23.5865 | 3.77206 | 13.16 |
| 23 | 24.44054 | 3.64216 | 100 |
| 24 | 25.17524 | 3.53751 | 6.64 |
| 25 | 25.60385 | 3.47925 | 14.72 |
| 26 | 26.41086 | 3.37474 | 9.88 |
| 27 | 27.71849 | 3.21844 | 12.35 |
| 28 | 28.72787 | 3.10761 | 4.64 |
| 29 | 29.60304 | 3.0177 | 3.73 |
| 30 | 31.95225 | 2.801 | 2.61 |
| 31 | 32.84832 | 2.72661 | 5.47 |
| 32 | 33.83981 | 2.64895 | 2.15 |
| 33 | 34.39729 | 2.60729 | 2.3 |
| 34 | 35.02682 | 2.56186 | 3.75 |
| 35 | 35.70021 | 2.51506 | 2.55 |
| 36 | 37.16499 | 2.41923 | 2.11 |
| 37 | 38.06795 | 2.3639 | 8.22 |
| 38 | 38.94192 | 2.31284 | 1.09 |

Figure 15:
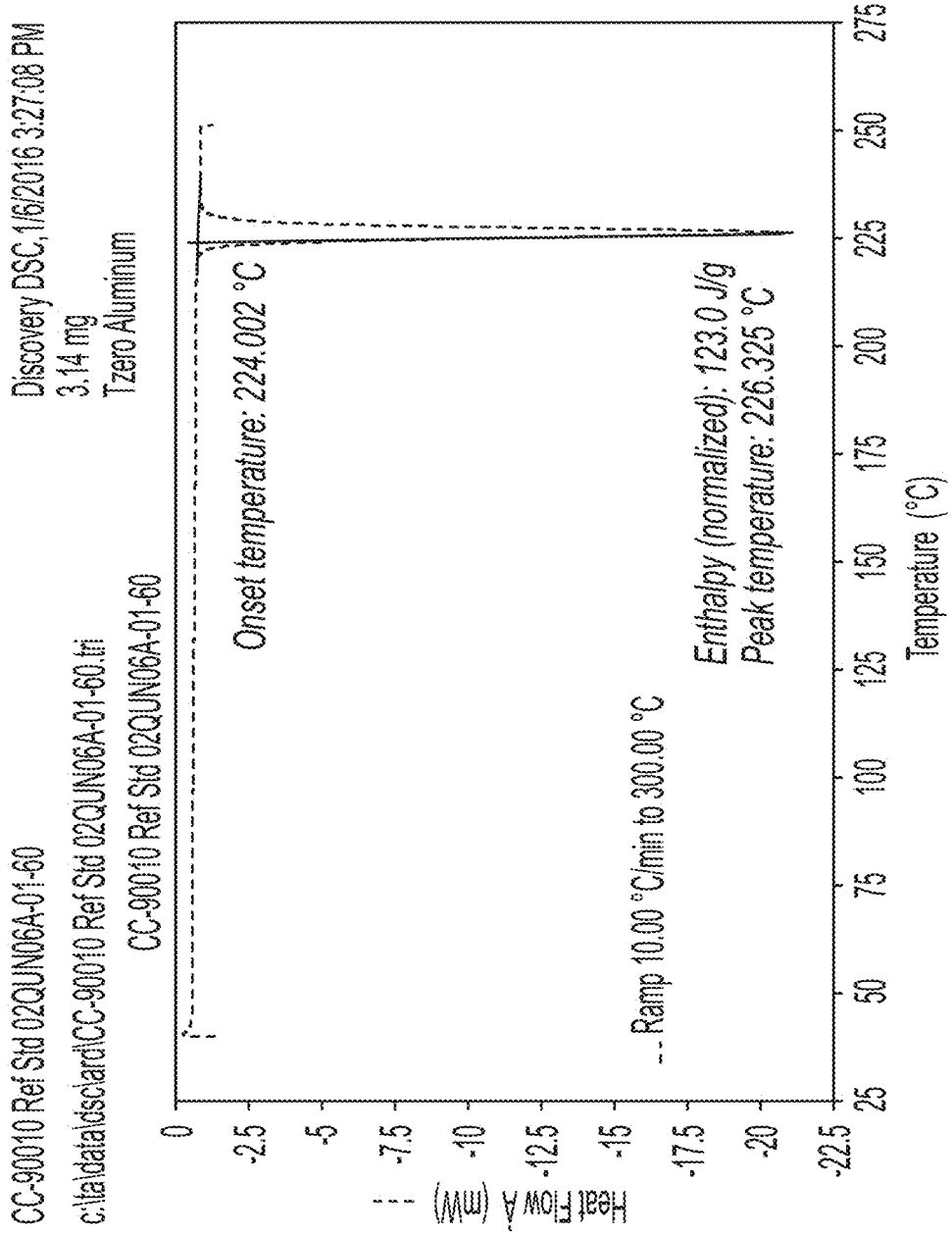
FIG. 15 shows DSC of Compound 1 (CC-90010) Form I.
Figure 16:
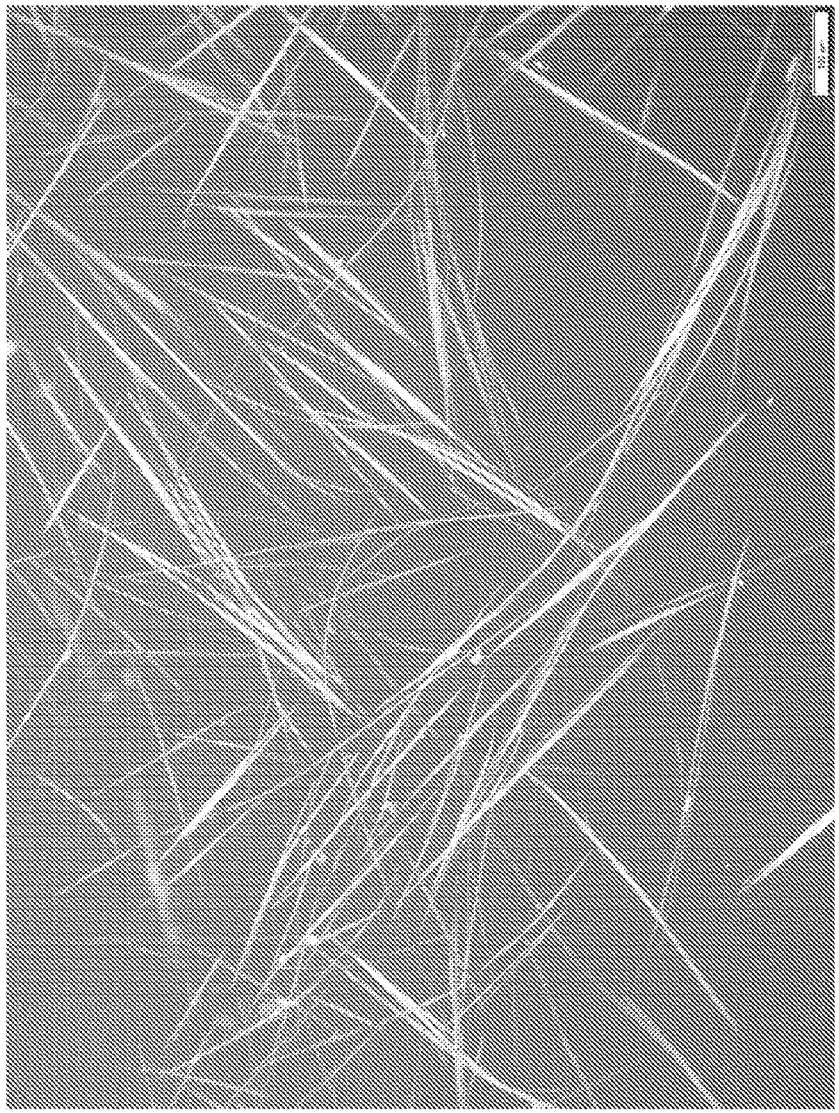
FIG. 16 shows microscopy of Compound 1 (CC-90010) (Metastable) Form 4.
Figure 17:
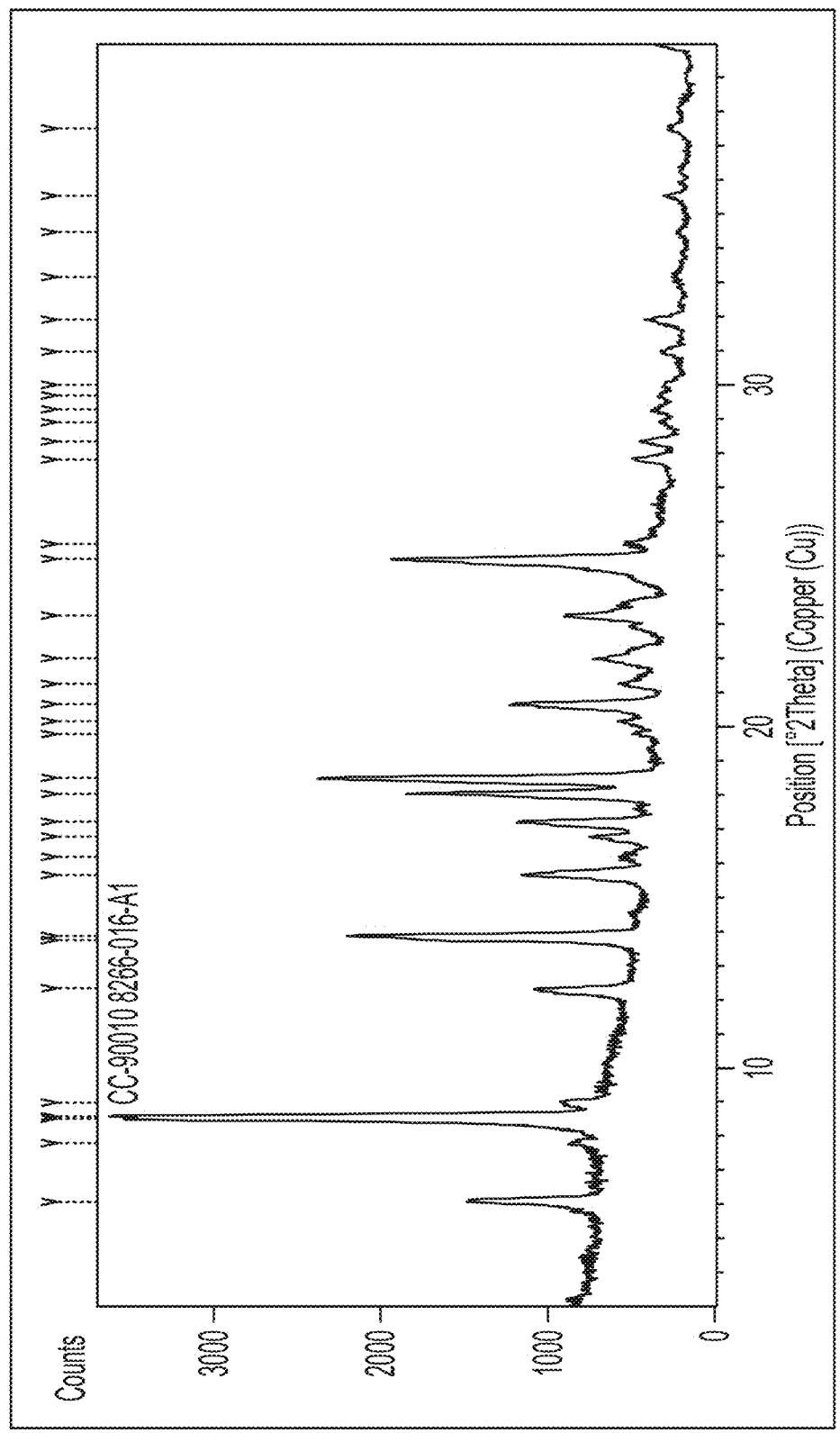
FIG. 17 shows XRPD of Compound 1 (CC-90010) (Metastable) Form 4.

FIG. 15 shows DSC of Compound 1 (CC-90010) Form 1, FIG. 16 shows microscopy of Compound 1 (CC-90010) (Metastable) Form 4, and FIG. 17 shows XRPD of Compound 1 (CC-90010) (Metastable) Form 4, with peak information detailed in Table 8:

TABLE 8

| No. | Pos. [°2Th.] | d-spacing [Å] | Rel. Int. [%] |
|---|---|---|---|
| 1 | 6.087217 | 14.51968 | 26.56 |
| 2 | 7.793917 | 11.34359 | 6.74 |
| 3 | 8.509974 | 10.39065 | 97.04 |
| 4 | 8.579043 | 10.30715 | 100 |
| 5 | 8.99054 | 9.83629 | 8.89 |
| 6 | 12.32699 | 7.18047 | 18.46 |
| 7 | 13.73797 | 6.44599 | 41.07 |
| 8 | 13.86551 | 6.38698 | 56.23 |
| 9 | 15.65508 | 5.66067 | 23.89 |
| 10 | 16.16462 | 5.48337 | 4.25 |
| 11 | 16.76656 | 5.28784 | 11.47 |
| 12 | 17.20469 | 5.15416 | 24.93 |
| 13 | 18.03321 | 4.91918 | 49.12 |
| 14 | 18.48628 | 4.79963 | 66.84 |
| 15 | 19.79159 | 4.48593 | 3.67 |
| 16 | 20.13855 | 4.40942 | 6.96 |
| 17 | 20.6493 | 4.30149 | 28.13 |
| 18 | 21.24317 | 4.18256 | 6.96 |
| 19 | 21.98468 | 4.04314 | 12.38 |
| 20 | 23.25331 | 3.82535 | 19.7 |
| 21 | 24.89191 | 3.57713 | 55.35 |
| 22 | 25.35439 | 3.51292 | 7.79 |
| 23 | 27.82135 | 3.20677 | 7.29 |
| 24 | 28.34437 | 3.14878 | 6.75 |
| 25 | 28.91448 | 3.08798 | 2.93 |
| 26 | 29.28762 | 3.04948 | 4.24 |
| 27 | 29.70119 | 3.00547 | 4.04 |
| 28 | 29.99281 | 2.97937 | 3.01 |
| 29 | 30.96875 | 2.88767 | 3.71 |
| 30 | 31.91952 | 2.80379 | 6.16 |
| 31 | 33.16705 | 2.70113 | 1.59 |
| 32 | 34.47872 | 2.60132 | 1.7 |

TABLE 8-continued

| No. | Pos. [°2Th.] | d-spacing [Å] | Rel. Int. [%] |
|---|---|---|---|
| 33 | 35.53605 | 2.52631 | 3.93 |
| 34 | 37.5243 | 2.39689 | 3.42 |

Figure 18:
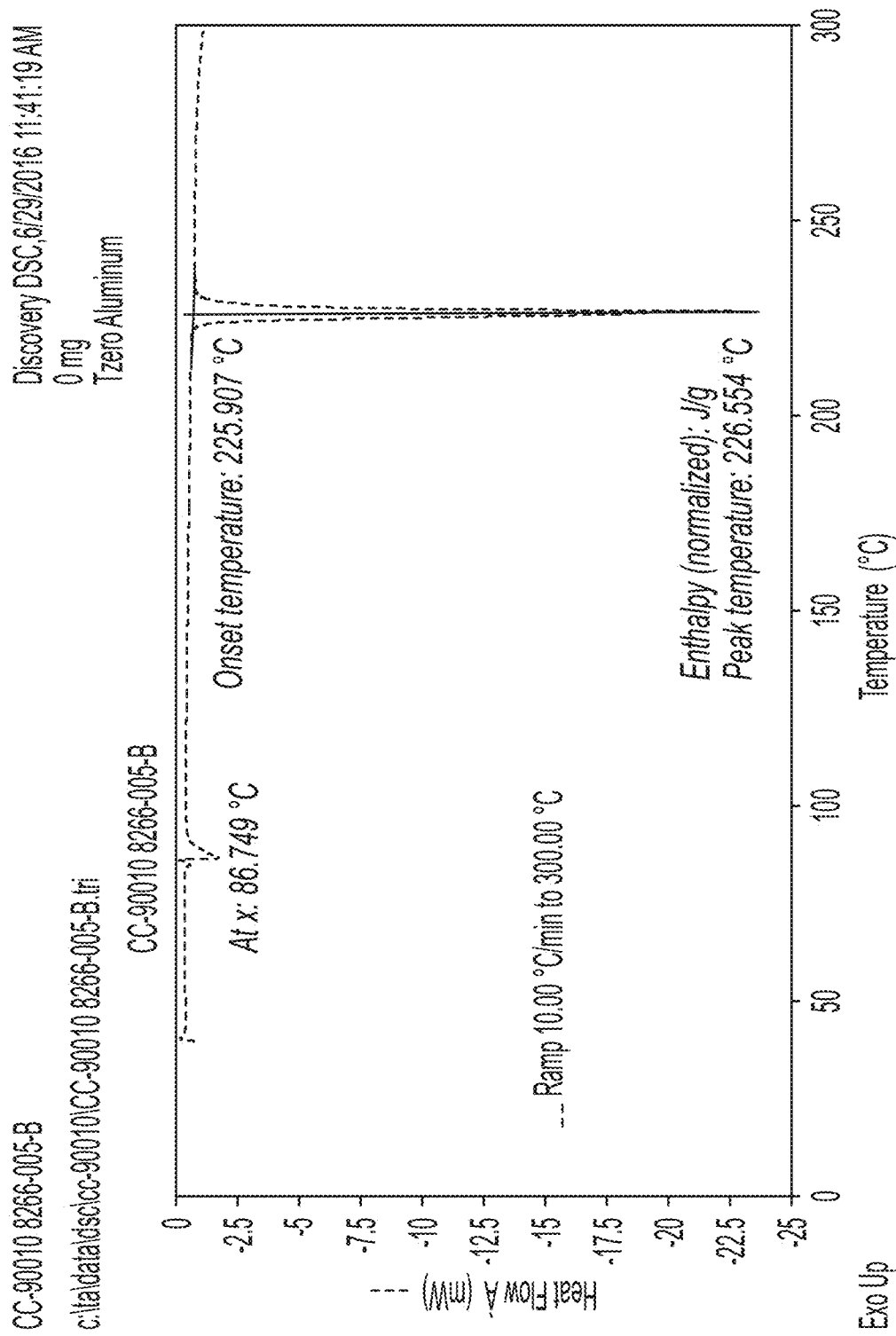
FIG. 18 shows DSC of Compound 1 (CC-90010) (Metastable) Form 4.
Figure 19:
FIG. 19 shows microscopy of Compound 1 (CC-90010) (Metastable) Form 5.
Figure 20:
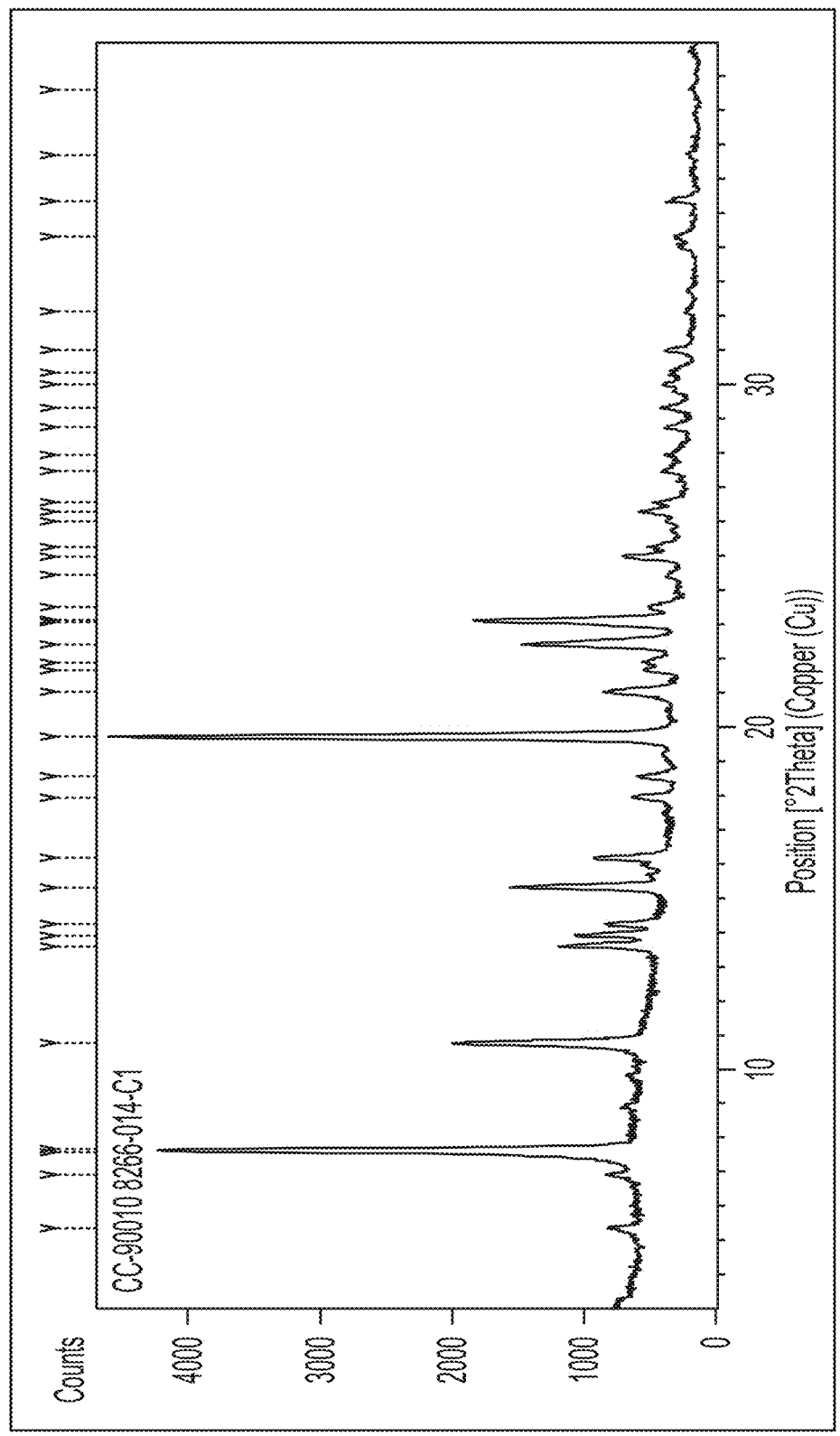
FIG. 20 shows XRPD of Compound 1 (CC-90010) (Metastable) Form 5.

FIG. 18 shows DSC of Compound 1 (CC-90010) (Metastable) Form 4, FIG. 19 shows microscopy of Compound 1 (CC-90010) (Metastable) Form 5, and FIG. 20 shows XRPD of Compound 1 (CC-90010) (Metastable) Form 5, with peak information detailed in Table 9:

TABLE 9

| No. | Pos. [°2Th.] | d-spacing [Å] | Rel. Int. [%] |
|---|---|---|---|
| 1 | 5.367535 | 16.46476 | 4.56 |
| 2 | 6.912349 | 12.7882 | 4.54 |
| 3 | 7.587297 | 11.65204 | 78.31 |
| 4 | 7.661662 | 11.53911 | 79.95 |
| 5 | 10.75874 | 8.22335 | 33.83 |
| 6 | 13.58771 | 6.51693 | 16.5 |
| 7 | 13.90358 | 6.36958 | 14.71 |
| 8 | 14.22759 | 6.22525 | 9.12 |
| 9 | 15.31164 | 5.78686 | 26.1 |
| 10 | 16.16874 | 5.48198 | 12.65 |
| 11 | 17.94544 | 4.94304 | 6.77 |
| 12 | 18.54401 | 4.78481 | 5.79 |
| 13 | 19.70901 | 4.50454 | 100 |
| 14 | 21.02144 | 4.22618 | 12.21 |
| 15 | 21.66252 | 4.10254 | 5.43 |
| 16 | 21.86711 | 4.06125 | 6.05 |
| 17 | 22.40511 | 3.96821 | 26.72 |
| 18 | 23.06447 | 3.85305 | 34.38 |
| 19 | 23.1363 | 3.84443 | 32.67 |
| 20 | 23.48621 | 3.78794 | 5.07 |
| 21 | 24.42764 | 3.64405 | 2.3 |
| 22 | 24.97185 | 3.56585 | 10.07 |
| 23 | 25.25386 | 3.52667 | 5.05 |
| 24 | 25.99026 | 3.42556 | 3.48 |
| 25 | 26.28902 | 3.39011 | 7.62 |
| 26 | 26.54997 | 3.35738 | 5.01 |
| 27 | 27.47343 | 3.24659 | 3.48 |
| 28 | 27.94074 | 3.19334 | 3.05 |
| 29 | 28.74656 | 3.10563 | 3.5 |
| 30 | 29.32182 | 3.046 | 4.68 |
| 31 | 30.00715 | 2.97798 | 4.29 |
| 32 | 30.34702 | 2.9454 | 3.12 |
| 33 | 31.00177 | 2.88467 | 4.25 |
| 34 | 32.14843 | 2.78435 | 1.16 |
| 35 | 34.31352 | 2.61346 | 3.45 |
| 36 | 35.3472 | 2.53937 | 4.58 |
| 37 | 36.70614 | 2.44842 | 1.27 |
| 38 | 38.60992 | 2.33196 | 0.71 |

Figure 21:
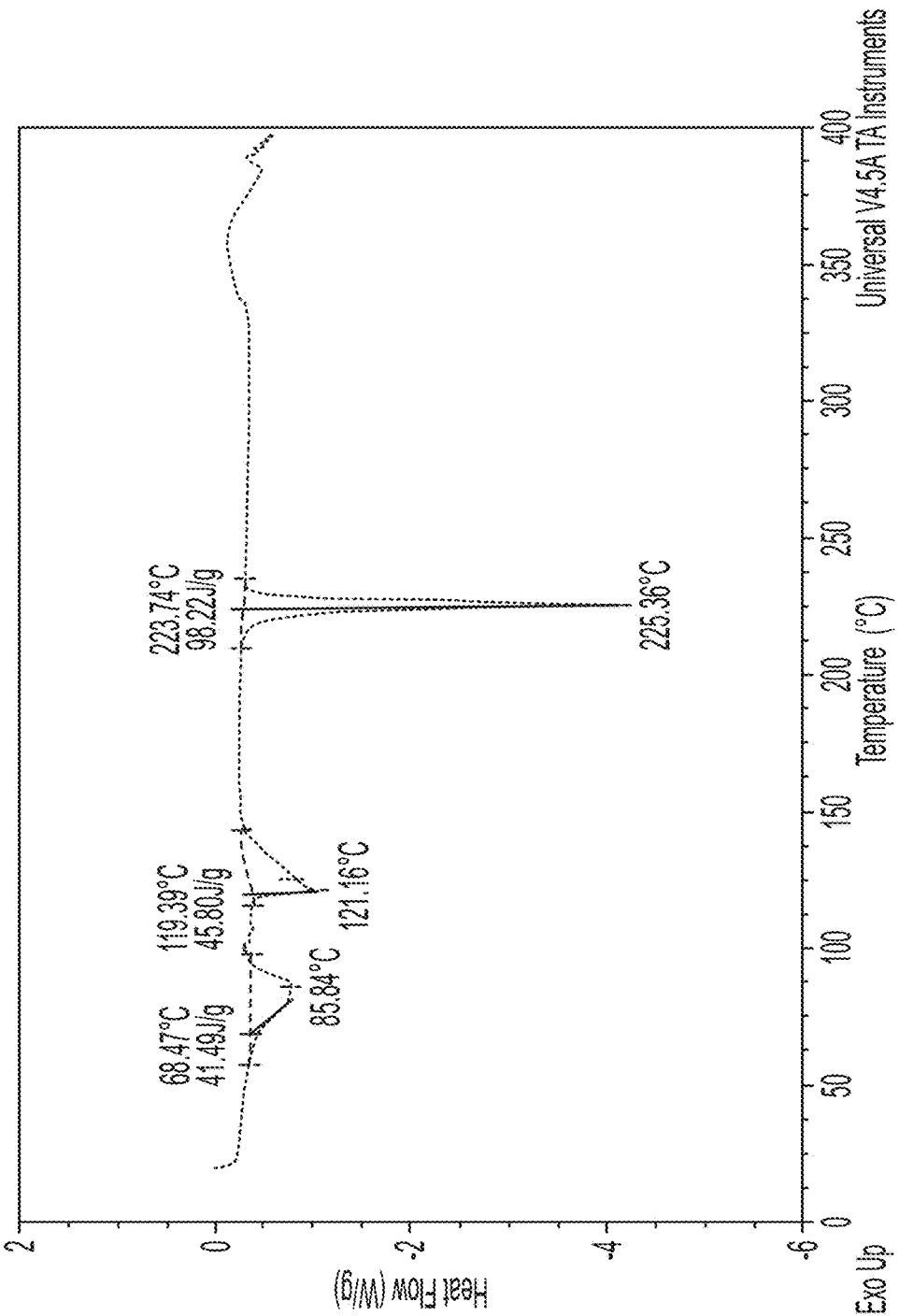
FIG. 21 shows DSC of Compound 1 (CC-90010) (Metastable) Form 5.

FIG. 21 shows DSC of Compound 1 (CC-90010) (Metastable) Form 5.

Four processes are described below. All use only formic acid, an ICH class III solvent, and water. The two processes to Form 1 (most stable polymorph) both control the polymorph by seeding with Form 1, and are more volumetrically efficient (14 to 16× vol). A process to form (metastable) Form 4, and process to form (metastable) Form 5, are also provided. For all of the methods described, the solvent ratios can be changed, the temperature can be changed, the seed amount can be changed, the wash compositions and amounts can be changed, and the drying temperature can be changed.

Process 1 (for Form 1): Compound 1 (1.0× wt) and formic acid (7.0× vol) are charged to Reactor 1. This mixture is agitated and then transferred to reactor 2 via a polish filter. Formic acid (1.0× vol) is charged to reactor 1 then transferred through the same polish filter to Reactor 2. Water (2.2× vol) is charged via a separate polish filter to Reactor 2 over 1 hour. Compound 1 seeds (1% wt, Form 1) are charged and the batch is held at about 20° C. to about 25° C. Water (4.8× vol) is charged to reactor 2 via a polish filter in three separate charges (0.25, 0.60, and 3.95× vol). Each charge is added over 1 hour, with a 1 hour hold between charges. After all three charges, the batch is held for at least one hour. A batch temperature of about 20° C. to about 25° C. is maintained for all charges.

The batch is filtered, washed twice with polish filtered formic acid and water (1.5× vol formic acid+1.5× vol water each), twice with polish filtered water (3× vol each), and dried under reduced pressure at about 35° C. to about 45° C.

Process 2 (for Form 1): Compound 1 (CC-90010) (1.0× wt) is charged to formic acid (5.0× vol) in Reactor 1 and agitated at 20° C. to 30° C. until dissolved. Polish filtered formic acid (2.0× vol) and polish filtered water (1.8× vol) are charged to Reactor 2 and agitated at 20° C. to 30° C. Compound 1 (CC-90010) seeds (Form 1, 0.02 to 0.04× wt) are charged to Reactor 2, and the resulting slurry is agitated for at least 60 minutes.

The Compound 1 (CC-90010)/formic acid solution in Reactor 1 and water (4.4× vol) are then simultaneously charged via polish filters to the seed bed slurry in Reactor 2 over 6 to 10 hours while maintaining a temperature of about 20° C. to about 30° C. After the addition, formic acid (1× vol) is charged to Reactor 1. The formic acid rinse in Reactor 1 and water (0.9× vol) are simultaneously charged via polish filters to the batch in Reactor 2 over at least 15 minutes while maintaining a temperature of about 20° C. to about 30° C.

Process for Form 4: Compound 1 (CC-90010) (1.0× wt) is charged to a reaction flask followed by formic acid (8.0× vol) and water 2.2× vol). A small amount of Form 1 seeds are charged and this mixture is agitated at about 20° C. to about 25° C. for 2 hours. The slurry is filtered and the wet cake is not dried.

Process for Form 5: Compound 1 (CC-90010) (1.0× wt) is charged to the reaction flask followed by formic acid (8.0× vol) and water 2.2× vol). This mixture is agitated at about 15° C. for about 4 hours. The slurry is filtered and the wet cake is not dried. The batch is filtered, washed twice with polish filtered formic acid and water (1.5× vol formic acid+1.5× vol water each), twice with polish filtered water (3× vol each), and dried under reduced pressure at about 35° C. to about 45° C.

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A process for the preparation of a compound of formula I, a hydrate, solvate, or pharmaceutically acceptable salt thereof:

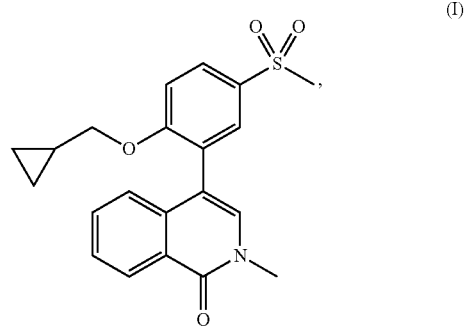 [SMILES: Cn1cc(-c2cc(S(C)(=O)=O)ccc2OCC2CC2)c2ccccc2c1=O]

the process comprising:
coupling a compound of formula II with a compound of formula III, to provide the compound of formula I;

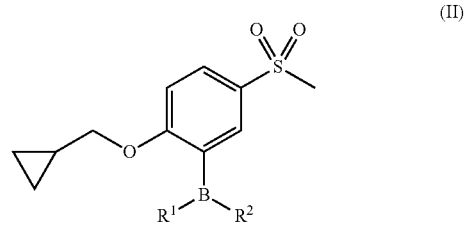

-continued

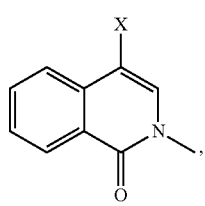
(III)

wherein:
X is Cl, Br, or I; and
R¹, R² and the boron to which they are attached together form an optionally substituted 5-10 membered ring comprising carbon and from 0 to 5 heteroatoms.

2. The process of claim 1, wherein X is Br.

3. The process of claim 1, wherein R¹, R² and the boron to which they are attached together form an optionally substituted 5-10 membered ring comprising carbon and from 0 to 5 heteroatoms selected from O and N.

4. The process of claim 1, wherein R¹, R² and the boron to which they are attached together form an optionally substituted 5-10 membered ring wherein the two atoms of the ring directly attached to boron are oxygens.

5. The process of claim 4, wherein the optionally substituted 5-10 membered ring comprising boron comprises from 1 to 3 nitrogen atoms.

6. The process of claim 1, wherein the optionally substituted ring comprising boron is an 8 membered ring.

7. The process of claim 1, wherein the compound of formula II is of formula II-a:

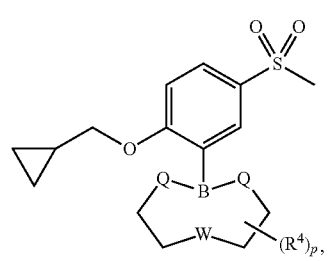
(II-a)

wherein:
each Q is independently selected from —O—, —NH—, —N(R⁵)—, or optionally substituted methylene;
W is —O—, —NH— or —N(R⁵)—;
each R⁴ is independently selected from H, OH, CN, optionally substituted amino, —C(O)R⁵, —COOR⁵, —C(O)N(R⁵)₂, —SO2R⁵, an optionally substituted $C_1$-$C_5$ alkyl, an optionally substituted $C_1$-$C_5$ alkenyl, an optionally substituted $C_1$-$C_5$ alkynyl, an optionally substituted 4-10 membered heterocyclyl, an optionally substituted 5-10 membered heteroaryl, an optionally substituted 6-10 membered aryl, or an optionally substituted 4-7 membered cycloalkyl;
each R⁵ is independently selected from H, an optionally substituted $C_1$-$C_5$ alkyl, an optionally substituted $C_1$-$C_5$ alkenyl, an optionally substituted $C_1$-$C_5$ alkynyl, an optionally substituted 4-10 membered heterocyclyl, an optionally substituted 5-10 membered heteroaryl, an optionally substituted 6-10 membered aryl, or an optionally substituted 4-7 membered cycloalkyl; and
p is 0 to 4.

8. The process of claim 1, wherein the compound of formula II is of formula II-b:

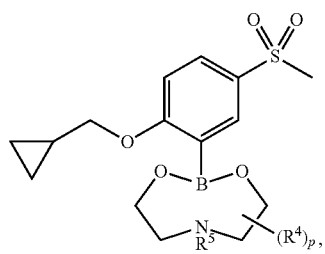
(II-b)

wherein:
each R⁴ is independently selected from H, OH, CN, optionally substituted amino, —C(O)R⁵, —COOR⁵, —C(O)N(R⁵)₂, —SO₂R⁵, an optionally substituted $C_1$-$C_5$ alkyl, an optionally substituted $C_1$-$C_5$ alkenyl, an optionally substituted $C_1$-$C_5$ alkynyl, an optionally substituted 4-10 membered heterocyclyl, an optionally substituted 5-10 membered heteroaryl, an optionally substituted 6-10 membered aryl, or an optionally substituted 4-7 membered cycloalkyl;
each R⁵ is independently selected from H, an optionally substituted $C_1$-$C_5$ alkyl, an optionally substituted $C_1$-$C_5$ alkenyl, an optionally substituted $C_1$-$C_5$ alkynyl, an optionally substituted 4-10 membered heterocyclyl, an optionally substituted 5-10 membered heteroaryl, an optionally substituted 6-10 membered aryl, or an optionally substituted 4-7 membered cycloalkyl; and
p is 0 to 4.

9. The process of claim 1, wherein the compound of formula II is:

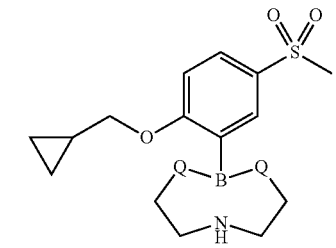

10. The process of claim 9, wherein the compound of formula II is formed by contacting a compound of formula IV with bis(pinacolato)diboron (B₂pin₂), a palladium catalyst, and diethanolamine (DEA), wherein the compound of formula IV has the following structure:

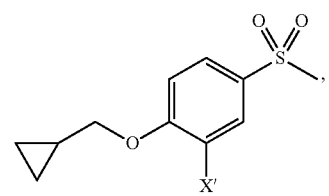
(IV)

wherein X' is Cl, Br, or I.

11. The process of claim 10, wherein the compound of formula IV is produced by monobromination of a compound of formula V:

(V)

[Chemical structure: 4-hydroxyphenyl methyl sulfone]

to produce a compound of formula VI:

(VI)

[Chemical structure: 2-bromo-4-(methylsulfonyl)phenol]

and O-alkylating the compound of formula VI to produce the compound of formula IV, wherein X' is Br.

12. The process of claim 11, wherein monobromination proceeds over dibromination of the compound of formula V at a ratio of about 95:5 or greater.

13. The process of claim 11, wherein monobromination proceeds over dibromination of the compound of formula V at a ratio of about 99:1 or greater.

14. The process of claim 1, further comprising crystallizing the compound of formula I from a mixture of formic acid and water.

15. The process of claim 14, wherein the crystallized compound of formula I comprises the X-ray powder diffraction (XRPD) pattern having the following specifications:

| No. | Pos. [°2θ] | d-spacing [Å] | Rel. Int. [%] |
|---|---|---|---|
| 1 | 7.807098 | 11.32447 | 13.16 |
| 2 | 8.691139 | 10.17446 | 15.67 |
| 3 | 8.944468 | 9.88685 | 40.82 |
| 4 | 11.47771 | 7.70979 | 20.22 |
| 5 | 13.75333 | 6.43883 | 19.45 |
| 6 | 15.27651 | 5.80009 | 8.04 |
| 7 | 15.69109 | 5.64776 | 64.51 |
| 8 | 15.99297 | 5.54183 | 66.46 |
| 9 | 16.27756 | 5.44557 | 7.77 |
| 10 | 16.89633 | 5.24752 | 43.12 |
| 11 | 17.50072 | 5.06763 | 36.25 |
| 12 | 17.96524 | 4.93763 | 88.03 |
| 13 | 19.20236 | 4.62223 | 11.22 |
| 14 | 19.70334 | 4.50582 | 15.85 |
| 15 | 20.50266 | 4.33193 | 20.82 |
| 16 | 21.13626 | 4.20348 | 38.66 |
| 17 | 21.89583 | 4.05935 | 81.05 |
| 18 | 22.10196 | 4.02195 | 61.36 |
| 19 | 22.57031 | 3.93954 | 13.52 |
| 20 | 22.97552 | 3.87097 | 16.48 |
| 21 | 23.32722 | 3.8134 | 25.65 |
| 22 | 23.5865 | 3.77206 | 13.16 |
| 23 | 24.44054 | 3.64216 | 100 |
| 24 | 25.17524 | 3.53751 | 6.64 |
| 25 | 25.60385 | 3.47925 | 14.72 |
| 26 | 26.41086 | 3.37474 | 9.88 |
| 27 | 27.71849 | 3.21844 | 12.35 |
| 28 | 28.72787 | 3.10761 | 4.64 |
| 29 | 29.60304 | 3.0177 | 3.73 |
| 30 | 31.95225 | 2.801 | 2.61 |
| 31 | 32.84832 | 2.72661 | 5.47 |
| 32 | 33.83981 | 2.64895 | 2.15 |
| 33 | 34.39729 | 2.60729 | 2.3 |
| 34 | 35.02682 | 2.56186 | 3.75 |
| 35 | 35.70021 | 2.51506 | 2.55 |
| 36 | 37.16499 | 2.41923 | 2.11 |
| 37 | 38.06795 | 2.3639 | 8.22 |
| 38 | 38.94192 | 2.31284 | 1.09. |

16. The process of claim 1, wherein the purity of the compound of formula I is at least about 90%, about 95%, or about 99%.

17. A compound of formula I, a hydrate, solvate, or pharmaceutically acceptable salt thereof, produced by the process of claim 1.

* * * * *

UNITED STATES PATENT AND TRADEMARK OFFICE
CERTIFICATE OF CORRECTION

PATENT NO. : 11,566,004 B2
APPLICATION NO. : 17/262642
DATED : January 31, 2023
INVENTOR(S) : Traverse et al.

Page 1 of 1

It is certified that error appears in the above-identified patent and that said Letters Patent is hereby corrected as shown below:

On the Title Page

UNDER OTHER PUBLICATIONS:

Line 13, "Chemistryi" should be replaced with -- Chemistry --

Line 27, "730(43):" should be replaced with -- 130(43): --

In the Claims

Column 74, Claim 9, Lines 35 to 45, delete:

"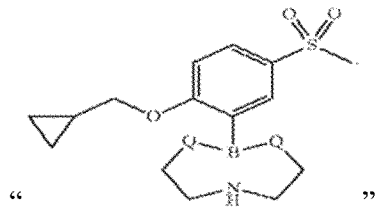"

And insert:

-- 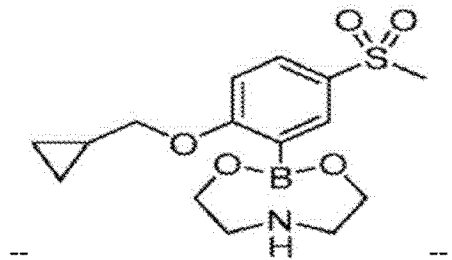 --

Signed and Sealed this
Nineteenth Day of September, 2023

Katherine Kelly Vidal
Director of the United States Patent and Trademark Office